(12) United States Patent
Diab et al.

(10) Patent No.: US 7,937,130 B2
(45) Date of Patent: *May 3, 2011

(54) SIGNAL PROCESSING APPARATUS

(75) Inventors: Mohamed K. Diab, Ladera Ranch, CA (US); Esmaiel Kiani-Azarbayjany, Laguna Niguel, CA (US); Walter M. Weber, Laguna Hills, CA (US)

(73) Assignee: MASIMO Corporation, Irvine, CA (US)

( * ) Notice: Subject to any disclaimer, the term of this patent is extended or adjusted under 35 U.S.C. 154(b) by 39 days.
This patent is subject to a terminal disclaimer.

(21) Appl. No.: 12/340,577

(22) Filed: Dec. 19, 2008

(65) Prior Publication Data

US 2009/0099430 A1 Apr. 16, 2009

Related U.S. Application Data

(63) Continuation of application No. 10/779,033, filed on Feb. 13, 2004, now Pat. No. 7,469,157, which is a continuation of application No. 09/111,604, filed on Jul. 7, 1998, which is a continuation of application No. 08/943,511, filed on Oct. 6, 1997, now Pat. No. 6,263,222, which is a continuation of application No. 08/572,488, filed on Dec. 14, 1995, now Pat. No. 5,685,299, which is a continuation of application No. 08/132,812, filed on Oct. 6, 1993, now Pat. No. 5,490,505, which is a continuation-in-part of application No. 07/666,060, filed on Mar. 7, 1991, now abandoned.

(51) Int. Cl.
*A61B 5/1455* (2006.01)

(52) U.S. Cl. .................................................. 600/336

(58) Field of Classification Search ................. 600/310, 600/322, 323, 330, 336
See application file for complete search history.

(56) References Cited

U.S. PATENT DOCUMENTS 3,638,640 A 2/1972 Shaw
(Continued)

FOREIGN PATENT DOCUMENTS

EP 0 102 816 3/1984
(Continued)

OTHER PUBLICATIONS

U.S. District Court, Central District of California (Western Division—Los Angeles) Civil Docket for Case #: 2:00-cv-06506-MRP-AJW.
(Continued)

*Primary Examiner* — Eric F Winakur
(74) *Attorney, Agent, or Firm* — Knobbe Martens Olson & Bear LLP

(57) ABSTRACT

A signal processor which acquires a first signal, including a first primary signal portion and a first secondary signal portion, and a second signal, including a second primary signal portion and a second secondary signal portion, wherein the first and second primary signal portions are correlated. The signals may be acquired by propagating energy through a medium and measuring an attenuated signal after transmission or reflection. Alternatively, the signals may be acquired by measuring energy generated by the medium. A processor of the present invention generates a primary or secondary reference signal which is a combination, respectively, of only the primary or secondary signal portions. The secondary reference signal is then used to remove the secondary portion of each of the first and second measured signals via a correlation canceler, such as an adaptive noise canceler, preferably of the joint process estimator type. The primary reference signal is used to remove the primary portion of each of the first and second measured signals via a correlation canceler. The processor of the present invention may be employed in conjunction with a correlation canceler in physiological monitors wherein the known properties of energy attenuation through a medium are used to determine physiological characteristics of the medium. Many physiological conditions, such as the pulse, or blood pressure of a patient or the concentration of a constituent in a medium, can be determined from the primary or secondary portions of the signal after other signal portion is removed.

40 Claims, 20 Drawing Sheets

U.S. PATENT DOCUMENTS

| | | | |
|---|---|---|---|
| 3,647,299 A | 3/1972 | Lavallee |
| 3,659,591 A | 5/1972 | Doll et al. |
| 3,704,706 A | 12/1972 | Herczfeld et al. |
| 3,991,277 A | 11/1976 | Hirata |
| 3,998,550 A | 12/1976 | Konishi et al. |
| 4,038,536 A | 7/1977 | Feintuch |
| 4,063,551 A | 12/1977 | Sweeney |
| 4,086,915 A | 5/1978 | Kofsky et al. |
| 4,095,117 A | 6/1978 | Nagy |
| 4,157,708 A | 6/1979 | Imura |
| 4,167,331 A | 9/1979 | Nielsen |
| 4,197,836 A | 4/1980 | Wagner et al. |
| 4,238,746 A | 12/1980 | McCool et al. |
| 4,243,935 A | 1/1981 | McCool et al. |
| 4,266,554 A | 5/1981 | Hamaguri |
| 4,305,398 A | 12/1981 | Sawa |
| 4,407,290 A | 10/1983 | Wilber |
| 4,446,871 A | 5/1984 | Imura |
| 4,458,691 A | 7/1984 | Netravali |
| 4,519,396 A | 5/1985 | Epstein et al. |
| 4,537,200 A | 8/1985 | Widrow |
| 4,582,068 A | 4/1986 | Phillipps et al. |
| 4,586,513 A | 5/1986 | Hamaguri |
| 4,617,589 A | 10/1986 | Weckenbrock |
| 4,623,248 A | 11/1986 | Sperinde |
| 4,649,505 A | 3/1987 | Zinser, Jr. et al. |
| 4,653,498 A | 3/1987 | New, Jr. et al. |
| 4,667,680 A | 5/1987 | Ellis |
| 4,694,833 A | 9/1987 | Hamaguri |
| 4,714,341 A | 12/1987 | Hamaguri et al. |
| 4,723,294 A | 2/1988 | Taguchi |
| 4,751,931 A | 6/1988 | Briller et al. |
| 4,773,422 A | 9/1988 | Isaacson et al. |
| 4,781,200 A | 11/1988 | Baker |
| 4,793,361 A | 12/1988 | DuFault |
| 4,796,636 A | 1/1989 | Branstetter et al. |
| 4,799,486 A | 1/1989 | DuFault |
| 4,799,493 A | 1/1989 | DuFault |
| 4,800,495 A | 1/1989 | Smith |
| 4,800,885 A | 1/1989 | Johnson |
| 4,802,486 A | 2/1989 | Goodman et al. |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,848,901 A | 7/1989 | Hood, Jr. |
| 4,858,199 A | 8/1989 | Griffith |
| 4,859,056 A | 8/1989 | Prosser et al. |
| 4,860,759 A | 8/1989 | Kahn et al. |
| 4,863,265 A | 9/1989 | Flower et al. |
| 4,867,165 A | 9/1989 | Noller et al. |
| 4,867,571 A | 9/1989 | Frick et al. |
| 4,869,253 A | 9/1989 | Craig, Jr. et al. |
| 4,869,254 A | 9/1989 | Stone et al. |
| 4,883,353 A | 11/1989 | Hausman et al. |
| 4,883,356 A | 11/1989 | deMey, II |
| 4,892,101 A | 1/1990 | Cheung et al. |
| 4,897,162 A | 1/1990 | Lewandowski et al. |
| 4,907,594 A | 3/1990 | Muz |
| 4,911,167 A | 3/1990 | Corenman et al. |
| 4,913,150 A | 4/1990 | Cheung et al. |
| 4,927,264 A | 5/1990 | Shiga et al. |
| 4,928,692 A | 5/1990 | Goodman et al. |
| 4,934,372 A | 6/1990 | Corenman et al. |
| 4,942,877 A | 7/1990 | Sakai et al. |
| 4,948,248 A | 8/1990 | Lehman |
| 4,949,710 A | 8/1990 | Dorsett et al. |
| 4,951,680 A | 8/1990 | Kirk et al. |
| 4,955,379 A | 9/1990 | Hall |
| 4,956,867 A | 9/1990 | Zurek et al. |
| 4,960,126 A | 10/1990 | Conlon et al. |
| 4,960,128 A | 10/1990 | Gordon et al. |
| 4,964,408 A | 10/1990 | Hink et al. |
| 4,967,571 A | 11/1990 | Sporri |
| 5,003,977 A | 4/1991 | Suzuki et al. |
| 5,036,857 A | 8/1991 | Semmlow et al. |
| 5,040,201 A | 8/1991 | Slump |
| 5,041,187 A | 8/1991 | Hink et al. |
| 5,042,499 A | 8/1991 | Frank et al. |
| 5,054,495 A | 10/1991 | Uemura et al. |
| 5,057,695 A | 10/1991 | Hirao et al. |
| 5,069,213 A | 12/1991 | Polczynski |
| 5,078,136 A | 1/1992 | Stone et al. |
| 5,152,296 A | 10/1992 | Simons |
| 5,154,176 A | 10/1992 | Kanda |
| 5,163,438 A | 11/1992 | Gordon et al. |
| 5,170,791 A | 12/1992 | Boos et al. |
| 5,188,108 A | 2/1993 | Secker |
| 5,190,038 A | 3/1993 | Polson et al. |
| 5,190,047 A | 3/1993 | Odagiri et al. |
| 5,218,962 A | 6/1993 | Mannheimer |
| 5,243,993 A | 9/1993 | Alexander et al. |
| 5,246,002 A | 9/1993 | Prosser |
| 5,259,381 A | 11/1993 | Cheung et al. |
| 5,273,036 A | 12/1993 | Kronberg et al. |
| 5,285,784 A | 2/1994 | Seeker |
| 5,299,120 A | 3/1994 | Kaestle |
| 5,337,744 A | 8/1994 | Branigan |
| 5,341,805 A | 8/1994 | Stavridi et al. |
| 5,355,880 A | 10/1994 | Thomas et al. |
| 5,355,882 A | 10/1994 | Ukawa et al. |
| 5,368,026 A | 11/1994 | Swedlow et al. |
| D353,195 S | 12/1994 | Savage et al. |
| D353,196 S | 12/1994 | Savage et al. |
| 5,377,676 A | 1/1995 | Vari et al. |
| 5,379,238 A | 1/1995 | Stark |
| 5,379,774 A | 1/1995 | Nishimura et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,448,991 A | 9/1995 | Polson et al. |
| 5,452,717 A | 9/1995 | Branigan et al. |
| D363,120 S | 10/1995 | Savage et al. |
| 5,456,252 A | 10/1995 | Vari et al. |
| 5,458,128 A | 10/1995 | Polanyi et al. |
| RE35,122 E | 12/1995 | Corenman et al. |
| 5,482,036 A | 1/1996 | Diab et al. |
| 5,490,505 A | 2/1996 | Diab et al. |
| 5,494,032 A | 2/1996 | Robinson et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,562,002 A | 10/1996 | Lalin |
| 5,575,284 A | 11/1996 | Athan et al. |
| 5,590,649 A | 1/1997 | Caro et al. |
| 5,602,924 A | 2/1997 | Durand et al. |
| 5,630,413 A | 5/1997 | Thomas et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,662,105 A | 9/1997 | Tien |
| 5,685,299 A | 11/1997 | Diab et al. |
| D393,476 S | 4/1998 | Lodige |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,800,348 A | 9/1998 | Kaestle |
| 5,810,734 A | 9/1998 | Caro et al. |
| 5,823,950 A | 10/1998 | Diab et al. |
| 5,830,131 A | 11/1998 | Caro et al. |
| 5,830,137 A | 11/1998 | Scharf |
| 5,833,618 A | 11/1998 | Caro et al. |
| 5,842,981 A | 12/1998 | Larsen et al. |
| 5,853,364 A | 12/1998 | Baker, Jr. et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,277 A | 8/1999 | Mortz |
| 5,934,925 A | 8/1999 | Tobler et al. |

| Patent No. | Kind | Date | Inventor(s) |
|---|---|---|---|
| 5,940,182 | A | 8/1999 | Lepper, Jr. et al. |
| 5,995,855 | A | 11/1999 | Kiani et al. |
| 5,997,343 | A | 12/1999 | Mills et al. |
| 6,002,952 | A | 12/1999 | Diab et al. |
| 6,011,985 | A | 1/2000 | Athan |
| 6,011,986 | A | 1/2000 | Diab et al. |
| 6,027,452 | A | 2/2000 | Flaherty et al. |
| 6,036,642 | A | 3/2000 | Diab et al. |
| 6,045,509 | A | 4/2000 | Caro et al. |
| 6,067,462 | A | 5/2000 | Diab et al. |
| 6,081,735 | A | 6/2000 | Diab et al. |
| 6,083,172 | A | 7/2000 | Baker, Jr. et al. |
| 6,088,607 | A | 7/2000 | Diab et al. |
| 6,110,522 | A | 8/2000 | Lepper, Jr. et al. |
| 6,122,535 | A | 9/2000 | Kaestle |
| 6,124,597 | A | 9/2000 | Shehada |
| 6,144,868 | A | 11/2000 | Parker |
| 6,151,516 | A | 11/2000 | Kiani-Azarbayjany et al. |
| 6,152,754 | A | 11/2000 | Gerhardt et al. |
| 6,157,850 | A | 12/2000 | Diab et al. |
| 6,165,005 | A | 12/2000 | Mills et al. |
| 6,184,521 | B1 | 2/2001 | Coffin, IV et al. |
| 6,206,830 | B1 | 3/2001 | Diab et al. |
| 6,229,856 | B1 | 5/2001 | Diab et al. |
| 6,232,609 | B1 | 5/2001 | Snyder et al. |
| 6,236,872 | B1 | 5/2001 | Diab et al. |
| 6,241,683 | B1 | 6/2001 | Macklem et al. |
| 6,253,097 | B1 | 6/2001 | Aronow et al. |
| 6,256,523 | B1 | 7/2001 | Diab et al. |
| 6,263,222 | B1 | 7/2001 | Diab et al. |
| 6,278,522 | B1 | 8/2001 | Lepper, Jr. et al. |
| 6,280,213 | B1 | 8/2001 | Tobler et al. |
| 6,285,896 | B1 | 9/2001 | Tobler et al. |
| 6,321,100 | B1 | 11/2001 | Parker |
| 6,330,468 | B1 | 12/2001 | Scharf |
| 6,334,065 | B1 | 12/2001 | Al-Ali et al. |
| 6,343,224 | B1 | 1/2002 | Parker |
| 6,349,228 | B1 | 2/2002 | Kiani et al. |
| 6,360,114 | B1 | 3/2002 | Diab et al. |
| 6,368,283 | B1 | 4/2002 | Xu et al. |
| 6,371,921 | B1 | 4/2002 | Caro et al. |
| 6,377,829 | B1 | 4/2002 | Al-Ali |
| 6,388,240 | B2 | 5/2002 | Schulz et al. |
| 6,397,091 | B2 | 5/2002 | Diab et al. |
| 6,411,833 | B1 | 6/2002 | Baker, Jr. et al. |
| 6,430,525 | B1 | 8/2002 | Weber et al. |
| 6,438,399 | B1 | 8/2002 | Kurth |
| 6,463,311 | B1 | 10/2002 | Diab |
| 6,470,199 | B1 | 10/2002 | Kopotic et al. |
| 6,496,711 | B1 | 12/2002 | Athan et al. |
| 6,501,975 | B2 | 12/2002 | Diab et al. |
| 6,505,059 | B1 | 1/2003 | Kollias et al. |
| 6,515,273 | B2 | 2/2003 | Al-Ali |
| 6,519,487 | B1 | 2/2003 | Parker |
| 6,525,386 | B1 | 2/2003 | Mills et al. |
| 6,526,300 | B1 | 2/2003 | Kiani et al. |
| 6,541,756 | B2 | 4/2003 | Schulz et al. |
| 6,542,764 | B1 | 4/2003 | Al-Ali et al. |
| 6,580,086 | B1 | 6/2003 | Schulz et al. |
| 6,584,336 | B1 | 6/2003 | Ali et al. |
| 6,595,316 | B2 | 7/2003 | Cybulski et al. |
| 6,597,932 | B2 | 7/2003 | Tian et al. |
| 6,597,933 | B2 | 7/2003 | Kiani et al. |
| 6,606,511 | B1 | 8/2003 | Ali et al. |
| 6,631,281 | B1 | 10/2003 | Kastle |
| 6,632,181 | B2 | 10/2003 | Flaherty et al. |
| 6,639,668 | B1 | 10/2003 | Trepagnier |
| 6,640,116 | B2 | 10/2003 | Diab |
| 6,643,530 | B2 | 11/2003 | Diab et al. |
| 6,650,917 | B2 | 11/2003 | Diab et al. |
| 6,654,623 | B1 | 11/2003 | Kastle |
| 6,654,624 | B2 | 11/2003 | Diab et al. |
| 6,658,276 | B2 | 12/2003 | Kianl et al. |
| 6,661,161 | B1 | 12/2003 | Lanzo et al. |
| 6,671,531 | B2 | 12/2003 | Al-Ali et al. |
| 6,678,543 | B2 | 1/2004 | Diab et al. |
| 6,684,090 | B2 | 1/2004 | Ali et al. |
| 6,684,091 | B2 | 1/2004 | Parker |
| 6,697,656 | B1 | 2/2004 | Al-Ali |
| 6,697,657 | B1 | 2/2004 | Shehada et al. |
| 6,697,658 | B2 | 2/2004 | Al-Ali |
| RE38,476 | E | 3/2004 | Diab et al. |
| 6,699,194 | B1 | 3/2004 | Diab et al. |
| 6,701,170 | B2 | 3/2004 | Stetson |
| 6,714,804 | B2 | 3/2004 | Al-Ali et al. |
| RE38,492 | E | 4/2004 | Diab et al. |
| 6,721,582 | B2 | 4/2004 | Trepagnier et al. |
| 6,721,585 | B1 | 4/2004 | Parker |
| 6,725,074 | B1 | 4/2004 | Kastle |
| 6,725,075 | B2 | 4/2004 | Al-Ali |
| 6,728,560 | B2 | 4/2004 | Kollias et al. |
| 6,735,459 | B2 | 5/2004 | Parker |
| 6,745,060 | B2 | 6/2004 | Diab et al. |
| 6,760,607 | B2 | 7/2004 | Al-Ali |
| 6,770,028 | B1 | 8/2004 | Ali et al. |
| 6,771,994 | B2 | 8/2004 | Kiani et al. |
| 6,792,300 | B1 | 9/2004 | Diab et al. |
| 6,813,511 | B2 | 11/2004 | Diab et al. |
| 6,816,741 | B2 | 11/2004 | Diab |
| 6,822,564 | B2 | 11/2004 | Al-Ali |
| 6,826,419 | B2 | 11/2004 | Diab et al. |
| 6,830,711 | B2 | 12/2004 | Mills et al. |
| 6,850,787 | B2 | 2/2005 | Weber et al. |
| 6,850,788 | B2 | 2/2005 | Al-Ali |
| 6,852,083 | B2 | 2/2005 | Caro et al. |
| 6,861,639 | B2 | 3/2005 | Al-Ali |
| 6,898,452 | B2 | 5/2005 | Al-Ali et al. |
| 6,920,345 | B2 | 7/2005 | Al-Ali et al. |
| 6,931,268 | B1 | 8/2005 | Kiani-Azarbayjany et al. |
| 6,934,570 | B2 | 8/2005 | Kiani et al. |
| 6,939,305 | B2 | 9/2005 | Flaherty et al. |
| 6,943,348 | B1 | 9/2005 | Coffin, IV |
| 6,950,687 | B2 | 9/2005 | Al-Ali |
| 6,961,598 | B2 | 11/2005 | Diab |
| 6,970,792 | B1 | 11/2005 | Diab |
| 6,979,812 | B2 | 12/2005 | Al-Ali |
| 6,985,764 | B2 | 1/2006 | Mason et al. |
| 6,993,371 | B2 | 1/2006 | Kiani et al. |
| 6,996,427 | B2 | 2/2006 | Ali et al. |
| 6,999,904 | B2 | 2/2006 | Weber et al. |
| 7,003,338 | B2 | 2/2006 | Weber et al. |
| 7,003,339 | B2 | 2/2006 | Diab et al. |
| 7,015,451 | B2 | 3/2006 | Dalke et al. |
| 7,024,233 | B2 | 4/2006 | Ali et al. |
| 7,027,849 | B2 | 4/2006 | Al-Ali |
| 7,030,749 | B2 | 4/2006 | Al-Ali |
| 7,039,449 | B2 | 5/2006 | Al-Ali |
| 7,041,060 | B2 | 5/2006 | Flaherty et al. |
| 7,044,918 | B2 | 5/2006 | Diab |
| 7,067,893 | B2 | 6/2006 | Mills et al. |
| 7,096,052 | B2 | 8/2006 | Mason et al. |
| 7,096,054 | B2 | 8/2006 | Abdul-Hafiz et al. |
| 7,132,641 | B2 | 11/2006 | Schulz et al. |
| 7,142,901 | B2 | 11/2006 | Kiani et al. |
| 7,149,561 | B2 | 12/2006 | Diab |
| 7,186,966 | B2 | 3/2007 | Al-Ali |
| 7,190,261 | B2 | 3/2007 | Al-Ali |
| 7,215,984 | B2 | 5/2007 | Diab |
| 7,215,986 | B2 | 5/2007 | Diab |
| 7,221,971 | B2 | 5/2007 | Diab |
| 7,225,006 | B2 | 5/2007 | Al-Ali et al. |
| 7,225,007 | B2 | 5/2007 | Al-Ali |
| RE39,672 | E | 6/2007 | Shehada et al. |
| 7,239,905 | B2 | 7/2007 | Kiani-Azarbayjany et al. |
| 7,245,953 | B1 | 7/2007 | Parker |
| 7,254,429 | B2 | 8/2007 | Schurman et al. |
| 7,254,431 | B2 | 8/2007 | Al-Ali |
| 7,254,433 | B2 | 8/2007 | Diab et al. |
| 7,254,434 | B2 | 8/2007 | Schulz et al. |
| 7,272,425 | B2 | 9/2007 | Al-Ali |
| 7,274,955 | B2 | 9/2007 | Kiani et al. |
| D554,263 | S | 10/2007 | Al-Ali |
| 7,280,858 | B2 | 10/2007 | Al-Ali et al. |
| 7,289,835 | B2 | 10/2007 | Mansfield et al. |
| 7,292,883 | B2 | 11/2007 | De Felice et al. |
| 7,295,866 | B2 | 11/2007 | Al-Ali |
| 7,328,053 | B1 | 2/2008 | Diab et al. |
| 7,332,784 | B2 | 2/2008 | Mills et al. |

| | | |
|---|---|---|
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al-Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 2002/0077536 A1 | 6/2002 | Diab et al. |
| 2002/0128544 A1 | 9/2002 | Diab et al. |
| 2003/0036689 A1 | 2/2003 | Diab et al. |
| 2003/0088164 A1 | 5/2003 | Stetson |
| 2003/0225337 A1 | 12/2003 | Scharf et al. |
| 2004/0064020 A1 | 4/2004 | Diab et al. |
| 2004/0068164 A1 | 4/2004 | Diab et al. |
| 2004/0204636 A1 | 10/2004 | Diab et al. |
| 2004/0204637 A1 | 10/2004 | Diab et al. |
| 2004/0210146 A1 | 10/2004 | Diab et al. |
| 2004/0236196 A1 | 11/2004 | Diab et al. |
| 2005/0096517 A1 | 5/2005 | Diab et al. |
| 2005/0209517 A1 | 9/2005 | Diab et al. |
| 2006/0089549 A1 | 4/2006 | Diab et al. |
| 2006/0200016 A1 | 9/2006 | Diab et al. |
| 2006/0217609 A1 | 9/2006 | Diab et al. |
| 2007/0225581 A1 | 9/2007 | Diab et al. |
| 2007/0249918 A1 | 10/2007 | Diab et al. |
| 2007/0291832 A1 | 12/2007 | Diab et al. |
| 2008/0004514 A1 | 1/2008 | Diab et al. |
| 2008/0033266 A1 | 2/2008 | Diab et al. |
| 2008/0036752 A1 | 2/2008 | Diab et al. |
| 2008/0045823 A1 | 2/2008 | Diab et al. |
| 2009/0076400 A1 | 3/2009 | Diab et al. |
| 2009/0099430 A1 | 4/2009 | Diab et al. |
| 2009/0182211 A1 | 7/2009 | Diab et al. |

FOREIGN PATENT DOCUMENTS

| | | |
|---|---|---|
| EP | 0261 789 | 3/1988 |
| EP | 0271 340 | 6/1988 |
| EP | 0 290 273 | 11/1988 |
| EP | 0 335 357 | 3/1989 |
| EP | 0 341 327 | 11/1989 |
| EP | 0 352 923 | 1/1990 |
| EP | 0 359 206 B1 | 3/1995 |
| EP | 0 760 223 A1 | 8/1995 |
| EP | 0 761 159 B1 | 8/1996 |
| GB | 2 075 668 | 11/1981 |
| GB | 2 156 997 | 10/1985 |
| GB | 2 166 326 | 4/1986 |
| GB | 2 235 288 | 2/1991 |
| JP | 58-065137 | 4/1983 |
| JP | A-63-171539 | 7/1988 |
| JP | 3136637 | 6/1991 |
| SU | 1674798 | 9/1991 |
| WO | WO 92/15955 | 9/1992 |
| WO | WO 97/00041 | 1/1997 |
| WO | WO 98/42249 | 10/1998 |
| WO | WO 98/43071 | 10/1998 |

OTHER PUBLICATIONS

U.S. District Court, Central District of California (Western Division—Los Angeles) Civil Docket for Case #: 2:01-cv-07292-MRP-AJW.

U.S. District Court, Central District of California (Western Division—Los Angeles) Civil Docket for Case #: 2:01-cv-07293-MRP-AJW.

Complaint for Patent Infringement of US. Patent Nos. 6,206,830 B1 and 6,157,850; Demand for Jury Trial, dated Jul. 6, 2001.

First Amended Complaint for Patent Infringement of U.S. Patent Nos. 6,206,830 B1, 6,157,850 and 6,263,222 B1; Demand for Jury Trial, dated Jul. 18, 2001.

Nellcor's and Mallinckrodt's Answer to First Amended Complaint, dated Aug. 20, 2001.

Nellcor's and Mallinckrodt's Amended and Supplemental Answer and Counterclaims to Masimo Corporation's First Amended Complaint in Case No. CV-01-7292 MRP (AJWx), dated May 31, 2002.

Masimo's Reply to Nellcor's and Mallinckrodt's Amended and Supplemental Answer and Counterclaims to Masimo's First Amended Complaint in Case No. CV-01-7292 MRP (AJWx), dated Aug. 27, 2002.

Complaint for Patent Infringement of US. Patent Nos. 4,653,498, 5,078,136 and Re. 36,000, dated Nov. 17, 1999.

Defendant Masimo Corp.'s Answer and Counterclaims, dated Dec. 8, 1999.

Mallinckrodt's and Nellcor's Reply to Counterclaims of Masimo; Demand for Jury Trial, dated Dec. 28, 1999.

Mallinckrodt's and Nellcor's Amendment Complaint for Patent Infringement of U.S. Patent Nos. 4,653,498, 5,078,136, Re. 35,122 and Re. 36,000; Demand for Jury Trial, dated Jan. 24, 2000.

Defendant Masimo Corp.'s Amended Answer and Counterclaims, dated Feb. 7, 2000.

Nellcor's Reply to Amended Counterclaims of Masimo Corporation, dated Feb. 22, 2000.

Mallinckrodt's and Nellcor's Second Amended Complaint for Patent Infringement of U.S. Patent Nos. 4,621,643, 4,653,498, 4,700,708, 5,078,247, Re. 35,122 and Re. 36,000; Demand for Jury Trial, dated Oct. 13, 2000.

Masimo Corp.'s Answer to Plaintiffs' Second Amended Complaint and Counterclaims; Demand for Jury Trial, dated Nov. 2, 2000.

Mallinckrodt Inc.'s and Nellcor Puritan Bennett, Inc.'s Reply to Counterclaims of Masimo Corporation; Demand for Jury Trial, dated Dec. 1, 2000.

Nellcor's and Mallinckrodt's First Amended and Supplemental Reply and Counterclaims to Counterclaims of Masimo Corporation, dated May 31, 2002.

Masimo's Reply to Nellcor's and Mallinckrodt's First Amended and Supplemental Reply and Counterclaims to Counterclaims of Masimo, dated Aug. 27, 2002.

Nellcor's Third Amended Complaint for Patent Infringement of U.S. Patent Nos. 4,621,643, 4,653,498, 4,700,708, 5,078,136, 5,807,247 and Re. 36,000; Demand for Jury Trial, dated Jul. 31, 2002.
Masimo's Answer to Counterclaims to Nellcor's Third Amended Complaint for Patent Infringement; Demand for Jury Trial, dated Aug. 27, 2002.
Complaint for Patent Infringement of U.S. Patent No. 5,490,505; Demand for Jury Trial, dated Oct. 8, 1999, entered Oct. 15, 1999.
Mallinckrodt's and Nellcor's Answer and Counterclaims, dated Nov. 1, 1999.
Plaintiff's Masimo Corp.'s Reply to Defendants' Counterclaims, dated Nov. 22, 1999.
Amended Complaint for Patent Infringement of U.S. Patent Nos. 5,490,505 and 6,036,642; Demand for Jury Trial, dated Apr. 5, 2000, entered Apr. 18, 2000.
Answer to First Amended Complaint and Amended Counterclaim; Demand for Jury Trial, dated May 1, 2000.
Plaintiff Masimo Corp.'s Reply to Defendants' First Amended Counterclaims; Demand for Jury Trial, dated May 18, 2000.
Nellcor's and Mallinckrodt's Amended and Supplemental Answer to Counterclaims to Masimo Corporation's First Amended Complaint in Case No. CV-01-7293-MRP (AJWx), dated 5/31/02.
Masimo's Reply to Nellcor's and Mallinckrodt's Amended and Supplemental Answer and Counterclaims to Masimo's First Amended Complaint in Case No. -01-7293 MRP (AJWx), dated Aug. 27, 2002.
Memorandum of Decision re: Mallinckrodt and Nellcor's Motion for Summary Judgement of Invalidity of Claim 19 of U.S. Patent No. 5,490,505.
Minute Order 1) Granting Defendants' Motion for Summary Judgment of Non-Infringement of '642 Patent; 2) Denying Plaintiffs Motion for Preliminary Injunction; 3) Granting Plaintiffs Ex Parte Application to Strike Defendants' Supplemental Declaration, dated Oct. 4, 2000, entered Oct. 6, 2000.
Defendant's Mallinckrodt's and Nellcor's Statement of Uncontroverted Facts and Conclusions of Law.
Findings of Fact and Conclusions of Law Regarding Masimo's Motion for Preliminary Injunction.
Judgement in Masimo Corp. v. Mallinckrodt Inc., Court of Appeals for the Federal Circuit No. 01-1038, dated Aug. 8, 2001, entered Oct. 17, 2001.
Memorandum of Decision and Order Re: 1) Claim Construction; 2) Motion to Strike Masimo's Declarations, entered Feb. 27, 2003.
Final Judgment, entered Aug. 6, 2004.
Memorandum of Decision and Order Re: Post-Trial Motions, dated Jul. 12, 2004, entered Jul. 14, 2004.
Memorandum and Points and Authorities in Support of Mallinckrodt's and Nellcor's Motion for Summary Judgment of Invalidity of Claim 19 of U.S. Patent No. 5,490,505, dated Aug. 30, 2000.
Masimo's Opposition to Defendants' Motion for Summary Judgment for Summary Judgment of Invalidity of Claim 19 of U.S. Patent No. 5,490,505, dated Sep. 21, 2000.
Reply Memorandum and Points and Authorities in Support of Mallinckrodt's and Nellcor's Motion for Summary Judgment of Invalidity of U.S. Patent No. 5,490,505, dated Oct. 13, 2000.
Brief of Plaintiff-Appellant Masimo Corporation, dated Dec. 8, 2000.
Non-Confidential Brief of Defendants-Cross Appellants Mallinckrodt inc and Nellcor Puritan Bennett, Inc., dated Jan. 22, 2001.
Nonconfidential Reply Brief of Plaintiff-Appellant Masimo Corporation, dated Feb. 6, 2001.
Masimo Corp.'s Initial Claim Construction on Its Asserted Patents, dated Jun. 21, 2002.
Declaration of Jack Goldberg in Support of Masimo Corp.'s Initial Claim Construction on Its Asserted Patents, dated Jun. 21, 2002.
Notice of Errata and Corrected Appendices for Mallinckrodt's and Nellcor's Statement Regarding Disputed Claim Terms of the Asserted Patents, dated Sep. 12, 2002 (Final Version).
Expert Declaration of Robert T. Stone Re: Masimo's Patent-In-Suit, dated Jul. 18, 2002.
Masimo Corp.'s Opening Memorandum of Claim Construction, dated Sep. 16, 2002.
Nellcor's and Mallinckrodt's Opening Claim Construction Brief on the Patent-In-Suit, dated Sep. 16, 2002.
Masimo Corp.'s Reply Memorandum on Claim Construction, dated Oct. 18, 2002.
Nellcor's and Mallinckrodt's Reply Claim Construction Brief on the Patents-In-Suit, dated Oct. 18, 2002.
Nellcor's Trial Brief on Indefiniteness, dated Mar. 23, 2004.
Masimo's Trial Brief of Indefiniteness, dated Mar. 24, 2004.
Nellcor's Trial Brief re Inequitable Conduct, dated Mar. 23, 2004.
Masimo's Trial Brief regarding Inequitable Conduct, dated Mar. 24, 2004.
Nellcor's Memorandum of Points and Authorities in Support of: (1) Argument on Bench Trial and (2) Renewed Motion for Judgment as a Matter of Law or Alternatively, a New Trial.
Masimo's Memorndum of Points and Authorities in Opposition to Nellcor's (1) ,Argument on Bench Trial and (2) Renewed Motion for Judgment as a Matter of Law or for a New Trial.
Memorandum of Points and Authorities in Support of Masimo's Motion for (1) Judgment as a Matter of Law that Nellcor Literally Infringes Claim 17 of the '850 Patent and Claims 16 and 23 of the '222 Patent; (2) A Permanent Injunction; (3) An Accounting for Infringing Sales Occurring in 2004; and (4) Prejudgment Interest.
Nellcor's Opposition to Masimo's Motion for Judgment as a Matter of Law and Other Post-Trial Issues.
Brief of Defendant-Appellant Masimo Corporation.
Confidential Brief of Plaintiffs-Cross Appellants Mallinckrodt, inc. and Nellcor Puritan Bennett, Inc.
Letter to Mr. Hornbaly, Clerk of Fed. Cir., indicating that the parties agreed that the Confidential Brief (Ref. No. 106) do not need to remain confidential.
Reply Brief of Defendant-Appellant Masimo Corporation.
Reply Brief of Plaintiffs-Cross Appellants Mallinckrodt, Inc. and Nellcor Puritan Bennett, Inc.
Nellcor's Response to Masimo's First Set of Interrogatories in the Consolidated Case to Mallinckrodt Inc. and Nellcor Puritan Bennett, Inc. (Nos. 1-8), dated Aug. 23, 2002.
Nellcor's Supplemental Response to Masimo's First Set of Interrogatories in the Consolidated Case (No. 2), dated Jun. 24, 2003.
Nellcor's Revised and Corrected Supplemental Response to Masimo's First Set of Interrogatories in the Consolidated Case (No. 2), dated Jun. 25, 2003.
Service Manual: Nellcor-100 Pulse Oximeter, 5 button model, Copyright 1993.
J. Corenman Computation Notebook, marked Jun. 23, 1982-Jun. 22, 1983.
B. Widrow & S. Stearns, "Adaptive Signal Processing," Prentice-Hall, Copyright 1985.
N-100 Source Code, Copyright 1983-86.
N-100, Source Code, Copyright 1976-87.
"Welcome to the World of Nellcor Pulse Oximetry," Nellcor brochure, in 16 pages, undated.
"Oximax, Sensor Conversion Step," Nellcor brochure, copyright 1997.
"Motion-tolerant $SpO_2$," Philips brochure, undated.
"Introducing New Hand-Held Digital Pulse Oximeter and Sensor with Patented Technologies," Philips, printed from internet site "http://www.oximetersonline.com", 1 page.
"Novametrix Announces FDA Clearance of New Pulse Oximeter," Mar. 2, 2000 Press release in 2 pages.
"Detax-Ohmeda Announces New Products at the American Society of Anesthesiologist, New Orleans," downloaded from internet in 3 pages.
"OSI Systems Announces FDA 510k Approval of First All Digital Pulse Oximeter Monitor," showing date of Apr.. 23, 2001 in 2 pages.
Alaris Medical Systems, "Summary of Safety and Effectiveness" in 3 pages.
Letter to Alaris Medical Systems from Dept. of Health & Human Services, showing date of Sep. 11, 2002 in 3 pages.
BCI 510(k) FDA Submission 2000-2002.
Datex-Ohmeda 510(k) FDA Submission 2000-2002.
Dolphin 510(k) FDA Submission 2002.

Fukuda Denshi 510(k) FDA Submission 2001.
Nellcor Puritan Bennett 510(k) FDA Submission 1999-2002.
Nonin Medical 510(k) FDA Submission 2000.
OSI Medical 510(k) FDA Submission 2001.
Siemens Medical 510(k) FDA Submissions 2002.
SIMS BCI, Inc. 510(k) FDA Submissions 2001.
"Nellcor's Next Great Move Undated, Pulse Oximetry with ECG Synchronization . . . for Reduced Artifact," undated.
Operator's Manual, Nellcor N-200 Pulse Oximeter, Copyright 1987.
C. Baker; "Design Summary and Evaluation of Saturation Arbitrator," undated.
C. Baker & T. Yorkey, "Two Wavelength Saturation Algorithms," dated Sep. 14, 1994.
N-200 Oximeter Summary Sheets, Design History Records, dated Jul. 1987-Oct. 1987.
PcSat Source Code.
Directory listing and source code for Decsub, dated 1991-1992.
Nellcor engineering order #1104 re N-100 C/D program assy, listing a date of Mar. 3, 1986.
Arye Nehorai, "A Minimal Parameter Adaptive Notch Filter With Constrained Poles and Zeros," IEEE Transactions on Acoustics, Speech and Signal Processing, vol. ASSP-22 No. 4, Aug. 1985.
Nehorai, Arye, "Adaptive Comb Filtering for Harmonic Signal Enhancement," IEEE Transaction of Acoustics, Speech and Signal Processing, Oct. 1986.
Hendry, S.D., "Computation of Harmonic Comb Filter Weights," IEEE Transactions on Signal Processing, Apr. 1993.
C. Baker & T. Yorkey, "O4 Summary" Nellcor, listing a date of Aug. 5, 1994.
M. Jopling, P. Mannheimer & D. Bebout; "Issues in the Laboratory Evaluation of Pulse OxiMeter Performance"; Anesthesia & Analgesia, vol. 94, Copyright 2001.
Nellcor Engineering Order, listing date of Mar. 15, 1989.
Nellcor's Sales & Shipment Records Mar. 1989 to Mar. 1990.
C. Baker and T. Yorkey, "O4 Two Wavelength Saturation Algorithms," listing date of Sep. 14, 1994.
Declaration of Clark R. Baker, dated Aug. 15, 2000.
Declaration of Thomas J. Yorkey, dated Aug. 20, 2000.
P. Mannheimer and D. Bebout, "A Critical Review of Motion in Pulse Oximetry," undated.
Tobin, Pologe and Batchelder, "A Characterization of Motion Affecting Pulse Oximetry in 350 Patients,"Anesthesia & Analgesia, vol. 94, Copyright 2001.
R. Brown and P. Hwang, "Introduction to Random Signals and Applied Kalman Filtering," 2nd Ed., John Wiley & Sons, Inc., New York, Copyright 1992.
IEEE 100, "The Authoritative Dictionary of IEEE Standards Terms," 7th ed., IEEE Press Publications, Copyright 2000.
Haykin, S., "Adaptive Filter Theory," 1st ed., Prentice-Hall, Inc., 1986.
Haykin, S., "Adaptive Filter Theory," 2d ed., Prentice-Hall, Inc., 1991.
Clark R. Baker and Thomas J. Yorkey, "Calculation of Pulse Rate in Pulse Oximetry," dated Oct. 4, 1993.
Clark R. Baker and Thomas J. Yorkey, "A Proposal for PostProcessing and Display for 04 Saturation and Pulse-Rate Algorithms," dated Oct. 4, 1993.
Description of PCSat; dated Oct. 16, 1991.
Corresponding Source Code.
Pulse Oximetry The Next Generation, dated Dec. 7, 1992.
Flewelling, Ross, "Oximetry Technology: Strategies for New Development," listing date of Feb. 1995.
"Safety Monitoring in the Regular Inpatient Care Area—National Sales Meeting," listing date of 1992.
Swedlow, "Pulse Oximetry," undated.
Five Generations of Nellcor Oximetry, undated.
Letter from T. Ulatowski (FDA) to G. To (Nellcor Puritan Bennett, Inc.) with Nellcor 510(K) enclosures, dated Sep. 24, 2002.
"Technology Development Projects," Dec. 1991.
Next Generation Oximeter Handwritten notes.
Yorky, T., "Signal Processing Technology Development Projects—Fall 92," listing date of Nov. 5, 1992.

Yorky, T., "Multiple Time Samples in Pulse Oximetry," listing date of Oct. 14, 1992.
"Potential Areas for New Technology Development—Nellcor—1992," listing date of Sep. 1, 1992.
Source Code.
Carleton, Penny M., et al. Assessment of Effectiveness of Flexible Monitoring System for Non-ICU Transitional Patients, 1998.
M. Jopling, P. Mannheimer & D. Bebout, "Issues in the Laboratory Evaluation of Pulse Oximeter Performance," STA-ISLAPO Meeting Supplement, pp. S62-S68, Copyright 2001.
N-595 Combined motion and low perfusion study, undated.
Saturation Arcana.
Memo from C. Baker to T. Yorkey re: "Pulse Oximetry Next Generation (PONG)," dated Dec. 7, 1992.
T. Yorkey Computation Book, listing dates of Mar. 12, 1993-Nov. 5, 1994.
Sayed et al., "A State-Space Approach to Adaptive RLS Filtering," IEEE Signal Processing Magazine, Jul. 1994.
Nellcor brochure for N-395 Pulse Oximeter with Oxismart XL and SatSeconds, undated.
N-395 Pulse Oximeter Brochure, undated.
OxiMax N595 Pulse Oximeter Service Manual, undated.
O4 Software 1994 Technology Devel. Dept., listing date of Oct. 4, 1994.
Barker S, "Motion Resistant Pulse Oximetry: Comparison of New and Old Models," Anesthesia and Analgesia, 2002; 95: 967-972.
Barker SJ, Shah NK, "The Effects of Motion on the Performance of Pulse Oximeters in Volunteers," Anesthesiology, 1997; 86(1): 101-108.
OEM 601 Module-Dolphin ONE Products, undated.
Dolphin Medical Integration Manual, OEM-601 Module, listing date of Dec. 16, 2002.
Datex—Ohmeda News Flash—TruTrak+ technology provides improved SpO2 readings during clinical patient motion, dated Oct. 16, 2002.
Novametrix Pulse Oximetry Program; Presented to Sisters of St. Joseph of Orange, undated.
"Motion-tolerant SpO2 with maximum choice," Philips, undated.
"Probe," Agilent Technologies, Winter 2001.
"CMS 2002 Acute Care Patient Monitoring System," Philips, undated.
Viridia CMS 2000 Product Information, Agilent, New SpO2 Algorithm, undated.
Richard G. Aseltine, Jr., Siegfried Kaestle, Ph.D. and Rolf Neumann, "New Motion Resistant SpO2-Algorithm by Frequency Domain Signal Analysis," Agilent Technologies, undated.
510(k) Notification; Infinity MicrO2 + Pulse Oximeter, dated Jul. 23, 2002.
Tremper KK, Barker SJ., "Pulse Oximetry," Anesthesiology 1989:70:98-108.
Baker and Yorkey, Nellcor O4 Algorithm Summary, undated.
Letter to FDA re 510(k) N-200 Labeling Modification, dated Sep. 23, 2002.
Baker, 04 Software Technology Development Department, listing date of 1994.
IEEE Transactions on Acoustics, Speech, and Signal Processing, dated Apr. 1983.
Alan S. Willsky, "Digital Signal Processing and Control and Estimation Theory: Points of Tangency, Areas of Intersection, and Parallel Directions," dated 1979.
Nellcor Requirements, Marketing Product, MP 404, listing date of Aug. 22, 1995.
Flexible Monitoring Clinical Environment, listing date of 1992.
Trial Transcript in *Masimo Corporation* v. *Mallinckrodt, Inc., et al*, CV 99-1245-AHS, Sep. 25, 2000 (pp. 1-50).
Trial Transcript in *Mallinckrodt, Inc., et al* v. *Masimo Corporation*, CV 00-6506 MRP, Feb. 18, 2004 (pp. 1-111).
Trial Transcript in *Mallinckrodt, Inc., et al* v. *Masimo Corporation*, CV 00-6506 MRP, Feb. 19, 2004 (pp. 112-235).
Trial Transcript in *Mallinckrodt, Inc., et al* v. *Masimo Corporation*, CV 00-6506 MRP, Feb. 20, 2004 (pp. 237-320).
Trial Transcript in *Mallinckrodt, Inc., et al* v. *Masimo Corporation*, CV 00-6506 MRP, Feb. 23, 2004 (pp. 427-625).

Trial Transcript in *Mallinckrodt, Inc., et al v. Masimo Corporation*, CV 00-6506 MRP, Feb. 24, 2004 (pp. 626-806).
Trial Transcript in *Mallinckrodt, Inc., et al v. Masimo Corporation*, CV 00-6506 MRP, Feb. 25, 2004 (pp. 807-902).
Trial Transcript in *Mallinckrodt, Inc., et al v. Masimo Corporation*, CV 00-6506 MRP, Feb. 2, 2004 (pp. 943-1128).
Trial Transcript in *Mallinckrodt, Inc., et al v. Masimo Corporation*, CV 00-6506 MRP, Feb. 27, 2004 (pp. 1214-1281).
Trial Transcript in *Mallinckrodt, Inc., et al v. Masimo Corporation*, CV 00-6506 MRP, Mar. 1, 2004 (pp. 1282-1469).
Trial Transcript in *Mallinckrodt, Inc., et al v. Masimo Corporation*, CV 00-6506 MRP, Mar. 2, 2004 (pp. 1470-1617).
Trial Transcript in *Mallinckrodt, Inc., et al v. Masimo Corporation*, CV 00-6506 MRP, Mar. 3, 2004 (pp. 1618-1795).
Trial Transcript in *Mallinckrodt, Inc., et al v. Masimo Corporation*, CV 00-6506 MRP, Mar. 4, 2004 (pp. 1796-1986).
Trial Transcript in *Mallinckrodt, Inc., et al v. Masimo Corporation*, CV 00-6506 MRP, Mar. 5, 2004 (pp. 1987-2145).
Trial Transcript in *Mallinckrodt, Inc., et al v. Masimo Corporation*, CV 00-6506 MRP, Mar. 8, 2004 (pp. 2146-2346).
Trial Transcript in *Mallinckrodt, Inc., et al v. Masimo Corporation*, CV 00-6506 MRP, Mar. 9, 2004 (pp. 2347-2528).
Trial Transcript in *Mallinckrodt, Inc., et al v. Masimo Corporation*, CV 00-6506 MRP, Mar. 10, 2004 (pp. 2529-2663).
Trial Transcript in *Mallinckrodt, Inc., et al v. Masimo Corporation*, CV 00-6506 MRP, Mar. 11, 2004 (pp. 2664-2801).
Trial Transcript in *Mallinckrodt, Inc., et al v. Masimo Corporation*, CV 00-6506 MRP, Mar. 15, 2004 (pp. 2802-2860).
Trial Transcript in *Mallinckrodt, Inc., et al v. Masimo Corporation*, CV 00-6506 MRP, Mar. 16, 2004 (pp. 2861-3036).
Trial Transcript in *Mallinckrodt, Inc., et al v. Masimo Corporation*, CV 00-6506 MRP, Mar. 17, 2004 (pp. 3037-3244).
Trial Transcript in *Mallinckrodt, Inc., et al v. Masimo Corporation*, CV 00-6506 MRP, Mar. 18, 2004 (pp. 3245-3416).
Trial Transcript in *Mallinckrodt, Inc., et al v. Masimo Corporation*, CV 00-6506 MRP, Mar. 19, 2004 (pp. 3417-3515).
Trial Transcript in *Mallinckrodt, Inc., et al v. Masimo Corporation*, CV 00-6506 MRP, Mar. 22, 2004 (pp. 3603-3715).
Trial Transcript in *Mallinckrodt, Inc., et al v. Masimo Corporation*, CV 00-6506 MRP, Mar. 23, 2004 (pp. 3716-3828).
Trial Transcript in *Mallinckrodt, Inc., et al v. Masimo Corporation*, CV 00-6506 MRP, Mar. 24, 2004 (pp. 3829-3983).
Trial Transcript in *Mallinckrodt, Inc., et al v. Masimo Corporation*, CV 00-6506 MRP, Mar. 25, 2004 (pp. 3984-4054).
Hearing Transcript in *Mallinckrodt, Inc., et al v. Masimo Corporation*, CV 00-6506 MRP, Dec. 16, 2002-Dec. 17, 2002.
Hearing Transcript in *Mallinckrodt, Inc., et al v. Masimo Corporation*, CV 00-6506 MRP, Jun. 18, 2004.
Blitt, M.D., Casey D., "Monitoring in Anesthesia and Critical Care Medicine," Monitoring and Patient Safety, Second Edition, Chapter 4, pp. 33-48, 1990.
Widrow, B., "Adaptive Signal Processing," Prentice Hall, Englewood, NJ, 1985.
Yelderman, M., et al. "ECG Enhancement by Adaptive Cancellation of Electrosurgical Interference," IEEE Transactions on Biomedical Engineering, vol. BME-30 No. 7, Jul. 1983.
Rearden, Jr., R.S., et al., "Biomedical Sciences Instrumentation," Some Digital Signal Processing Methods for Detecting Fat Particles in Blood, vol. 12, pp. 47-50, 1976.
"Nellcor N-100 And N-10 Pulse Oximeters, Plus Interchangeable Sensors," undated.
"Nellcor Redefines Pulse Oximetry. Introducing the Nellcor N-200 with ECG Synchronization," undated.
W. Byrne, P. Flynn, R. Zapp & M. Siegel, "Adaptive Filter Processing in Microwave Remote Heart Monitors," IEEE Transactions on Biomedical Engineering, vol. BME-33, No. 7, pp. 717-726, Jul. 1986.
J. Giolma, "Defining Respiratory Epochs Using an Adaptive AR Filter," ISA Paper #89-0236, pp. 227-232, 1989.
R. Jane, P. Laguna, P. Caminal & H. Rix, "Adaptive Filtering of High-Resolution ECG Signals," IEEE Proceedings, Computers in Cardiology, pp. 347-350, Sep. 23-26, 1990.

T. Kao, K. Wu, B. Yu & J. Hung, "Digital Signal Enhancement of the Abdominal Fetal ECG," IEEE Engineering in Medicine & Biology Society 11th Annual Int'l Conf., 1989.
P. Hamilton & W. Tompkins, "Adaptive Matched Filtering for QRS Detection," IEEE Engineering in Medicine & Biology Society 10th Annual Int'l Conf., 1988.
Y. Park, B. Cho, N. Kim, W. Kim S. Park & D. Youn, "A Fetal ECG Signal Monitoring System Using Digital Signal Processor," ISCAS'88, pp. 2391-2394, 1988.
L. Lum & P. Cheung, "Evaluation of Pulse Oximetry with EKG Synchronization," IEEE Engineering in Medicine & Biology Society 10th Annual Int'l Conf., Nov. 4-7, 1988.
K. Lin & W. Chang, "Adaptive Noise Reduction for Pulmonary Artery Blood Pressure," IEEE Engineering in Medicine & Biology Society 10th Annual Int'l Conf., Nov. 4-7, 1988.
M. Ogino, "The Advantages of a New Technology Pulse Oximeter in Neonatal Care," Neonatal Intensive Care, 2002 Abstract No. 36.
"Masimo Current News," printed from Internet site www.masimo.com/news/news.htm on or around Aug. 9, 2000.
Chapter 6: The LMS Algorithm, Adaptive Algorithms and Structure Part III, undated.
"Nellcor N-200 Leads Beyond Pulse Oximetry," undated.
Operator's Manual—Nellcor N-200 Pulse Oximeter; 1992.
"N-200 Pulse Oximeter with C-Lock ECG Synchronization," undated.
D.P. Brown, "Evaluation of Pulse Oximeters using Theoretical Models and Experimental Studies," University of Washington, Nov. 24, 1987.
Braun, S., et al., "*Mechanical Signature Analysis—Theory and Applications*," pp. 142-145, 202-203 (1986).
Ferrara, E. R., "*Fetal Electrocardiogram Enhancement by Time-Sequenced Adaptive Filtering*", IEEE Transactions on Biomedical Engineering, vol. BME-29, No. 6, Jun. 1982.
Glover, Jr., J. R., "*Adaptive Noise Canceling of Sinusoidal Interferences*," A Dissertation Submitted to the Department of Electrical Engineering and the Committee on Graduate Studies of Stanford University in Partial Fulfillment of the Requirements for the Degree of Doctor of Philosophy, pp. iii-82 (1975).
Harris, et al., "*Digital Signal Processing with Efficient Polyphase Recursive All-Pass Filters*," International Conference, Florence, Italy, (Sep. 4-6, 1991).
Hendry, S. D., "*Computation of Harmonic Comb filter Weights*", IEEE Transactions on Signal Procesing, vol. 41, No. 4, Apr. 1993.
Li, G., "*A Stable and Efficient Adaptive Notch Filter for Direct Frequency Estimation*", IEEE Transactions on Signal Processing, vol. 45, No. 8, Aug. 1997.
Nehorai, A., "*Adaptive Comb Filtering for Harmonic Signal Enhancement*", IEEE Transactions on Acoustics, Speech, and Signal Processing, vol. ASSP-34, No. 5, Oct. 1986.
Nehorai, A., "*A Minimal Parameter Adaptive Notch Filter With Constrained Poles and Zeros*", IEEE Transactions On Acoustics, Speech, and Signal Processing, vol. ASSP-33, No. 4, Aug. 1985.
Pau, L. F., "*Acoustic and Vibration Monitoring,*" Failure Diagnosis and Performance Monitoring, Chapter 13, pp. 295-299.
Severinghaus, M.D., J. W., "*Pulse Oximetry Uses and Limitations*,"pp. 104, ASA Convention, New Orleans (1989).
Strobach, P., "*Single Section Least Squares Adaptive Notch Filter*", IEEE Transactions on Signal Processing, vol. 43, No. 8, Aug. 1995.
Widrow, B., *Adaptive Noise Cancelling: Principles and Applications:, Proceedings of the IEEE*, vol. 63, No. 12, Dec. 1975.
Wukitsch, M., W., et al., "*Pulse Oximetry: Analysis of Theory, Technology, and Practice*", Journal of Clinical Monitoring, vol. 4, No. 4, pp. 290-301 (Oct. 1988).
Yelderman, M., et al., "*Ecg Enhancement by Adaptive Cancellation of Electrosurgical Interference*,"pp. 1-21.
Yelderman, M., et al., "*Sodium Nitroprusside Infusion by Adaptive Control*", Adaptive Control vby Inverse Modeling, Conference Record: $12^{th}$ Asilosor Conference 90 (1978).
Yu, C., et al., "*Improvement in Arterial Oxygen Control Using Multiple Model Adaptive Control Procedures*," pp. 878-883.
United States District Court—Civil Minutes, Case No. SA CV 99-1245 AHS (Anx), *Masimo v. Mallinckrodt and Nellcor Puritan Bennett*, Dated: Oct. 4, 2000.

United States Court of Appeals for the Federal Circuit—Opinion, Case No. 01-1038,-1084, *Masimo v. Mallinckrodt, Inc. and Nellcor Puritan Bennett, Inc.*, Decided: Aug. 8, 2001.

Findings of Fact and Conclusions of Law Regarding Masimo's Motion for Preliminary Injunction, *Masimo v. Mallinckrodt inc.*, et al., U.S. District Court, Central District of California (Southern Division), Civil Action No. SA-CV-99-1245 AHS (Anx), filed Nov. 3, 2000 (Redacted).

Nellcor's Third Amended Complaint for Patent Infringement.

Nellcor's and Mallinckrodt's Amended and Supplemental Answer and Counterclaims to Masimo Corporation's First Amended Complaint in Case No. CV-01-7293-MRP (AJWx).

Nellcor's and Mallinckrodt's Amended and Supplemental Answer and Counterclaims to Masimo Corporation's First Amended Complaint in Case No. CV-01-7292-MRP (AJWx).

Nellcor's and Mallinckrodt's First Amended and Supplemental Reply and Counterclaims to Counterclaims of Masimo Corporation.

Non-Confidential Reply Brief of Defendants-Cross Appellants Mallinckrodt Inc. and Nellcor Puritan Bennett, Inc. dated Feb. 22, 2001.

Nellcor's and Mallinckrodt's Reply Claim Construction Brief on the Patents-In-Suit dated Oct. 18, 2002.

Nellcor's and Mallinckrodt's Opening Claim Construction Brief on the Patents-In-Suit dated Sep. 16, 2002.

Non-Confidential Brief of Defendants-Cross Appellants Mallinckrodt Inc. and Nellcor Puirtan Bennett, Inc. dated Jan. 22, 2001.

Non-Confidential Brief of Plaintiff-Appellant Masimo Corporation dated Dec. 8, 2000.

Non-Confidential Reply Brief of Plaintiff-Appellant Masimo Corporation dated Feb. 6, 2001.

Memorandum of Decision and Order Re: Claim Construction; Motion to Strike Masimo's Declarations dated Feb. 27, 2003.

International Search Report, App. No.: PCT/US 93/09064, App. Date Jan. 13, 1994, 3 pages.

Supplemental Response to Plaintiff Masimo's First Set of Interrogatories to Defendant Mallinckrodt Inc. Pursuant to FED.R.CIV.P. 26(e).

Nellcor's Second Supplemental Response to Masimo's First Set of Interrogatories in Consolidated Case (No. 2), dated Jul. 14, 2003.

Addendum to Nellcor's Second Supplemental Response to Masimo's First Set of Interrogatories in the Consolidated Case (No. 2), dated Jul. 15, 2003.

Second Addendum to Nellcor's Second Supplemental Response to Masimo's First Set of Interrogatories in the Consolidated Case (No. 2), dated Aug. 10, 2003.

Third Addendum to Nellcor's Second Supplemental Response to Masimo's First Set of Interrogatories in the Consolidated Case (No. 2), dated Aug. 13, 2003.

Nellcor's Oct. 13, 2003 Supplemental and Revised Response to Masimo's First Set of Interrogatories in the Consolidated Case (No. 2), dated Oct. 13, 2003.

U.S. States Court of Appeals for the Federal Circuit, Opinion, decided Sep. 7, 2005.

"A More Reliable Approach for Deriving SpO2 and Pulse Rate," Agilent Technologies, Aug. 2000, pp. 1-2.

"FAST-Sp02 Motion-tolerant pulse oximetry with maximum sensor flexibility," Phillips Medical Systems, pp. 1-2, 2003.

"Product Information Fast-Sp02 Measurement," Agilent Technologies, printed from http://www.healthcare.agilent.com/cms_update/product_information/sp02.html on Feb. 15, 2001, pp. 1-2.

A. Cohen et al., "A Light Emitting Diode Skin Reflectance Oximeter," Medical & Biological Engineering, Journal of the International Federation for Medical and Biological Engineering, vol. 10, pp. 385-391, cover page, acknowledgement page, Total pages 12, 1972.

Deborah S. Bland, RN, "Pulse Oximetry, Monitoring Arterial Hemoglobin Oxygen Saturation," Aorn Journal, Apr. 1987, vol. 45, No. 4, pp. 964-967, cover page, gen info page, Total pages 5.

Doblar, D.O. et al., "Dynamic Characteristics of Cerebral Blood Flow Response to Sinusoidal Hypoxia," American Physiological Society, 1979, pp. 721-729.

E. M. Sevick et al., "Quantitation of Time- and Frequency-Resolved Optical Spectra for the Determination of Tissue Oxygenation," Analytical Biochemistry 195, pp. 330-351.

F.F. Jobsis, "Noninvasive, Infrared Monitoring of Cerebral and Myocardial Oxygen Sufficiency and Circulatory Parameters," Science, vol. 198, No. 4323, Dec. 23, 1977, pp. 1264-1267, table of contents pages (2), Total pages 6.

Farid U. Dowla et al., "Neural Networks and Wavelet Analysis in the Computer Interpretation of Pulse Oximetry Data," pp. 527-536, 1996, Oct. 29, 1990.

Fast-SpO2 Pulse oximetry, printed from http://www.medical.philips.com/main/products/patient_monitoring/products/fast_spo2/in... on Oct. 30, 2006, pp. 1-3.

Felix W. Leung, MD. et al., "Gastroduodenal mucosal hemodynamics by endoscopic reflectance spectrophotometry," Gastrointestinal Endoscopy, 1987, vol. 33, No. 4, Aug. 1987, pp. 284-288, table of contents page, Total pages 6.

H.S. Lim et al., "The Study of Signal Processing Method in Frequency Domain for Measuring Oxygen Saturation in Biological Tissue," pp. 527-530, 2000.

Hanson, P.G. et al., "Influence of Breathing Pattern on Oxygen Exchange During Hypoxia and Exercise," Journal of Applied Physiology, Jun. 1975, vol. 38, No. 6.

Hiramoto, J. et al., "Tissue Spectrum Analyzer for Medical Use," Review of Laser Engineering, 1985, vol. 13, No. 2, pp. 165-170.

J.C. Dorlas et al., "Pulse Oximetry—principles and first experiences during anesthesia," Acta Anaesthesiologica Belgica, 1987, 38, No. 2. pp. 133-138,Cover page, table of contents pp. 1-4, Total pp. 10.

J.M. Kim, et al., "Signal Processing Using Fourier & Wavelet Transform for Pulse Oximery," pp. 310-311.

Joachim S. Gravestein, MD., "Sampling Intervals for Clinical Monitoring of Variables During Anesthesia," Journal of Clinical Monitoring, vol. 5. No. 1. Jan. 1989, pp. 17-21, cover page, Total pp. 6.

Joseph M. Schmitt et al., "An Integrated Circuit-Based Optical Sensor for In Vivo Measurement of Blood Oxygenation," IEEE Transactions on Biomedical Engineering, vol. BME-33, No. 2, Feb. 1986, pp. 98-107.

Kamata, T. et al., "In Vivo Analysis of Hepatic Hemodynamics by Reflectance Spectrophotometry," Kan, Tan, Sui, 1986, vol. 12, No. 5, pp. 725-730.

Karen Riedel, RN, "Pulse oximetry: A new thechnology to assess patient oxygen needs in the neonatal intensive care unit", The Journal of Perinatal and Neonatal Nursing, Jul. 1987, pp. 49-57, cover pages, Total pp. 11.

Kent K. Gillingham et al., "Transfer Functions for Arterial Oxygen Saturation During +Gz Stress," Aviation Space and Environmental Medicine, vol. 46, No. 11. Nov. 1975, pp. 1329-1335.

Leon Bennett, Mae, "Spectrum Analysis of Large Toe Plethysmographic Waveshape," Arch Phys Med. Rehabil. vol. 66, May 1985, pp. 280-285.

Lisbet Jansson et al., "Noise Reduction of ECG by Averaging—an Experimental Study of the Procedure and a Validated Method," pp. 781-787, 1975.

Lloyd A. Marks, "Digital Enhancement of the Peripheral Admittance Plethysmogram," IEEE Transactions on Biomedical Engineering, vol. BME-34, No. 3, Mar. 1987, pp. 192-198.

M. Brunner et al., "Some Aspects of Signal Analysis Applied to Intracapillary Hemoglobin Spectra," pp. 803-810.

M. Brunner, "Measurements and Processing of Intracapillary Hemoglobin Spectra by Using a Micro-Lightguide Spectrophotometer in Connection with A Microcomputer," pp. 909-916.

M.B. Taylor et al., "The current status of pulse oximetry—Clinical value of continuous noninvasive oxygen saturation monitoring," Anesthesia, 1986, vol. 41, pp. 943-949, Contents page, Total pp. 8.

Makino,'M. et al., "Spectrophotometric Detennination of Oxygen Saturation in Blood," The Japanese Journal of Clinical Pathology, 1986, vol. 16, No. 8, pp. 647-650.

Matthew James Hayes et al., "A New Method for Pulse Oximetry Possessing Inherent Insensitivity to Artifact," IEEE Transactions on Biomedical Engineering, vol. 48, No. 4., Apr. 2001, pp. 452-461.

Michael W. Wukitsch et al., "Knowing Your Monitoring Equipment," Journal of Clinical Monitoring, vol. 4. No. 4, Oct. 1988, pp. 290-301, cover page, Total pp. 13.

Min, B.G., et al., "*Frequency-Domain Analysis of Oxygen Stores During Hypoxia in the Goat*," Annals of Biomedical Engineering, vol. 6 No. 4, Received Jul. 1, 1978.

R. Pahl et al., "Reflectance Spectrometry in Whole Blood Using a CCD Array Camera Part 1: Haematocrit Independent Measurement of Oxygen Saturation with the Aid of a New Evaluating Method," Biomed. Technik 33 (1988), pp. 240-246.

Rabiner, L.R. et al., "The Chirp z-Transform Algorithm and Its Application," Bell System Technical Journal, May-Jun. 1969, vol. 48, No. 5, pp. 1249-1292.

Radda, G.K. et al, "Recent Studies on Cellular Metabolism by Nuclear Magnetic Resonance," Annual Review of Physiology, 1979, vol. 41, pp. 749-769.

Razieh Semnani et al., "Quantitative evaluation of arterial pulsatile flow and pressure, applying impedance plethysmography to a human arterial model incorporating anatomical branching and scale," Computer Methods and Programs in Biomedicine 25 (1987), pp. 13-20.

Recursive All-Pass Filters, Presented at International Conference on Signal Processing, Florence, Italy, Sep. 4-6, 1991, 6 pages.

Rusch, T.L., Sankar, R., Scharf, J.E., "*Signal Processing Methods for Pulse Oximetry*," Compw. Biol. Med., vol. 26, No. 2, pp. 143-159 (1996).

S. Kojima et al., "Tissue Oxygen Saturation by Reflectance Spectrum Oxymetry in Myocardial lschemia", Circulation, vol. 72, No. 4, Part II, Total pp. 3 Oct. 1985.

Sakata, M. et al., "Rapid Determination of Carboxyhemoglobin by Absorbance Difference Between Double Wavelength," The Journal of Toxicological Science, 1980, vol. 5, pp. 113-121.

Setsuo Takatani et al., "A Miniature Hybrid Reflection Type Optical Sensor for Measurement of Hemoglobin Content and Oxygen Saturation of Whole Blood," IEEE Transactions on Biomedical Engineering, vol. 35. No. 3, Mar. 1988, pp. 187-198.

Takashi Hanioka, "Evaluation of Hemoglobin Concentration and Oxygen Saturation in Inflamed Gingiva by Tissue Reflectance Spectrophotometry," J. Osaka Univ. Dent. Soc., vol. 33, pp. 437-455, 1988.

V. Ya. Volkov et al., "Enhancing the Reliability and Accuracy of Pulse Oximetry with a Built-In Expert System," 1993 Plenum Publishing Corporation, pp. 133-138.

Y. Shimada et al., "Effects of multiple scattering and peripheral circulation on arterial oxygen saturation measured with a pulse-type oximeter," Medical & Biological Engineering & Computing, Sep. 1984, pp. 475-478.

Bruce H. McCormick et al., "Computer Eye Looks at Human Eye", pp. 687-697.

C. Zamarron et al., "Oximetry spectral analysis in the diagnosis of obstructive sleep apnoea," The Biochemical Society and the Medical Research Society, 1999, pp. 467-473.

Brown, David P., "Evaluation of Pulse Oximeters using Theoretical Models and Experimental Studies", Master's thesis, University of Washington, Nov. 25, 1987, pp. 1-142.

C. Baker; "Design Summary and Evaluation of Saturation Arbitrator," dated Sep. 14, 1994.

Chen, Jiande, et al., "Adaptive System for Processing of Electrogastric Signals", Images of the Twenty-First Century, Seattle, WA, vol. 11, Nov. 9-12, 1989. pp. 698-699.

Cohen, Arnon, "Volume I", Time and Frequency Domains Analysis, Biomedical Signal Processing, CRC Press, Inc., Boca Raton, Florida, pp. 152-159.

European Search Report, dated Sep. 1999.

Jingzheng, Ouyang, et al., "Digital Processing of High-Resolution Electrocardiograms—Detection of His-Purkinje Activity from the Body Surface", Biomedizinische Technik33, Oct. 1, 1988, No. 10, Berlin, W. Germany, pp. 224-230.

Klimasauskas, Casey, "Neural Nets and Noise Filtering", Dr. Dobb's Journal, Jan. 1989, p. 32.

*Mallinckrodt inc. v. Masimo Corp.*, 2004 U.S. Dist. Lexis 28518 (C.D. Cal. Jul. 12, 2004).

*Mallinckrodt, Inc. v. Masimo Corp.*, 147 Fed. Appx. 158, 2005 WL 2139867 (Fed. Cir. 2005).

Masimo Corp's Answer to Plaintiffs' Second Amended Complaint and Counterclaims; Demand for Jury Trial, dated Nov. 2, 2000.

Masimo's Opposition to Defendants' Motion for Summary Judgment for Summary Judgment of Invalidity of Claim 19 of U.S. Patent No. 5,490,505, dated Sep. 21, 2000.

Masimo's Reply to Nellcor's and Mallinckrodt's First Amended and Supplemental Reply and Counterclaims to Counterclaims of Masimo, dated Aug. 27, 2002.

Masimo's Answer to Counterclaims to Nellcor's Third Amended Complaint for Patent Infringement; Demand for Jury Trial, dated Aug. 27, 2002.

Masimo's Reply to Nellcor's and Mallinckrodt's Amended and Supplemental Answer and Counterclaims to Masimo's First Amended Complaint in Case No. CV-01-7292 MRP (AJWx), dated Aug. 27, 2002.

Melnikof, S. "Neural Networks for Signal Processing: A Case Study", Dr. Dobbs Journal, Jan. 1989. pp. 36-37.

Mook, G. A., et al., "Spectrophotometric determination of Oxygen saturation of blood independent of the presence of indocyanine green", Cardiovascular Research, vol. 13, pp. 233-237, 1979.

Mook, G. A., et al., "Wavelength dependency of the spectrophotometric determination of blood oxygen saturation", Clinical Chemistry Acata, vol. 26, pp. 170-173, 1969.

Nellcor's and Mallinckrodt's Amended and Supplemental Answer to Counterclaims to Masimo Corporation's First Amended Complaint in Case No. CV-01-7293-MRP (AJWx), dated Mar 31, 2002.

Nellcor's and Mallinckrodt's Amended Complaint for Patent Infringement.

Nellcor's Oct. 13, 2003 Supplemental and Revised Response to Masimo's First Set of Interrogatories in the Consolidated Case (No. 2), dated Oct. 13, 2003.

Nellcor's Response to Masimo's First Set of Interrogatories in the Consolidated Case to Mallinckrodt Inc. and Nellcor Puritan Bennett, Inc. (Nos. 1-8), dated Aug. 23, 2002.

Nellcor's Revised and Corrected Supplemental Response to Masimo's First Set of Interrogatories in the Consolidated Case (No. 2), dated Jun. 25, 2003.

Nellcor's Second Supplemental Response to Masimo's First Set of Interrogatories in Consolidated Case (No. 2), dated Jul. 14, 2003.

Nellcor's Supplemental Response to Masimo's First Set of Interrogatories in the Consolidated Case (No. 2), dated Jun. 24, 2003.

Nellcor's and Mallinckrodt's Answer to First Amended Complaint, dated Aug. 20, 2001.

Nellcor's and Mallinckrodt's First Amended and Supplemental Reply and Counterclaims to Counterclaims of Masimo Corporation, dated May 31, 2002.

Nellcor's Reply to Amended Counterclaims of Masimo Corporation, dated Feb. 22, 2000.

Nellcor's Third Amended Complaint for Patent Infringement of U.S. Patent Nos. 4,621,643, 4,653,498, 4,700,708, 5,078,136, 5,807,247 and Re. 36,000; Demand for Jury Trial, dated Jul. 31, 2002.

Nellcor's Third Amended Complaint for Patent Infringement, Aug. 27, 2002.

Nellcor's Trial Brief on Indefiniteness, dated Mar. 23, 2004.

Nellcor's Trial Brief re Inequitable Conduct, dated Mar. 23, 2004.

Neuman, Michael R., "Pulse Oximetry: Physical Principals, Technical Realization and Present Limitations", Continuous Transcutaneous Monitoring, Plenum Press, New York, 1987, pp. 135-144.

Rabiner, Lawrence et al. Theory and Application of Digital Signal Processing, p. 260, 1975.

Tremper, Kevin et al. Advances in Oxygen Monitoring, pp. 137-153, 1987.

Tremper, K. K., et al., "Pulse Oximetry: Technical Aspects of Machine Design," Advances in Oxygen Monitoring, pp. 137-153, (1987).

United States Courts of Appeals for the Federal Circuit: *Mallinckrodt, Inc. v. Masimo Corp.*, 147 F.App'x 158 (Fed. Cir. 2005).

United States Courts of Appeals for the Federal Circuit: *Mallinckrodt, Inc. v. Masimo Corp.*, 402 F.3d 1364 (Fed. Cir. 2005).

United States Courts of Appeals for the Federal Circuit: *Masimo Corp. v. Mallinckrodt, Inc.*, 18 F App'x.

Varanini, M., et al., "A Two Channel Adaptive Filtering Approach for Recognition of the QRS Morphology", pp. 141-144, Proceedings of the Computers in Cardiology Meeting, Venice, Institute of Electrical and Electronics Engineers, Sep. 23-26, 1991.
Complaint for Patent Infringement, *Masimo Corporation v. Philips Electronics North America Corporation and Philips Medizin Systeme Böblingen GMBH*, (District of Delaware, Case No. 09-000080(JJF)), dated Feb. 3, 2009.
Defendant/Counterclaim-Plaintiff Philips Electronics North America Corporation Answer to Masimo's Counterclaims, *Masimo Corporation v. Philips Electronics North America Corporation and Philips Medizin Systeme Böblingen GMBH*, (District of Delaware, Case No. 09-00080(JJF)) dated Aug. 3, 2009, pp. 1-23.
Defendants' Answer and Philips Electronics North America Corporation's Amended Counterclaims to Masimo's First Amended Complaint, *Masimo Corporation v. Philips Electronics North America Corporation and Philips Medizin Systeme Böblingen GMBH*, (District of Delaware, Case No. 09-00080(JJF)) dated Apr. 21, 2010.
Defendants' Answer and Philips Electronics North America Corporation's Counterclaims to Masimo's First Amended Complaint, *Masimo Corporation v. Philips Electronics North America Corporation and Philips Medizin Systeme Böblingen GMBH*, (District of Delaware, Case No. 09-00080(JJF)) dated Jun. 15, 2009.
First Amended Complaint for Patent Infringement, *Masimo Corporation v. Philips Electronics North America Corporation and Philips Medizin Systeme Böblingen GMBH*, (District of Delaware, Case No. 09-00080(JJF)) dated May 12, 2009.
Masimo's Answer to Philips' Amended Counterclaims, *Masimo Corporation v. Philips Electronics North America Corporation and Philips Medizin Systeme Böblingen GMBH*, (District of Delaware, Case No. 09-00080(JJF)) dated May 10, 2010.
Masimo's Answer to Philips' Counterclaims, *Masimo Corporation v. Philips Electronics North America Corporation and Philips Medizin Systeme Böblingen GMBH*, (District of Delaware, Case No. 0900080(JJF)) dated Jul. 9, 2009.
Philips Electronics North America Corporation's Answer to Masimo's Amended Counterclaims, *Masimo Corporation v. Philips Electronics North America Corporation and Philips Medizin Systeme Böblingen GMBH*, (District of Delaware, Case No. 09-00080(JJF)) dated May 27, 2010.
Philips North America Corporation and Philips Medizin Systeme Böblingen GMBH's Seventh Supplemental Objections and Responses to Masimo Corporation's First Set of Interrogatories (Nos. 1-8), *Masimo Corporation v. Philips Electronics North America Corporation and Philips Medizin Systeme Böblingen GMBH*, (District of Delaware, Case No. 09-00080(JJF)) dated Jun. 30, 2010 (Redacted).
Copending U.S. Appl. No. 09/111,604, filed Jul. 7, 1998; (Masimo. 007C3).
Copending U.S. Appl. No. 07/666,060, filed on Mar. 7, 1991.
U.S. Appl. No. 09/110,542, filed Jul. 6, 1998.
Patently Obvious™, Intellectual Property Analysis of Masimo Inc. Patent Holdings, *Masimo Corporation v. Philips Electronics North America Corporation*, et al. issued on Nov. 4, 2010 via email in 9 pages.
*Mallinckrodt, Inc. v. Masimo Corp.*, 254 F. Supp.2d 1140 (C.D. Cal. 2003).
Revised Joint Claim Construction Chart, *Masimo Corporation v. Philips Electronics North America Corporation and Philips Medizin Systeme Böblingen GMBH*, (District of Delaware, Case No. 1:09-cv-00080 (LPS/MPT) dated Oct. 19, 2010.
Philips' Opening Markman Brief, *Masimo Corporation v. Philips Electronics North America Corporation and Philips Medizin Systeme Böblingen GMBH*, (District of Delaware, Case No. 1:09-cv-00080 (LPS/MPT) dated Oct. 19, 2010.
Masimo Corporation's Opening Claim Construction Brief, *Masimo Corporation v. Philips Electronics North America Corporation and Philips Medizin Systeme Böblingen GMBH*, (District of Delaware, Case No. 1:09-cv-00080 (LPS/MPT) dated Oct. 19, 2010.
Declaration of Perry D. Oldham in Support of Masimo Corporation's Opening Claim Construction Brief, *Masimo Corporation v. Philips Electronics North America Corporation and Philips Medizin Systeme Böblingen GMBH*, (District of Delaware, Case No. 1:09-cv-00080 (LPS/MPT) dated Oct. 19, 2010.
Declaration of Robert T. Stone in Support of Philips' Responsive Markman Brief, *Masimo Corporation v. Philips Electronics North America Corporation and Philips Medizin Systeme Böblingen GMBH*, (District of Delaware, Case No. 1:09-cv-00080 (LPS/MPT) dated Nov. 15, 2010.
Masimo Corporation's Responsive Claim Construction Brief, *Masimo Corporation v. Philips Electronics North America Corporation and Philips Medizin Systeme Böblingen GMBH*, (District of Delaware, Case No. 1:09-cv-00080 (LPS/MPT) dated Nov. 19, 2010 (Redacted).
Confidential Declaration of Michelle Armond in Support of Masimo Corporation's Responsive Claim Construction Brief, *Masimo Corporation v. Philips Electronics North America Corporation and Philips Medizin Systeme Böblingen GMBH*, (District of Delaware, Case No. 1:09-cv-00080 (LPS/MPT) dated Nov. 19, 2010 (Redacted).
Philips' Responsive Markman Brief, *Masimo Corporation v. Philips Electronics North America Corporation and Philips Medizin Systeme Böblingen GMBH*, (District of Delaware, Case No. 1:09-cv00080 (LPS/MPT) dated Nov. 22, 2010.
Masimo's Technical Tutorial, *Masimo Corporation v. Philips Electronics North America Corporation and Philips Medizin Systeme Böblingen GMBH*, (District of Delaware, Case No. 1:09-cv-00080 (LPS/MPT) dated Dec. 1, 2010.
Phlips' Claim Construction Hearing, Presentation Materials, *Masimo Corporation v. Philips Electronics North America Corporation and Philips Medizin Systeme Böblingen GMBH*, (District of Delaware, Case No. 1:09-cv-00080 (LPS/MPT) dated Dec. 1, 2010.
Transcript of Markman Hearing, *Masimo Corporation v. Philips Electronics North America Corporation and Philips Medizin Systeme Böblingen GMBH*, (District of Delaware, Case No. 1:09-cv-00080 (LPS/MPT) dated Dec. 1, 2010.

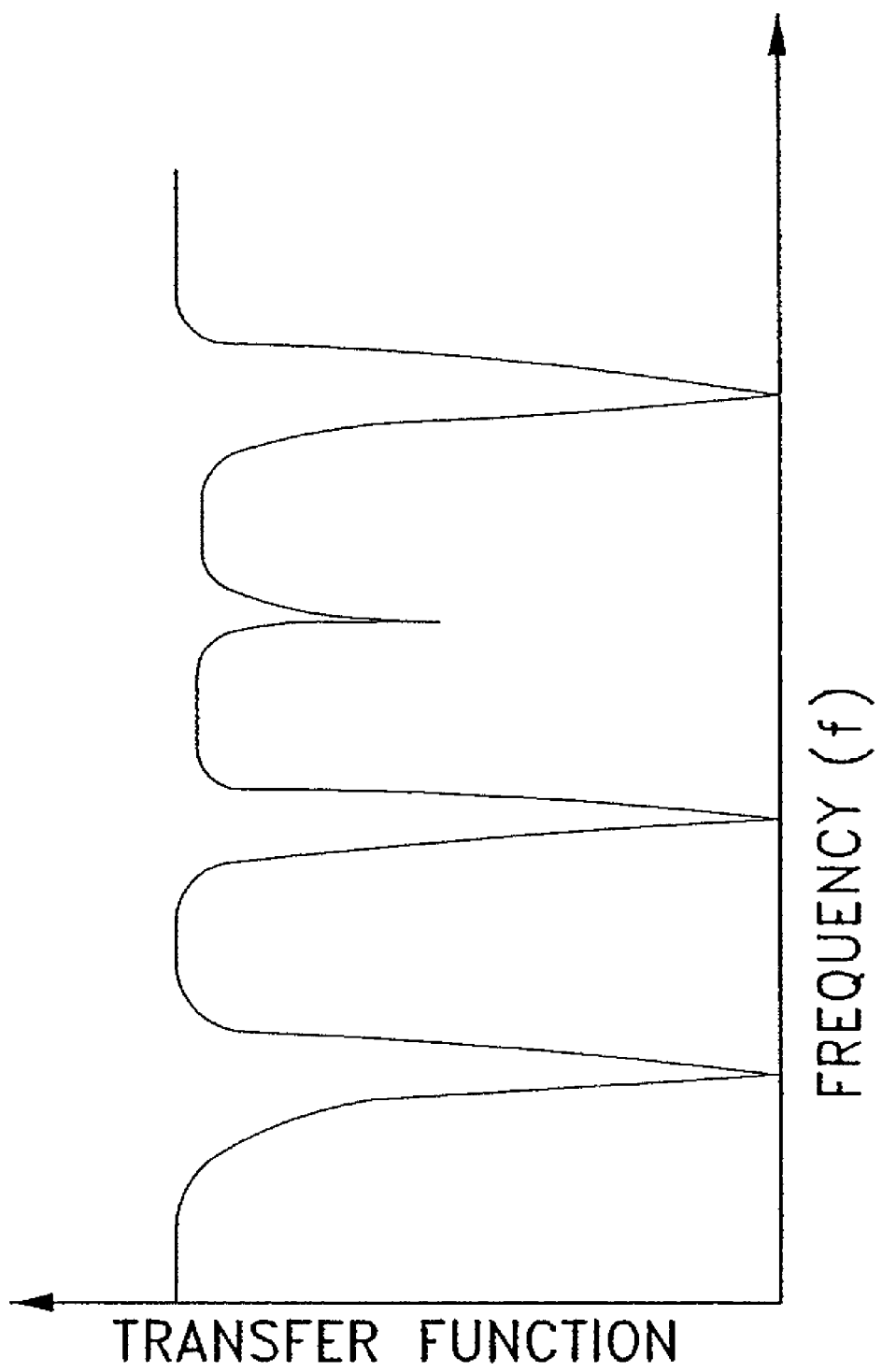

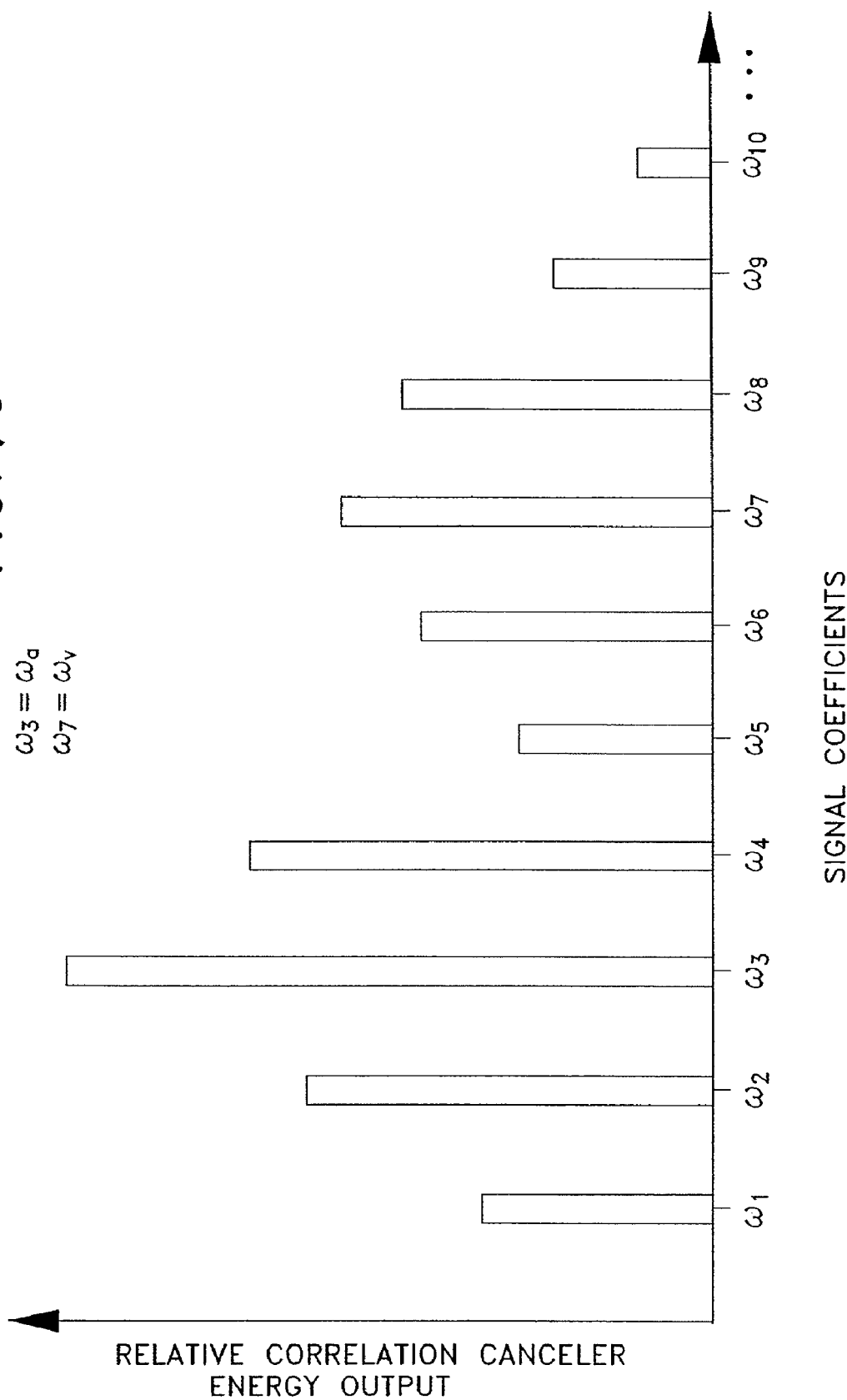

SIGNAL PROCESSING APPARATUS

PRIORITY CLAIM

This application is a continuation of U.S. patent application Ser. No. 10/779,033, filed Feb. 13, 2004, which is a continuation of U.S. patent application Ser. No. 09/111,604, filed Jul. 7, 1998, which is a continuation of U.S. patent application Ser. No. 08/943,511, filed Oct. 6, 1997, now U.S. Pat. No. 6,263,222, which is a continuation of U.S. patent application Ser. No. 08/572,488, filed Dec. 14, 1995, now U.S. Pat. No. 5,685,299, which is a continuation of U.S. application Ser. No. 08/132,812, filed on Oct. 6, 1993, now U.S. Pat. No. 5,490,505, which is a continuation-in-part of U.S. patent application Ser. No. 07/666,060, filed Mar. 7, 1991, now abandoned. The present application incorporates each of the foregoing disclosures herein by reference.

BACKGROUND OF THE INVENTION

1. Field of the Invention

The present invention relates to the field of signal processing. More specifically, the present invention relates to the processing of measured signals, containing a primary and a secondary signal, for the removal or derivation of either the primary or secondary signal when little is known about either of these components. The present invention also relates to the use of a novel processor which in conjunction with a correlation canceler, such as an adaptive noise canceler, produces primary and/or secondary signals. The present invention is especially useful for physiological monitoring systems including blood oxygen saturation.

2. Description of the Related Art

Signal processors are typically employed to remove or derive either the primary or secondary signal portion from a composite measured signal including a primary signal portion and a secondary signal portion. If the secondary signal portion occupies a different frequency spectrum than the primary signal portion, then conventional filtering techniques such as low pass, band pass, and high pass filtering could be used to remove or derive either the primary or the secondary signal portion from the total signal. Fixed single or multiple notch filters could also be employed if the primary and/or secondary signal portion(s) exit at a fixed frequency(s).

It is often the case that an overlap in frequency spectrum between the primary and secondary signal portions exists. Complicating matters further, the statistical properties of one or both of the primary and secondary signal portions change with time. In such cases, conventional filtering techniques are totally ineffective in extracting either the primary or secondary signal. If, however, a description of either the primary or secondary signal portion can be made available correlation canceling, such as adaptive noise canceling, can be employed to remove either the primary or secondary signal portion of the signal leaving the other portion available for measurement.

Correlation cancelers, such as adaptive noise cancelers, dynamically change their transfer function to adapt to and remove either the primary or secondary signal portions of a composite signal. Correlation cancelers require either a secondary reference or a primary reference which is correlated to either the secondary signal or the primary signal portions only. The reference signals are not necessarily a representation of the primary or secondary signal portions, but have a frequency spectrum which is similar to that of the primary or secondary signal portions. In many cases, it requires considerable ingenuity to determine a reference signal since nothing is usually known a priori about the secondary and/or primary signal portions.

One area where composite measured signals comprising a primary signal portion and a secondary signal portion about which no information can easily be determined is physiological monitoring. Physiological monitoring apparatuses generally measure signals derived from a physiological system, such as the human body. Measurements which are typically taken with physiological monitoring systems include electrocardiographs, blood pressure, blood gas saturation (such as oxygen saturation), capnographs, heart rate, respiration rate, and depth of anesthesia, for example. Other types of measurements include those which measure the pressure and quantity of a substance within the body such as breathalyzer testing, drug testing, cholesterol testing, glucose testing, arterial carbon dioxide testing, protein testing, and carbon monoxide testing, for example. Complications arising in these measurements are often due to motion of the patient, both external and internal (muscle movement, for example), during the measurement process.

Knowledge of physiological systems, such as the amount of oxygen in a patient's blood, can be critical, for example during surgery. These data can be determined by a lengthy invasive procedure of extracting and testing matter, such as blood, from a patient, or by more expedient, non-invasive measures. Many types of non-invasive measurements can be made by using the known properties of energy attenuation as a selected form of energy passes through a medium.

Energy is caused to be incident on a medium either derived from or contained within a patient and the amplitude of transmitted or reflected energy is then measured. The amount of attenuation of the incident energy caused by the medium is strongly dependent on the thickness and composition of the medium through which the energy must pass as well as the specific form of energy selected. Information about a physiological system can be derived from data taken from the attenuated signal of the incident energy transmitted through the medium if either the primary or secondary signal of the composite measurement signal can be removed. However, non-invasive measurements often do not afford the opportunity to selectively observe the interference causing either the primary or secondary signal portions, making it difficult to extract either one of them from the composite signal.

The primary and/or secondary signal portions often originate from both AC and/or DC sources. The DC portions are caused by transmission of the energy through differing media which are of relatively constant thickness within the body, such as bone, tissue, skin, blood, etc. These portions are easy to remove from a composite signal. The AC components are caused by physiological pulsations or when differing media being measured are perturbed and thus, change in thickness while the measurement is being made. Since most materials in and derived from the body are easily compressed, the thickness of such matter changes if the patient moves during a non-invasive physiological measurement. Patient movement, muscular movement and vessel movement, can cause the properties of energy attenuation to vary erratically. Traditional signal filtering techniques are frequently totally ineffective and grossly deficient in removing these motion induced effects from a signal. The erratic or unpredictable nature of motion induced signal components is the major obstacle in removing or deriving them. Thus, presently available physiological monitors generally become totally inoperative during time periods when the measurement site is perturbed.

A blood gas monitor is one example of a physiological monitoring system which is based upon the measurement of energy attenuated by biological tissues or substances. Blood gas monitors transmit light into the tissue and measure the attenuation of the light as a function of time. The output signal of a blood gas monitor which is sensitive to the arterial blood flow contains a component which is a waveform representative of the patient's arterial pulse. This type of signal, which contains a component related to the patient's pulse, is called a plethysmographic wave, and is shown in FIG. 1 as curve s. Plethysmographic waveforms are used in blood pressure or blood gas saturation measurements, for example. As the heart beats, the amount of blood in the arteries increases and decreases, causing increases and decreases in energy attenuation, illustrated by the cyclic waves in FIG. 1.

Typically, a digit such as a finger, an ear lobe, or other portion of the body where blood flows close to the skin, is employed as the medium through which light energy is transmitted for blood gas attenuation measurements. The finger comprises skin, fat, bone, muscle, etc., shown schematically in FIG. 2, each of which attenuates energy incident on the finger in a generally predictable and constant manner. However, when fleshy portions of the finger are compressed erratically, for example by motion of the finger, energy attenuation becomes erratic.

An example of a more realistic measured waveform S is shown in FIG. 3, illustrating the effect of motion. The primary plethysmographic waveform portion of the signal s is the waveform representative of the pulse, corresponding to the sawtooth-like pattern wave in FIG. 1. The large, secondary motion-induced excursions in signal amplitude hide the primary plethysmographic signal s. It is easy to see how even small variations in amplitude make it difficult to distinguish the primary signal s in the presence of a secondary signal component n.

A specific example of a blood gas monitoring apparatus is a pulse oximeter which measures the arterial saturation of oxygen in the blood. The pumping of the heart forces freshly oxygenated blood into the arteries causing greater energy attenuation. The arterial saturation of oxygenated blood may be determined from the depth of the valleys relative to the peaks of two plethysmographic waveforms measured at separate wavelengths. Patient movement introduces signal portions mostly due to venous blood, or motion artifacts, to the plethysmographic waveform illustrated in FIG. 3. It is these motion artifacts which must be removed from the measured signal for the oximeter to continue the measurement of arterial blood oxygen saturation, even during periods when the patient moves. It is also these motion artifacts which must be derived from the measured signal for the oximeter to obtain an estimate of venous blood oxygen saturation. Once the signal components due to either arterial blood or venous blood is known, its corresponding oxygen saturation may be determined.

SUMMARY OF THE INVENTION

This invention is an improvement of U.S. patent application Ser. No. 07/666,060 filed Mar. 7, 1991 and entitled Signal Processing Apparatus and Method, which earlier application has been assigned to the assignee of the instant application. The invention is a signal processor which acquires a first signal and a second signal that is correlated to the first signal. The first signal comprises a first primary signal portion and a first secondary signal portion. The second signal comprises a second primary signal portion and a second secondary signal portion. The signals may be acquired by propagating energy through a medium and measuring an attenuated signal after transmission or reflection. Alternatively, the signals may be acquired by measuring energy generated by the medium.

The first and second measured signals are processed to generate a secondary reference which does not contain the primary signal portions from either of the first or second measured signals. The remaining secondary signal portions from the first and second measured signals are combined to form the secondary reference. This secondary reference is correlated to the secondary signal portion of each of the first and second measured signals.

The secondary reference is then used to remove the secondary portion of each of the first and second measured signals via a correlation canceler, such as an adaptive noise canceler. The correlation canceler is a device which takes a first and second input and removes from the first input all signal components which are correlated to the second input. Any unit which performs or nearly performs this function is herein considered to be a correlation canceler. An adaptive correlation canceler can be described by analogy to a dynamic multiple notch filter which dynamically changes its transfer function in response to a reference signal and the measured signals to remove frequencies from the measured signals that are also present in the reference signal. Thus, a typical adaptive correlation canceler receives the signal from which it is desired to remove a component and a reference signal. The output of the correlation canceler is a good approximation to the desired signal with the undesired component removed.

Alternatively, the first and second measured signals may be processed to generate a primary reference which does not contain the secondary signal portions from either of the first or second measured signals. The remaining primary signal portions from the first and second measured signals are combined to form the primary reference. The primary reference may then be used to remove the primary portion of each of the first and second measured signals via a correlation canceler. The output of the correlation canceler is a good approximation to the secondary signal with the primary signal removed and may be used for subsequent processing in the same instrument or an auxiliary instrument. In this capacity, the approximation to the secondary signal may be used as a reference signal for input to a second correlation canceler together with either the first or second measured signals for computation of, respectively, either the first or second primary signal portions.

Physiological monitors can often advantageously employ signal processors of the present invention. Often in physiological measurements a first signal comprising a first primary portion and a first secondary portion and a second signal comprising a second primary portion and a second secondary portion are acquired. The signals may be acquired by propagating energy through a patient's body (or a material which is derived from the body, such as breath, blood, or tissue, for example) or inside a vessel and measuring an attenuated signal after transmission or reflection. Alternatively, the signal may be acquired by measuring energy generated by a patient's body, such as in electrocardiography. The signals are processed via the signal processor of the present invention to acquire either a secondary reference or a primary reference which is input to a correlation canceler, such as an adaptive noise canceler.

One physiological monitoring apparatus which can advantageously incorporate the features of the present invention is a monitoring system which determines a signal which is representative of the arterial pulse, called a plethysmographic wave. This signal can be used in blood pressure calculations, blood gas saturation measurements, etc. A specific example of such a use is in pulse oximetry which determines the saturation of oxygen in the blood. In this configuration, we define the primary portion of the signal to be the arterial blood contribution to attenuation of energy as it passes through a portion of the body where blood flows close to the skin. The pumping of the heart causes blood flow to increase and decrease in the arteries in a periodic fashion, causing periodic attenuation wherein the periodic waveform is the plethysmographic waveform representative of the arterial pulse. We define the secondary portion of the signal to be that which is usually considered to be noise. This portion of the signal is related to the venous blood contribution to attenuation of energy as it passes through the body. Patient movement causes this component to flow in an unpredictable manner, causing unpredictable attenuation and corrupting the otherwise periodic plethysmographic waveform. Respiration also causes secondary or noise component to vary, although typically at a much lower frequency than the patients pulse rate.

A physiological monitor particularly adapted to pulse oximetry oxygen saturation measurement comprises two light emitting diodes (LED's) which emit light at different wavelengths to produce first and second signals. A detector registers the attenuation of the two different energy signals after each passes through an absorptive media, for example a digit such as a finger, or an earlobe. The attenuated signals generally comprise both primary and secondary signal portions. A static filtering system, such as a bandpass filter, removes a portion of the secondary signal which is outside of a known bandwidth of interest, leaving an erratic or random secondary signal portion, often caused by motion and often difficult to remove, along with the primary signal portion.

Next, a processor of the present invention removes the primary signal portions from the measured signals yielding a secondary reference which is a combination of the remaining secondary signal portions. The secondary reference is correlated to both of the secondary signal portions. The secondary reference and at least one of the measured signals are input to a correlation canceler, such as an adaptive noise canceler, which removes the random or erratic portion of the secondary signal. This yields a good approximation to the primary plethysmographic signal as measured at one of the measured signal wavelengths. As is known in the art, quantitative measurements of the amount of oxygenated arterial blood in the body can be determined from the plethysmographic signal in a variety of ways.

The processor of the present invention may also remove the secondary signal portions from the measured signals yielding a primary reference which is a combination of the remaining primary signal portions. The primary reference is correlated to both of the primary signal portions. The primary reference and at least one of the measured signals are input to a correlation canceler which removes the primary portions of the measured signals. This yields a good approximation to the secondary signal at one of the measured signal wavelengths. This signal may be useful for removing secondary signals from an auxiliary instrument as well as determining venous blood oxygen saturation.

One aspect of the present invention is a signal processor comprising a detector for receiving a first signal which travels along a first propagation path and a second signal which travels along a second propagation path wherein a portion of the first and second propagation paths are located in a propagation medium. The first signal has a first primary signal portion and a first secondary signal portion and the second signal has a second primary signal portion and a second secondary signal portion. The first and second secondary signal portions are a result of a change of the propagation medium. This aspect of the invention additionally comprises a reference processor having an input for receiving the first and second signals. The processor is adapted to combine the first and second signals to generate a secondary reference having a significant component which is a function of the first and said second secondary signal portions. The processor may also be adapted to combine the first and second signals to generate a primary reference having a significant component which is a function of the first and second primary signal portions The above described aspect of the present invention may further comprise a signal processor for receiving the secondary reference signal and the first signal and for deriving therefrom an output signal having a significant component which is a function of the first primary signal portion of the first signal. Alternatively, the above described aspect of the present invention may further comprise a signal processor for receiving the secondary reference signal and the second signal and for deriving therefrom an output signal having a significant component which is a function of the second primary signal portion of the second signal. Alternatively, the above described aspect of the present invention may further comprise a signal processor for receiving the primary reference and the first signal and for deriving therefrom an output signal having a significant component which is a function of the first secondary signal portion of the signal of the first signal. Alternatively, the above described aspect of the present invention may further comprise a signal processor for receiving the primary reference and the second signal and for deriving therefrom an output signal having a significant component which is a function of the second secondary signal portion of the second signal. The signal processor may comprise a correlation canceler, such as an adaptive noise canceler. The adaptive noise canceler may comprise a joint process estimator having a least-squares-lattice predictor and a regression filter.

The detector in the aspect of the signal processor of the present invention described above may further comprise a sensor for sensing a physiological function. The sensor may comprise a light or other electromagnetic sensitive device. Additionally, the present invention may further comprise a pulse oximeter for measuring oxygen saturation in a living organism. The present invention may further comprise an electrocardiograph.

Another aspect of the present invention is a physiological monitoring apparatus comprising a detector for receiving a first physiological measurement signal which travels along a first propagation path and a second physiological measurement signal which travels along a second propagation path. A portion of the first and second propagation paths being located in the same propagation medium. The first signal has a first primary signal portion and a first secondary signal portion and the second signal has a second primary signal portion and a second secondary signal portion. The physiological monitoring apparatus further comprises a reference processor having an input for receiving the first and second signals. The processor is adapted to combine the first and second signals to generate a secondary reference signal having a significant component which is a function of the first and the second secondary signal portions. Alternatively, the processor may be adapted to combine the first and second signals to generate a primary reference having a component which is a function of the first and second primary signal portions.

The physiological monitoring apparatus may further comprise a signal processor for receiving the secondary reference and the first signal and for deriving therefrom an output signal having a significant component which is a function of the first primary signal portion of the first signal. Alternatively, the physiological monitoring apparatus may further comprise a signal processor for receiving the secondary reference and the second signal and for deriving therefrom an output signal having a significant component which is a function of the second primary signal portion of the second signal. Alternatively, the physiological monitoring apparatus may further comprise a signal processor for receiving the primary reference and the first signal and deriving therefrom an output signal having a significant component which is a function of the first secondary signal portion of the first signal. Alternatively, the physiological monitoring apparatus may further comprise a signal processor for receiving the primary reference and the second signal and deriving therefrom an output signal having a significant component which is a function of the second secondary signal portion of the second signal.

A further aspect of the present invention is an apparatus for measuring a blood constituent comprising an energy source for directing a plurality of predetermined wavelengths of electromagnetic energy upon a specimen and a detector for receiving the plurality of predetermined wavelengths of electromagnetic energy from the specimen. The detector produces electrical signals corresponding to the predetermined wavelengths in response to the electromagnetic energy. At least two of the electrical signals are used each having a primary signal portion and an secondary signal portion. Additionally, the apparatus comprises a reference processor having an input for receiving the electrical signals. The processor is configured to combine said electrical signals to generate a secondary reference having a significant component which is derived from the secondary signal portions. Alternatively, the processor may be configured to combine said signals to generate a primary reference having a significant component which is derived from the primary signal portions.

This aspect of the present invention may further comprise a signal processor for receiving the secondary reference and one of the two electrical signals and for deriving therefrom an output signal having a significant component which is a function of the primary signal portion of one of the two electrical signals. Another aspect of the present invention may further comprise a signal processor for receiving the primary reference and one of the two electrical signals and for deriving therefrom an output signal having a significant component which is a function of the secondary signal portion of one of the two electrical signals. This may be accomplished by use of a correlation canceler, such as an adaptive noise canceler, in the signal processor which may employ a joint process estimator having a least-squares-lattice predictor and a regression filter.

Yet another aspect of the present invention is a blood gas monitor for non-invasively measuring a blood constituent in a body comprising a light source for directing at least two predetermined wavelengths of light upon a body and a detector for receiving the light from the body. The detector, in response to the light from the body, produces at least two electrical signals corresponding to the at least two predetermined wavelengths of light. The at least two electrical signals each have a primary signal portion and a secondary signal portion. The blood oximeter further comprises a reference processor having an input for receiving the at least two electrical signals. The processor is adapted to combine the at least two electrical signals to generate a secondary reference with a significant component which is derived from the secondary signal portions. The blood oximeter may further comprise a signal processor for receiving the secondary reference and the two electrical signals and for deriving therefrom at least two output signals which are substantially equal, respectively, to the primary signal portions of the electrical signals. Alternatively, the reference processor may be adapted to combine the at least two electrical signals to generate a primary reference with a significant component which is derived from the primary signal portions. The blood oximeter may further comprise a signal processor for receiving the primary reference and the two electrical signals and for deriving therefrom at least two output signals which are substantially equivalent to the secondary signal portions of the electrical signal. The signal processor may comprise a joint process estimator.

The present invention also includes a method of determining a secondary reference from a first signal comprising a first primary signal portion and a first secondary portion and a second signal comprising a second primary signal portion and a second secondary portion. The method comprises the steps of selecting a signal coefficient which is proportional to a ratio of predetermined attributes of the first primary signal portion and predetermined attributes of the second primary signal portion. The first signal and the signal coefficient are input into a signal multiplier wherein the first signal is multiplied by the signal coefficient thereby generating a first intermediate signal. The second signal and the first intermediate signal are input into a signal subtractor wherein the first intermediate signal is subtracted from the second signal. This generates a secondary reference having a significant component which is derived from the first and second secondary signal portions.

The present invention also includes a method of determining a primary reference from a first signal comprising a first primary signal portion and a first secondary signal portion and a second signal comprising a second primary signal portion and a second secondary signal portion. The method comprises the steps of selecting a signal coefficient which is proportional to a ratio of the predetermined attributes of the first secondary signal portion and predetermined attributes of the second secondary signal portion. The first signal and the signal coefficient are input into a signal multiplier wherein the first signal is multiplied by the signal coefficient thereby generating a first intermediate signal. The second signal and the first intermediate signal are input into a signal subtractor wherein the first intermediate signal is subtracted from the second signal. This generates a primary reference having a significant component which is derived from the first and second primary signal portions. The first and second signals in this method may be derived from electromagnetic energy transmitted through an absorbing medium.

The present invention further embodies a physiological monitoring apparatus comprising means for acquiring a first signal comprising a first primary signal portion and a first secondary signal portion and a second signal comprising a second primary signal portion and a second secondary signal portion. The physiological monitoring apparatus of the present invention also comprises means for determining from the first and second signals a secondary reference. Additionally, the monitoring apparatus comprises a correlation canceler, such as an adaptive noise canceler, having a secondary reference input for receiving the secondary reference and a signal input for receiving the first signal wherein the correlation canceler, in real or near real time, generates an output signal which approximates the first primary signal portion. Alternatively, the physiological monitoring device may also comprise means for determining from the first and second signals a primary reference. Additionally, the monitoring apparatus comprises a correlation canceler having a primary reference input for receiving the primary reference and a signal input for receiving the first signal wherein the correlation canceler, in real or near real time, generates an output signal which approximates the first secondary signal portion. The correlation canceler may further comprise a joint process estimator.

A further aspect of the present invention is an apparatus for processing an amplitude modulated signal having a signal amplitude complicating feature, the apparatus comprising an energy source for directing electromagnetic energy upon a specimen. Additionally, the apparatus comprises a detector for acquiring a first amplitude modulated signal and a second amplitude modulated signal. Each of the first and second signals has a component containing information about the attenuation of electromagnetic energy by the specimen and a signal amplitude complicating feature. The apparatus includes a reference processor for receiving the first and second amplitude modulated signals and deriving therefrom a secondary reference which is correlated with the signal amplitude complicating feature. Further, the apparatus incorporates a correlation canceler having a signal input for receiving the first amplitude modulated signal, a secondary reference input for receiving the secondary reference, wherein the correlation canceler produces an output signal having a significant component which is derived from the component containing information about the attenuation of electromagnetic energy by the specimen. Alternatively, the apparatus may also include a reference processor for receiving the first and second amplitude modulated signals and deriving therefrom a primary reference which is correlated with the component containing information about the attenuation of electromagnetic energy by the specimen. Further, the apparatus incorporates a correlation canceler having a signal input for receiving the first amplitude modulated signal, a primary reference input for receiving the primary reference, wherein the correlation canceler produces an output signal having a primary component which is derived from the signal amplitude complicating feature.

Still another aspect of the present invention is an apparatus for extracting a plethysmographic waveform from an amplitude modulated signal having a signal amplitude complicating feature, the apparatus comprising a light source for transmitting light into an organism and a detector for monitoring light from the organism. The detector produces a first light attenuation signal and a second light attenuation signal, wherein each of the first and second light attenuation signals has a component which is representative of a plethysmographic waveform and a component which is representative of the signal amplitude complicating feature. The apparatus also includes a reference processor for receiving the first and second light attenuation signals and deriving therefrom a secondary reference. The secondary reference and the signal amplitude complicating feature each have a frequency spectrum. The frequency spectrum of the secondary reference is correlated with the frequency spectrum of the signal amplitude complicating feature. Additionally incorporated into this embodiment of the present invention is a correlation canceler having a signal input for receiving the first attenuation signal and a secondary reference input for receiving the secondary reference. The correlation canceler produces an output signal having a significant component which is derived from the component which is representative of a plethysmographic waveform. The apparatus may also include a reference processor for receiving the first and second light attenuation signals and deriving therefrom a primary reference. Additionally incorporated in this embodiment of the present invention is a correlation canceler having a signal input for receiving the first attenuation signal and a primary reference input for receiving the primary reference. The correlation canceler produces an output signal having a significant component which is derived from the component which is representative of the signal complicating feature.

The present invention also comprises a method of removing or determining a motion artifact signal from a signal derived from a physiological measurement wherein a first signal having a physiological measurement component and a motion artifact component and a second signal having a physiological measurement component and a motion artifact component are acquired. From the first and second signals a secondary reference which is a primary function of the first and second signals motion artifact components is derived. This method of removing a motion artifact signal from a signal derived from a physiological measurement may also comprise the step of inputting the secondary reference into a correlation canceler, such as an adaptive noise canceler, to produce an output signal which is a significant function of the physiological measurement component of the first or second signal. Alternatively, from the first and second signals a primary reference which is a significant function of the physiological measurement components of the first and second signals may be derived. This approach may also comprise the step of inputting the primary reference into a correlation canceler to produce an output signal which is a significant function of the first or second signal's motion artifact component.

BRIEF DESCRIPTION OF THE DRAWINGS

FIG. 5c illustrates the transfer function of a multiple notch filter.

FIG. 7c illustrates the non-ideal correlation canceler energy or power output as a function of the signal coefficients $\omega_1, \omega_2, \ldots \omega_n$. In this particular example, $\omega_3 = \omega_a$ and $\omega_7 = \omega_v$.

DETAILED DESCRIPTION OF THE PREFERRED EMBODIMENT

The present invention is a processor which determines either a secondary reference n'(t) or a primary reference s'(t) for use in a correlation canceler, such as an adaptive noise canceler. A correlation canceler may estimate a good approximation s"(t) to a primary signal s(t) from a composite signal S(t)=s(t)+n(t) which, in addition to the primary portion s(t) comprises a secondary portion n(t). It may also be used to provide a good approximation n"(t) to the secondary signal n(t). The secondary portion n(t) may contain one or more of a constant portion, a predictable portion, an erratic portion, a random portion, etc. The approximation to the primary signal s"(t) or secondary signal n"(t) is derived by removing as many of the secondary portions n(t) or primary portions s(t) from the composite signal S(t) as possible. The constant portion and predictable portion are easily removed with traditional filtering techniques, such as simple subtraction, low pass, band pass, and high pass filtering. The erratic portion is more difficult to remove due to its unpredictable nature. If something is known about the erratic signal, even statistically, it could be removed, at least partially, from the measured signal via traditional filtering techniques. However, it is often the case that no information is known about the erratic portion of the noise. In this case, traditional filtering techniques are usually insufficient. Often no information about the erratic portion of the measured signal is known. Thus, a correlation canceler, such as an adaptive noise canceler may be utilized in the present invention to remove or derive the erratic portion.

Generally, a correlation canceler has two signal inputs and one output. One of the inputs is either the secondary reference $n'(t)$ or the primary reference $s'(t)$ which are correlated, respectively, to the secondary signal portions $n(t)$ and the primary signal portions $s(t)$ present in the composite signal $S(t)$. The other input is for the composite signal $S(t)$. Ideally, the output of the correlation canceler $s''(t)$ or $n''(t)$ corresponds, respectively, to the primary signal $s(t)$ or the secondary signal $n(t)$ portions only. Often, the most difficult task in the application of correlation cancelers is determining the reference signals $n'(t)$ and $s'(t)$ which are correlated to the secondary $n(t)$ and primary $s(t)$ portions, respectively, of the measured signal $S(t)$ since, as discussed above, these portions are quite difficult to isolate from the measured signal $S(t)$. In the signal processor of the present invention, either a secondary reference $n'(t)$ or a primary reference $s'(t)$ is determined from two composite signals measured simultaneously, or nearly simultaneously, at two different wavelengths, $\lambda a$ and $\lambda b$.

Figure 1:
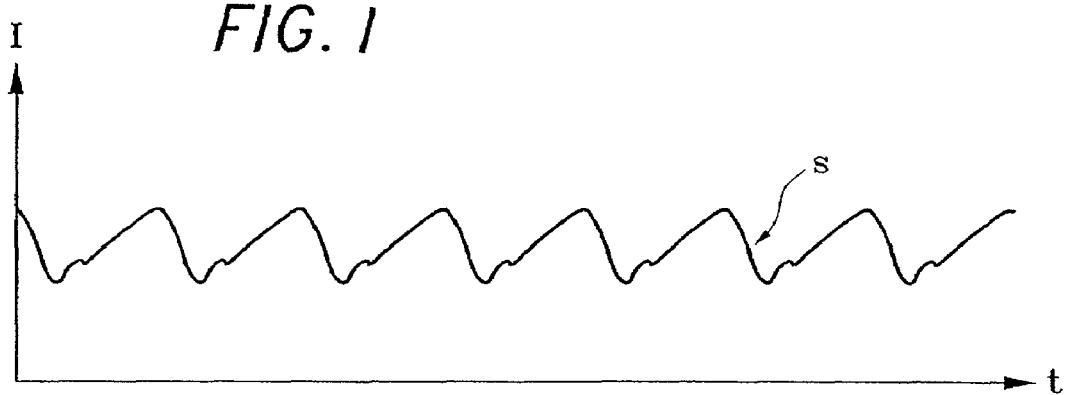
FIG. 1 illustrates an ideal plethysmographic waveform.
Figure 2:
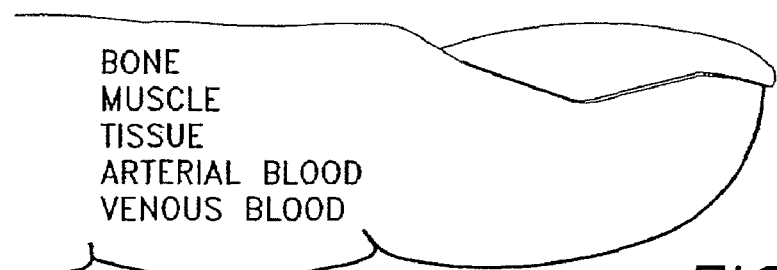
FIG. 2 schematically illustrates the cross-sectional structure of a typical finger.
Figure 3:
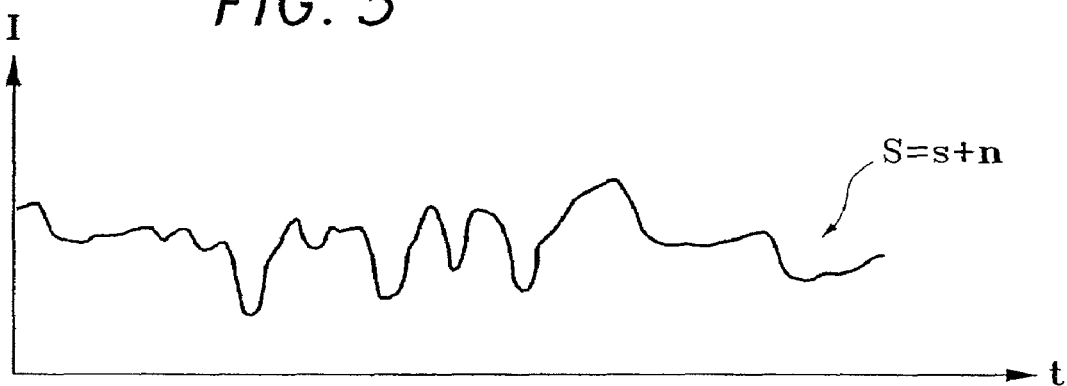
FIG. 3 illustrates a plethysmographic waveform which includes a motion-induced erratic signal portion.
Figure 4A:
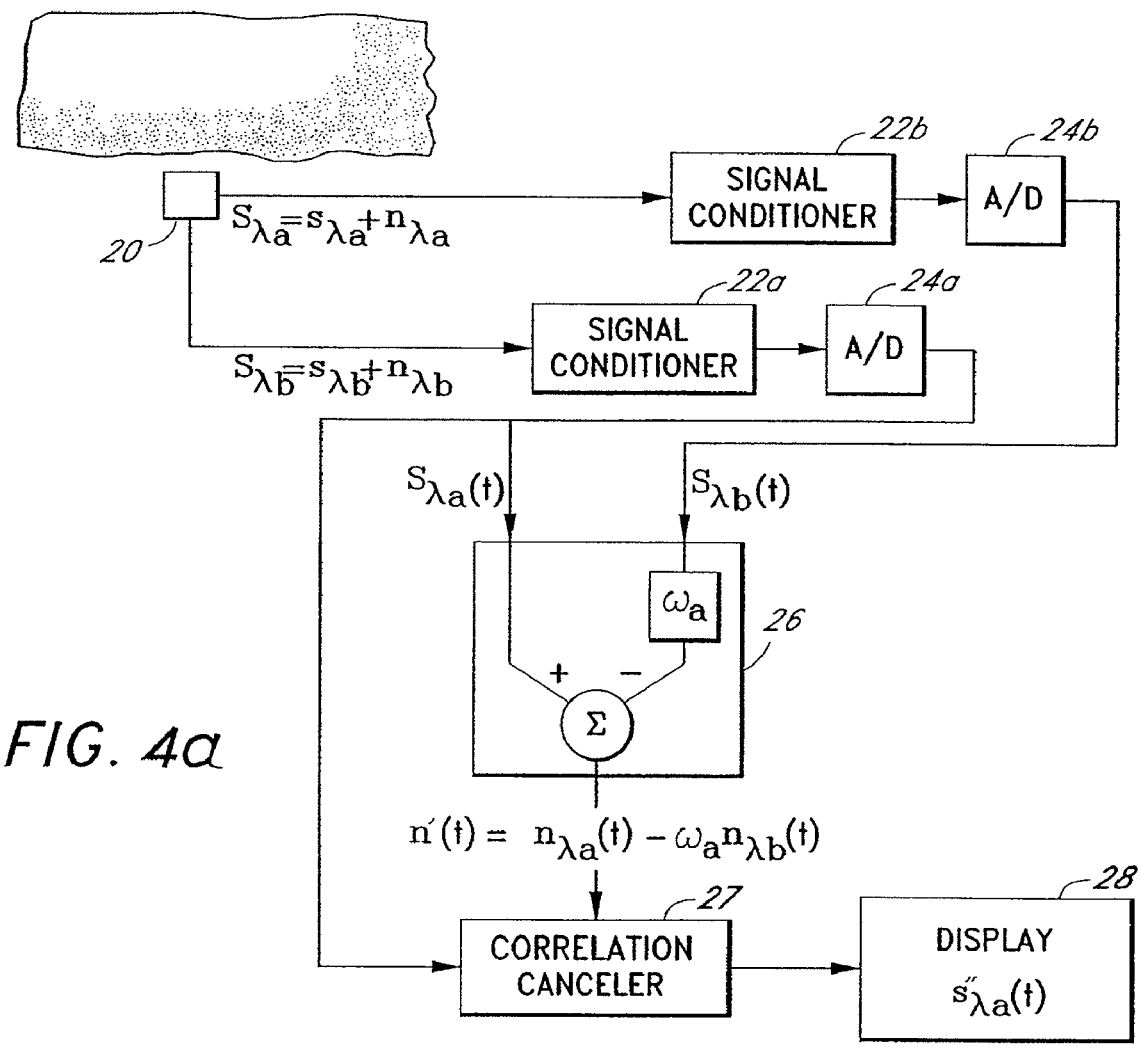
FIG. 4a illustrates a schematic diagram of a physiological monitor, to compute primary physiological signals, incorporating a processor of the present invention, and a correlation canceler.
Figure 4B:
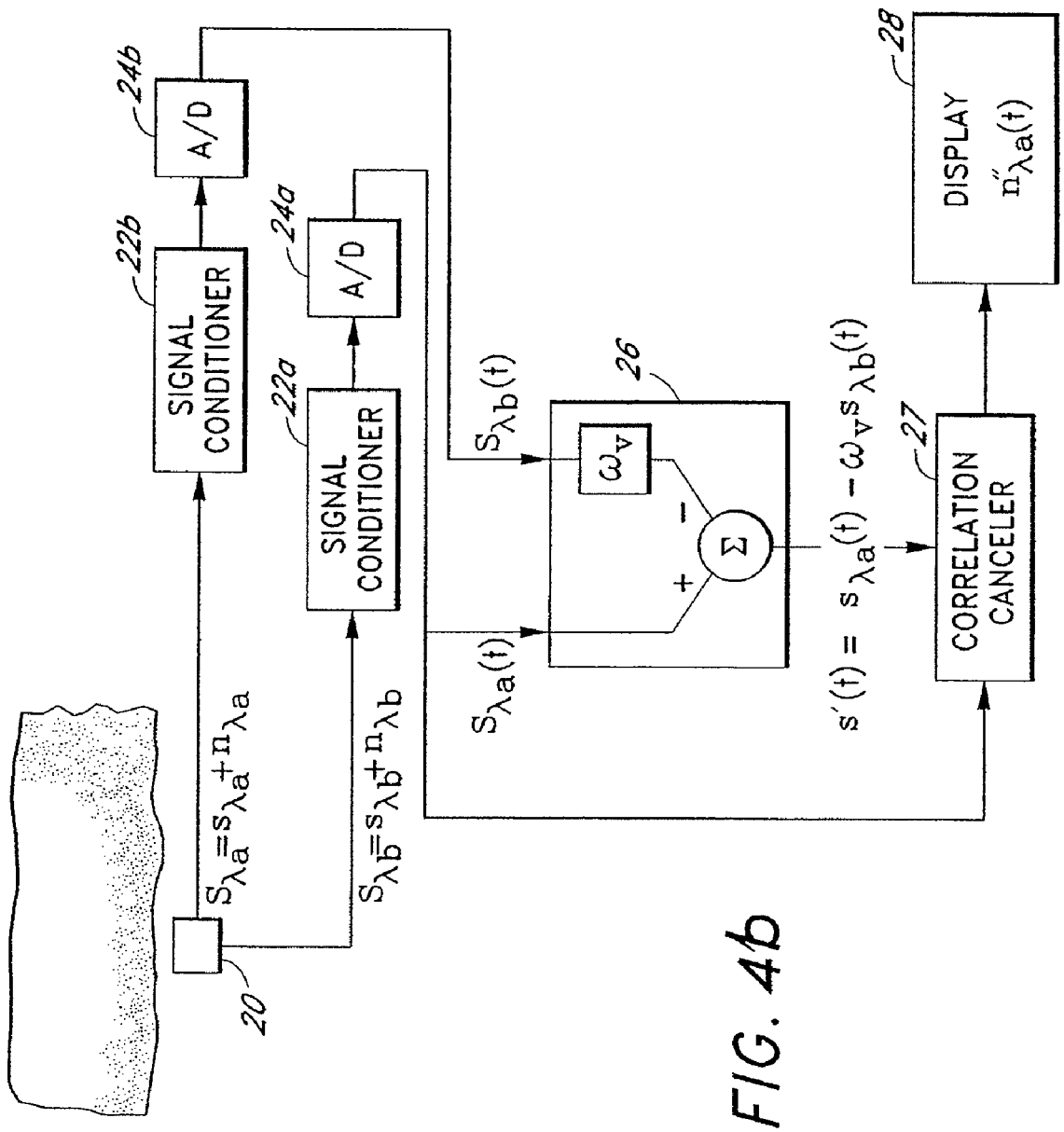
FIG. 4b illustrates a schematic diagram of a physiological monitor, to compute secondary erratic signals, incorporating a processor of the present invention, and a correlation canceler.

A block diagram of a generic monitor incorporating a signal processor, or reference processor, according to the present invention, and a correlation canceler is shown in FIGS. 4a and 4b. Two measured signals, $S_{\lambda,a}(t)$ and $S_{\lambda,b}(t)$, are acquired by a detector 20. One skilled in the art will realize that for some physiological measurements, more than one detector may be advantageous. Each signal is conditioned by a signal conditioner 22a and 22b. Conditioning includes, but is not limited to, such procedures as filtering the signals to remove constant portions and amplifying the signals for ease of manipulation. The signals are then converted to digital data by an analog-to-digital converter 24a and 24b. The first measured signal $S_{\lambda,a}(t)$ comprises a first primary signal portion, labeled herein $s_{\lambda,a}(t)$, and a first secondary signal portion, labeled herein $n_{\lambda,a}(t)$. The second measured signal $S_{\lambda,b}(t)$ is at least partially correlated to the first measured signal $S_{\lambda,a}(t)$ and comprises a second primary signal portion, labeled herein $s_{\lambda,b}(t)$, and a second secondary signal portion, labeled herein $n_{\lambda,b}(t)$. Typically the first and second secondary signal portions, $n_{\lambda,a}(t)$ and $n_{\lambda,b}(t)$, are uncorrelated and/or erratic with respect to the primary signal portions $s_{\lambda,a}(t)$ and $s_{\lambda,b}(t)$. The secondary signal portions $n_{\lambda,a}(t)$ and $n_{\lambda,b}(t)$ are often caused by motion of a patient. The signals $S_{\lambda,a}(t)$ and $S_{\lambda,b}(t)$ are input to a reference processor 26. The reference processor multiplies the second measured signal $S_{\lambda,b}(t)$ by either a factor $\omega_a = s_{\lambda,a}(t)/s_{\lambda,b}(t)$ or a factor $\omega_v = n_{\lambda,a}(t)/n_{\lambda,b}(t)$ and then subtracts the second measured signal $S_{\lambda,b}(t)$ from the first measured signal $S_{\lambda,a}(t)$. The signal coefficient factors $\omega_a$ and $\omega_v$ are determined to cause either the primary signal portions $s_{\lambda,a}(t)$ and $s_{\lambda,b}(t)$ or the secondary signal portions $n_{\lambda,a}(t)$ and $n_{\lambda,b}(t)$ to cancel when the two signals $S_{\lambda,a}(t)$ and $S_{\lambda,b}(t)$ are subtracted. Thus, the output of the reference processor 26 is either a secondary reference signal $n'(t) = n_{\lambda,a}(t) - \omega_a n_{\lambda,b}(t)$, in FIG. 4a, which is correlated to both of the secondary signal portions $n_{\lambda,a}(t)$ and $n_{\lambda,b}(t)$ or a primary reference signal $s'(t) = s_{\lambda,a}(t) - \omega_v s_{\lambda,b}(t)$, in FIG. 4b, which is correlated to both of the primary signal portions $s_{\lambda,a}(t)$ and $s_{\lambda,b}(t)$. A reference signal $n'(t)$ or $s'(t)$ is input, along with one of the measured signals $S_{\lambda,a}(t)$ or $S_{\lambda,b}(t)$, to a correlation canceler 27 which uses the reference signal $n'(t)$ or $s'(t)$ to remove either the secondary signal portions $n_{\lambda,a}(t)$ or $n_{\lambda,b}(t)$ or the primary signal portions $s_{\lambda,a}(t)$ or $s_{\lambda,b}(t)$ from the measured signal $S_{\lambda,a}(t)$ or $S_{\lambda,b}(t)$. The output of the correlation canceler 27 is a good approximation $s''(t)$ or $n''(t)$ to either the primary $s(t)$ or the secondary $n(t)$ signal components. The approximation $s''(t)$ or $n''(t)$ is displayed on the display 28.

Figure 5A:
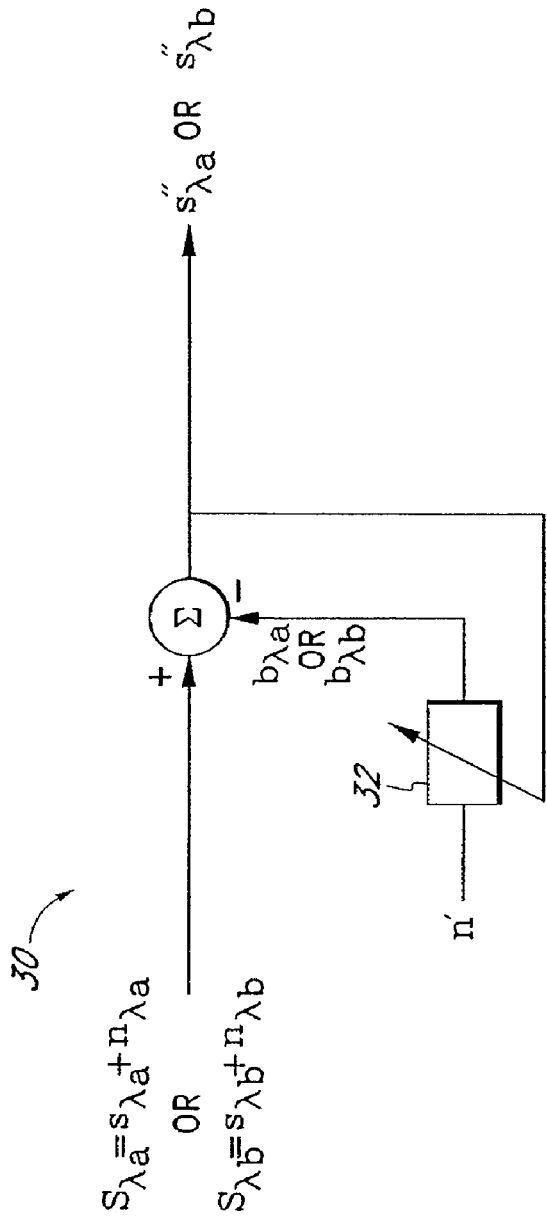
FIG. 5a illustrates an example of an adaptive noise canceler which could be employed in a physiological monitor, to compute primary physiological signals, which also incorporates the processor of the present invention.

An adaptive noise canceler 30, an example of which is shown in block diagram form in FIG. 5a, is employed to remove either one of the erratic, secondary signal portions $n_{\lambda,a}(t)$ and $n_{\lambda,b}(t)$ from the first and second signals $S_{\lambda,a}(t)$ and $S_{\lambda,b}(t)$. The adaptive noise canceler 30, which performs the functions of a correlation canceler, in FIG. 5a has as one input a sample of the secondary reference $n'(t)$ which is correlated to the secondary signal portions $n_{\lambda,a}(t)$ and $n_{\lambda,b}(t)$. The secondary reference $n'(t)$ is determined from the two measured signals $S_{\lambda,a}(t)$ and $S_{\lambda,b}(t)$ by the processor 26 of the present invention as described herein. A second input to the adaptive noise canceler, is a sample of either the first or second composite measured signals $S_{\lambda,a}(t) = s_{\lambda,a}(t) + n_{\lambda,a}(t)$ or $S_{\lambda,b}(t) = s_{\lambda,b}(t) + n_{\lambda,b}(t)$.

Figure 5B:
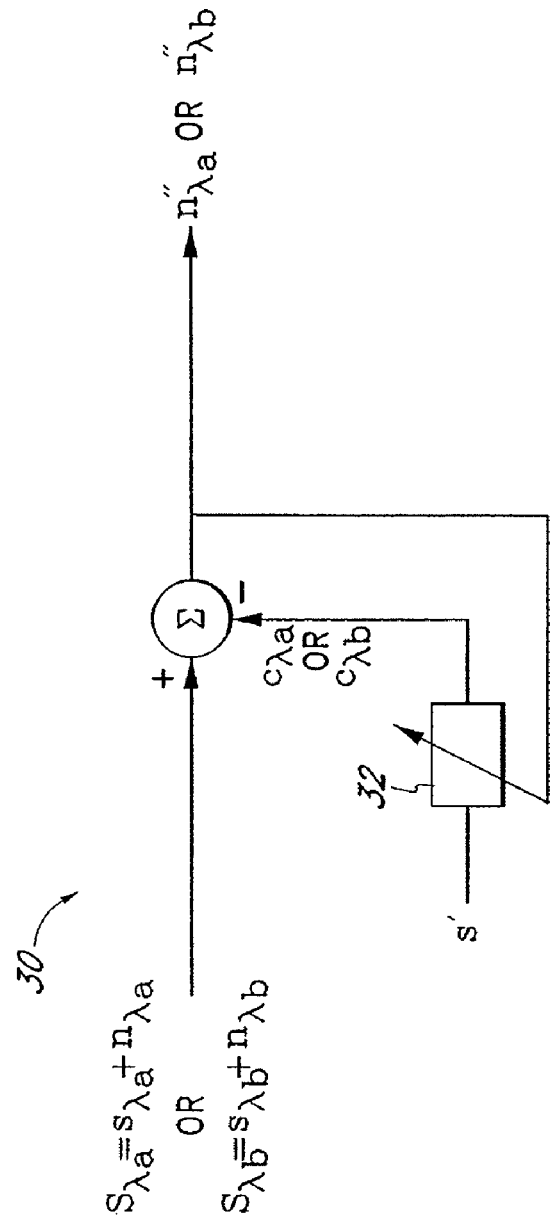
FIG. 5b illustrates an example of an adaptive noise canceler which could be employed in a physiological monitor, to compute secondary motion artifact signals, which also incorporates the processor of the present invention.

The adaptive noise canceler 30, in FIG. 5b, may also be employed to remove either one of primary signal portions $s_{\lambda,a}(t)$ and $s_{\lambda,b}(t)$ from the first and second signals $S_{\lambda,a}(t)$ and $S_{\lambda,b}(t)$. The adaptive noise canceler 30 has as one input a sample of the primary reference $s'(t)$ which is correlated to the primary signal portions $s_{\lambda,a}(t)$ and $s_{\lambda,b}(t)$. The primary reference $s'(t)$ is determined from the two measured signals $S_{\lambda,a}(t)$ and $S_{\lambda,b}(t)$ by the processor 26 of the present invention as described herein. A second input to the adaptive noise canceler 30 is a sample of either the first or second measured signals $S_{\lambda,a}(t) = s_{\lambda,a}(t) + n_{\lambda,a}(t)$ or $S_{\lambda,b}(t) = s_{\lambda,b}(t) + n_{\lambda,b}(t)$.

The adaptive noise canceler 30 functions to remove frequencies common to both the reference $n'(t)$ or $s'(t)$ and the measured signal $S_{\lambda,a}(t)$ or $S_{\lambda,b}(t)$. Since the reference signals are correlated to either the secondary signal portions $n_{\lambda,a}(t)$ and $n_{\lambda,b}(t)$ or the primary signal portions $s_{\lambda,a}(t)$ and $s_{\lambda,b}(t)$, the reference signals will be correspondingly erratic or well behaved. The adaptive noise canceler 30 acts in a manner which may be analogized to a dynamic multiple notch filter based on the spectral distribution of the reference signal $n'(t)$ or $s'(t)$.

Referring to FIG. 5c, the transfer function of a multiple notch filter is shown. The notches, or dips in the amplitude of the transfer function, indicate frequencies which are attenuated or removed when a composite measured signal passes through the notch filter. The output of the notch filter is the composite signal having frequencies at which a notch was present removed. In the analogy to an adaptive noise canceler 30, the frequencies at which notches are present change continuously based upon the inputs to the adaptive noise canceler 30.

The adaptive noise canceler 30 shown in FIGS. 5a and 5b produces an output signal, labeled herein as $s''_{\lambda,a}(t)$, $s''_{\lambda,b}(t)$, $n''_{\lambda,a}(t)$ or $n''_{\lambda,b}(t)$ which is fed back to an internal processor 32 within the adaptive noise canceler 30. The internal processor 32 automatically adjusts its own transfer function according to a predetermined algorithm such that the output of the internal processor 32, labeled $b(t)$ in FIG. 5a or $c(t)$ in FIG. 5b, closely resembles either the secondary signal portion $n_{\lambda,a}(t)$ or $n_{\lambda,b}(t)$ or the primary signal portion $s_{\lambda,a}(t)$ or $s_{\lambda,b}(t)$. The output $b(t)$ of the internal processor 32 in FIG. 5a is subtracted from the measured signal, $S_{\lambda,a}(t)$ or $S_{\lambda,b}(t)$, yielding a signal output $s''_{\lambda,a}(t) = s_{\lambda,a}(t) + n_{\lambda,a}(t) - b_{\lambda,a}(t)$ or a signal output $s''_{\lambda,b}(t) = s_{\lambda,b}(t) + n_{\lambda,b}(t) - b_{\lambda,b}(t)$. The internal processor optimizes $s''_{\lambda,a}(t)$ or $s''_{\lambda,b}(t)$ such that $s''_{\lambda,a}(t)$ or $s''_{\lambda,b}(t)$ is approximately equal to the primary signal $s_{\lambda,a}(t)$ or $s_{\lambda,b}(t)$, respectively. The output c(t) of the internal processor 32 in FIG. 5b is subtracted from the measured signal, $S_{\lambda a}(t)$ or $S_{\lambda b}(t)$, yielding a signal output given by $n''_{\lambda a}(t)=s_{\lambda a}(t)+n_{\lambda a}(t)-c_{\lambda a}(t)$ or a signal output given by $n''_{\lambda b}(t)=s_{\lambda b}(t)+n_{\lambda b}(t)-c_{\lambda b}(t)$. The internal processor optimizes $n''_{\lambda a}(t)$ or $n''_{\lambda b}(t)$ such that $n''_{\lambda a}(t)$ or $n''_{\lambda b}(t)$ is approximately equal to the secondary signal $n_{\lambda a}(t)$ or $n_{\lambda b}(t)$, respectively.

One algorithm which may be used for the adjustment of the transfer function of the internal processor 32 is a least-squares algorithm, as described in Chapter 6 and Chapter 12 of the book Adaptive Signal Processing by Bernard Widrow and Samuel Stearns, published by Prentice Hall, copyright 1985. This entire book, including Chapters 6 and 12, is hereby incorporated herein by reference.

Adaptive processors 30 in FIGS. 5a and 5b have been successfully applied to a number of problems including antenna sidelobe canceling, pattern recognition, the elimination of periodic interference in general, and the elimination of echoes on long distance telephone transmission lines. However, considerable ingenuity is often required to find a suitable reference signal n'(t) or s'(t) since the portions $n_{\lambda a}(t)$, $n_{\lambda b}(t)$, $s_{\lambda a}(t)$ and $s_{\lambda b}(t)$ cannot easily be separated from the measured signals $S_{\lambda a}(t)$ and $S_{\lambda b}(t)$. If either the actual secondary portion $n_{\lambda a}(t)$ or $n_{\lambda b}(t)$ or the primary signal portion $s_{\lambda a}(t)$ or $s_{\lambda b}(t)$ were a priori available, techniques such as correlation cancellation would not be necessary. The determination of a suitable reference signal n'(t) or s'(t) from measurements taken by a monitor incorporating a reference processor of the present invention is one aspect of the present invention.

Generalized Determination of Primary and Secondary Reference Signals

An explanation which describes how the reference signals n'(t) and s'(t) may be determined follows. A first signal is measured at, for example, a wavelength λa, by a detector yielding a signal $S_{\lambda a}(t)$:

$$S_{\lambda a}(t)=s_{\lambda a}(t)+n_{\lambda a}(t) \tag{1}$$

where $s_{\lambda a}(t)$ is the primary signal and $n_{\lambda a}(t)$ is the secondary signal.

A similar measurement is taken simultaneously, or nearly simultaneously, at a different wavelength, λb, yielding:

$$S_{\lambda b}(t)=s_{\lambda b}(t)+n_{\lambda b}(t) \tag{2}$$

Note that as long as the measurements, $S_{\lambda a}(t)$ and $S_{\lambda b}(t)$, are taken substantially simultaneously, the secondary signal components, $n_{\lambda a}(t)$ and $n_{\lambda b}(t)$, will be correlated because any random or erratic functions will affect each measurement in nearly the same fashion. The well behaved primary signal components, $s_{\lambda a}(t)$ and $s_{\lambda b}(t)$, will also be correlated to one another.

To obtain the reference signals n'(t) and s'(t), the measured signals $S_{\lambda a}(t)$ and $S_{\lambda b}(t)$ are transformed to eliminate, respectively, the primary or secondary signal components. One way of doing this is to find proportionality constants, $\omega_a$ and $\omega_v$, between the primary signals $s_{\lambda a}(t)$ and $s_{\lambda b}(t)$ and secondary signals $n_{\lambda a}(t)$ and $n_{\lambda b}(t)$ such that:

$$s_{\lambda a}(t)=\omega_a s_{\lambda b}(t)$$

$$n_{\lambda a}(t)=\omega_v n_{\lambda b}(t). \tag{3}$$

These proportionality relationships can be satisfied in many measurements, including but not limited to absorption measurements and physiological measurements. Additionally, in most measurements, the proportionality constants $\omega_a$ and $\omega_v$ can be determined such that:

$$n_{\lambda a}(t) \neq \omega_a n_{\lambda b}(t)$$

$$s_{\lambda a}(t) \neq \omega_v s_{\lambda b}(t). \tag{4}$$

Multiplying equation (2) by $\omega_a$ and then subtracting equation (2) from equation (1) results in a single equation wherein the primary signal terms $s_{\lambda a}(t)$ and $s_{\lambda b}(t)$ cancel, leaving:

$$n'(t)=S_{\lambda a}(t)-\omega_a S_{\lambda b}(t)=n_{\lambda a}(t)-\omega_a n_{\lambda b}(t); \tag{5a}$$

a non-zero signal which is correlated to each secondary signal portion $n_{\lambda a}(t)$ and $n_{\lambda b}(t)$ and can be used as the secondary reference n'(t) in a correlation canceler such as an adaptive noise canceler.

Multiplying equation (2) by $\omega_v$ and then subtracting equation (2) from equation (1) results in a single equation wherein the secondary signal terms $n_{\lambda a}(t)$ and $n_{\lambda b}(t)$ cancel, leaving:

$$s'(t)=S_{\lambda a}(t)-\omega_v S_{\lambda b}(t)=s_{\lambda a}(t)-\omega_v s_{\lambda b}(t); \tag{5b}$$

a non-zero signal which is correlated to each of the primary signal portions $s_{\lambda a}(t)$ and $s_{\lambda b}(t)$ and can be used as the signal reference s'(t) in a correlation canceler such as an adaptive noise canceler.

Example of Determination of Primary and Secondary Reference Signals in an Absorptive System Correlation canceling is particularly useful in a large number of measurements generally described as absorption measurements. An example of an absorption type monitor which can advantageously employ correlation canceling, such as adaptive noise canceling, based upon a reference n'(t) or s'(t) determined by a processor of the present invention is one which determines the concentration of an energy absorbing constituent within an absorbing material when the material is subject to change. Such changes can be caused by forces about which information is desired or primary, or alternatively, by random or erratic secondary forces such as a mechanical force on the material. Random or erratic interference, such as motion, generates secondary components in the measured signal. These secondary components can be removed or derived by the correlation canceler if a suitable secondary reference n'(t) or primary reference s'(t) is known.

Figure 6A:
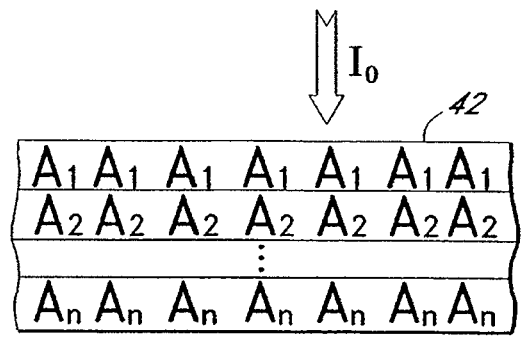
FIG. 6a illustrates a schematic absorbing material comprising N constituents within an absorbing material.

A schematic N constituent absorbing material comprising a container 42 having N different absorbing constituents, labeled $A_1, A_2, A_3, \ldots A_N$, is shown schematically in FIG. 6a. The constituents $A_1$ through $A_N$ in FIG. 6a are arranged in a generally orderly, layered fashion within the container 42. An example of a particular type of absorptive system is one in which light energy passes through the container 42 and is absorbed according to the generalized Beer-Lambert Law of light absorption. For light of wavelength λa, this attenuation may be approximated by:

$$I = I_o \exp\left(-\sum_{i=1}^{N} \epsilon_{i,\lambda a}\, c_i x_i\right) \tag{6}$$

Initially transforming the signal by taking the natural logarithm of both sides and manipulating terms, the signal is transformed such that the signal components are combined by addition rather than multiplication, i.e.:

$$S_{\lambda a} = \ln(I_0/I) = \sum_{i=1}^{N} \epsilon_{i,\lambda a} c_i x_i \quad (7)$$

where $I_0$ is the incident light energy intensity; I is the transmitted light energy intensity; $\epsilon_{i,\lambda a}$ is the absorption coefficient of the $i^{th}$ constituent at the wavelength $\lambda a$; $x_i(t)$ is the optical path length of $i^{th}$ layer, i.e., the thickness of material of the $i^{th}$ layer through which optical energy passes; and $c_i(t)$ is the concentration of the $i^{th}$ constituent in the volume associated with the thickness $x_i(t)$. The absorption coefficients $\epsilon_1$ through $\epsilon_N$ are known values which are constant at each wavelength. Most concentrations $c_1(t)$ through $c_N(t)$ are typically unknown, as are most of the optical path lengths $x_i(t)$ of each layer. The total optical path length is the sum of each of the individual optical path lengths $x_i(t)$ of each layer.

When the material is not subject to any forces which cause change in the thicknesses of the layers, the optical path length of each layer, $x_i(t)$, is generally constant. This results in generally constant attenuation of the optical energy and thus, a generally constant offset in the measured signal. Typically, this portion of the signal is of little interest since knowledge about a force which perturbs the material is usually desired. Any signal portion outside of a known bandwidth of interest, including the constant undesired signal portion resulting from the generally constant absorption of the constituents when not subject to change, should be removed. This is easily accomplished by traditional band pass filtering techniques. However, when the material is subject to forces, each layer of constituents may be affected by the perturbation differently than each other layer. Some perturbations of the optical path lengths of each layer $x_i(t)$ may result in excursions in the measured signal which represent desired or primary information. Other perturbations of the optical path length of each layer $x_i(t)$ cause undesired or secondary excursions which mask primary information in the measured signal. Secondary signal components associated with secondary excursions must also be removed to obtain primary information from the measured signal. Similarly, the ability to compute secondary signal components caused by secondary excursions directly allows one to obtain primary signal components from the measured signal via simple subtraction, or correlation cancellation techniques.

The correlation canceler may selectively remove from the composite signal, measured after being transmitted through or reflected from the absorbing material, either the secondary or the primary signal components caused by forces which perturb or change the material differently from the forces which perturbed or changed the material to cause respectively, either the primary or secondary signal component. For the purposes of illustration, it will be assumed that the portion of the measured signal which is deemed to be the primary signal $s_{\lambda a}(t)$ is the attenuation term $\epsilon_5 c_5 x_5(t)$ associated with a constituent of interest, namely $A_5$, and that the layer of constituent $A_5$ is affected by perturbations different than each of the layers of other constituents $A_1$ through $A_4$ and $A_6$ through $A_N$. An example of such a situation is when layer $A_5$ is subject to forces about which information is deemed to be primary and, additionally, the entire material is subject to forces which affect each of the layers. In this case, since the total force affecting the layer of constituent $A_5$ is different than the total forces affecting each of the other layers and information is deemed to be primary about the forces and resultant perturbation of the layer of constituent $A_5$, attenuation terms due to constituents $A_1$ through $A_4$ and $A_6$ through $A_N$ make up the secondary signal portion $n_{\lambda a}(t)$. Even if the additional forces which affect the entire material cause the same perturbation in each layer, including the layer of $A_5$, the total forces on the layer of constituent $A_5$ cause it to have different total perturbation than each of the other layers of constituents $A_1$ through $A_4$ and $A_6$ through $A_N$.

It is often the case that the total perturbation affecting the layers associated with the secondary signal components is caused by random or erratic forces. This causes the thickness of layers to change erratically and the optical path length of each layer, $x_i(t)$, to change erratically, thereby producing a random or erratic secondary signal component $n_{\lambda a}(t)$. However, regardless of whether or not the secondary signal portion $n_{\lambda a}(t)$ is erratic, the secondary signal component $n_{\lambda a}(t)$ can be either removed or derived via a correlation canceler, such as an adaptive noise canceler, having as one input, respectively, a secondary reference n'(t) or a primary reference s'(t) determined by a processor of the present invention as long as the perturbation on layers other than the layer of constituent $A_5$ is different than the perturbation on the layer of constituent $A_5$. The correlation canceler yields a good approximation to either the primary signal $s_{\lambda a}(t)$ or the secondary signal $n_{\lambda a}(t)$. In the event that an approximation to the primary signal is obtained, the concentration of the constituent of interest, $c_5(t)$, can often be determined since in some physiological measurements, the thickness of the primary signal component, $x_5(t)$ in this example, is known or can be determined.

The correlation canceler utilized a sample of either the secondary reference n'(t) or the primary reference s'(t) determined from two substantially simultaneously measured signals $S_{\lambda a}(t)$ and $S_{\lambda b}(t)$. $S_{\lambda a}(t)$ is determined as above in equation (7). $S_{\lambda b}(t)$ is determined similarly at a different wavelength $\lambda b$. To find either the secondary reference n'(t) or the primary reference s'(t), attenuated transmitted energy is measured at the two different wavelengths $\lambda a$ and $\lambda b$ and transformed via logarithmic conversion. The signals $S_{\lambda a}(t)$ and $S_{\lambda b}(t)$ can then be written (logarithm converted) as:

$$S_{\lambda a}(t) = \epsilon_{5,\lambda a} c_5 x_5(t) + \sum_{i=1}^{4} \epsilon_{i,\lambda a} c_i x_i + \sum_{i=6}^{N} \epsilon_{i,\lambda a} c_i x_i \quad (8)$$

$$S_{\lambda a(t)} = \epsilon_{5,\lambda a} c_5 x_5(t) + n_{\lambda a}(t) \quad (9)$$

$$S_{\lambda b(t)} = \epsilon_{5,\lambda b} c_5 x_5(t) + \sum_{i=1}^{4} \epsilon_{i,\lambda b} c_i x_i + \sum_{i=6}^{N} \epsilon_{i,\lambda b} c_i x_i \quad (10)$$

$$S_{\lambda b(t)} = \epsilon_{5,\lambda b} c_5 x_5(t) + n_{\lambda b}(t) \quad (11)$$

Further transformations of the signals are the proportionality relationships defining $\omega_a$ and $\omega_v$, similarly to equation (3), which allows determination of a noise reference n'(t) and a primary reference s'(t). These are:

$$\epsilon_{5,\lambda a} = \omega_a \epsilon_{5,\lambda b} \quad (12a)$$

$$n_{\lambda a} = \omega_v n_{\lambda b} \quad (12b)$$

where $$n_{\lambda a} \neq \omega_a n_{\lambda b} \quad (13a)$$

$$\epsilon_{5,\lambda a} \neq \omega_v \epsilon_{5,\lambda b} \quad (13b)$$

It is often the case that both equations (12) and (13) can be simultaneously satisfied. Multiplying equation (11) by $\omega_a$ and subtracting the result from equation (9) yields a non-zero secondary reference which is a linear sum of secondary signal components:

$$n'(t) = S_{\lambda a}(t) - \omega_a S_{\lambda b}(t) = n_{\lambda a}(t) - \omega_a n_{\lambda b}(t) \qquad (14a)$$

$$= \sum_{i=1}^{4} \epsilon_{i,\lambda a} \, c_i x_i(t) + \sum_{i=6}^{N} \epsilon_{i,\lambda a} \qquad (15a)$$

$$c_i x_i(t) - \sum_{i=1}^{4} \omega_a \, \epsilon_{i,\lambda b} \, c_i x_i(t) + \sum_{i=6}^{N} \omega_a \, \epsilon_{i,\lambda b} \, c_i x_i(t)$$

$$= \sum_{i=1}^{4} c_i x_i(t)[\epsilon_{i,\lambda a} - \omega_a \, \epsilon_{i,\lambda b}] + \sum_{i=6}^{N} c_i x_i(t)[\epsilon_{i,\lambda a} - \omega_a \, \epsilon_{i,\lambda b}] \qquad (16a)$$

Multiplying equation (11) by $\omega_v$ and subtracting the result from equation (9) yields a primary reference which is a linear sum of primary signal components:

$$s'(t) = S_{\lambda a}(t) - \omega_v S_{\lambda b}(t) = s_{\lambda a}(t) - \omega_v s_{\lambda b}(t) \qquad (14b)$$

$$= c_5 x_5(t) \varepsilon_{5,\lambda a} - \omega_v c_5 x_5(t) \varepsilon_{5,\lambda b} \qquad (15b)$$

$$= c_5 x_5(t)[\varepsilon_{5,\lambda a} - \omega_v \varepsilon_{5,\lambda b}]. \qquad (16b)$$

A sample of either the secondary reference n'(t) or the primary reference s'(t), and a sample of either measured signal $S_{\lambda a}(t)$ or $S_{\lambda b}(t)$, are input to a correlation canceler 27, such as an adaptive noise canceler 30, an example of which is shown in FIGS. 5a and 5b and a preferred example of which is discussed herein under the heading PREFERRED CORRELATION CANCELER USING A JOINT PROCESS ESTIMATOR IMPLEMENTATION. The correlation canceler 27 removes either the secondary portion $n_{\lambda a}(t)$ or $n_{\lambda b}(t)$, or the primary portions, $s_{\lambda a}(t)$ or $s_{\lambda b}(t)$, of the measured signal yielding a good approximation to either the primary signals $s''_{\lambda a}(t) \approx \epsilon_{5,\lambda a} c_5 x_5(t)$ or $s''_{\lambda b}(t) \approx \epsilon_{5,\lambda b} c_5 x_5(t)$ or the secondary signals $n''_{\lambda a}(t) \approx n_{\lambda a}(t)$ or $n''_{\lambda b}(t) \approx n_{\lambda b}(t)$. In the event that the primary signals are obtained, the concentration $c_5(t)$ may then be determined from the approximation to the primary signal $s''_{\lambda a}(t)$ or $s''_{\lambda b}(t)$ according to:

$$c_5(t) \approx s''_{\lambda a}(t)/\epsilon_{5,\lambda a} x_5(t) c_5(t) \approx s''_{\lambda b}(t)/\epsilon_{5,\lambda b} x_5(t) \qquad (17)$$

As discussed previously, the absorption coefficients are constant at each wavelength λa and λb and the thickness of the primary signal component, $x_5(t)$ in this example, is often known or can be determined as a function of time, thereby allowing calculation of the concentration $c_5(t)$ of constituent $A_5$.

Figure 6B:
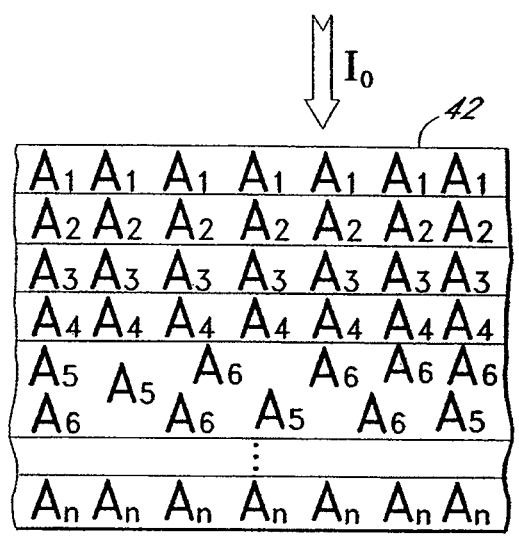
FIG. 6b illustrates another schematic absorbing material comprising N constituents, including one mixed layer, within an absorbing material.

Determination of Concentration or Saturation in a Volume Containing More than One Constituent Referring to FIG. 6b, another material having N different constituents arranged in layers is shown. In this material, two constituents $A_5$ and $A_6$ are found within one layer having thickness $x_{5,6}(t)=x_5(t)+x_6(t)$, located generally randomly within the layer. This is analogous to combining the layers of constituents $A_5$ and $A_6$ in FIG. 6a. A combination of layers, such as the combination of layers of constituents $A_5$ and $A_6$, is feasible when the two layers are under the same total forces which result in the same change of the, optical path lengths $x_5(t)$ and $x_6(t)$ of the layers.

Often it is desirable to find the concentration or the saturation, i.e., a percent concentration, of one constituent within a given thickness which contains more than one constituent and is subject to unique forces. A determination of the concentration or the saturation of a constituent within a given volume may be made with any number of constituents in the volume subject to the same total forces and therefore under the same perturbation or change. To determine the saturation of one constituent in a volume comprising many constituents, as many measured signals as there are constituents which absorb incident light energy are necessary. It will be understood that constituents which do not absorb light energy are not consequential in the determination of saturation. To determine the concentration, as many signals as there are constituents which absorb incident light energy are necessary as well as information about the sum of concentrations.

It is often the case that a thickness under unique motion contains only two constituents. For example, it may be desirable to know the concentration or saturation of $A_5$ within a given volume which contains $A_5$ and $A_6$. In this case, the primary signals $s_{\lambda a}(t)$ and $s_{\lambda b}(t)$ comprise terms related to both $A_5$ and $A_6$ so that a determination of the concentration or saturation of $A_5$ or $A_6$ in the volume may be made. A determination of saturation is discussed herein. It will be understood that the concentration of $A_5$ in a volume containing both $A_5$ and $A_6$ could also be determined if it is known that $A_5+A_6=1$, i.e., that there are no constituents in the volume which do not absorb incident light energy at the particular measurement wavelengths chosen. Then measured signals $S_{\lambda a}(t)$ and $S_{\lambda b}(t)$ can be written (logarithm converted) as:

$$S_{\lambda a}(t) = \varepsilon_{5,\lambda a} c_5 x_{5,6}(t) + \varepsilon_{6,\lambda a} c_6 x_{5,6}(t) + n_{\lambda a}(t) \qquad (18a)$$

$$= s_{\lambda a}(t) + n_{\lambda a}(t); \qquad (18b)$$

$$S_{\lambda b}(t) = \varepsilon_{5,\lambda b} c_5 x_{5,6}(t) + \varepsilon_{6,\lambda b} c_6 x_{5,6}(t) + m_{\lambda b}(t) \qquad (19a)$$

$$= s_{\lambda b}(t) + n_{\lambda b}(t). \qquad (19b)$$

Figure 6C:
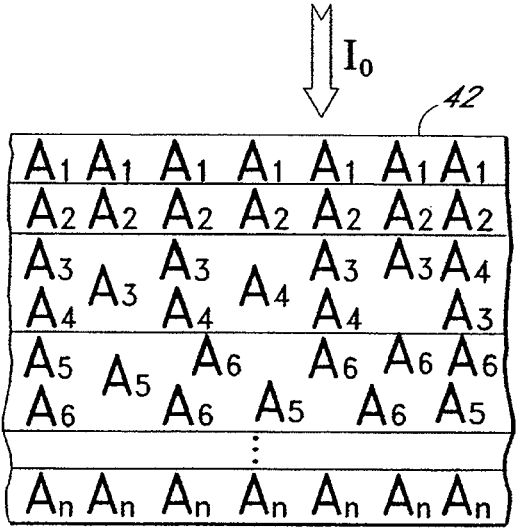
FIG. 6c illustrates another schematic absorbing material comprising N constituents, including two mixed layers, within an absorbing material.

It is also often the case that there may be two or more thicknesses within a medium each containing the same two constituents but each experiencing a separate motion as in FIG. 6c. For example, it may be desirable to know the concentration or saturation of $A_5$ within a given volume which contains $A_5$ and $A_6$ as well as the concentration or saturation of $A_3$ within a given volume which contains $A_3$ and $A_4$, $A_3$ and $A_4$ having the same constituency as $A_5$ and $A_6$, respectively. In this case, the primary signals $s_{\lambda a}(t)$ and $s_{\lambda b}(t)$ again comprise terms related to both $A_5$ and $A_6$ and portions of the secondary signals $n_{\lambda a}(t)$ and $n_{\lambda b}(t)$ comprise terms related to both $A_3$ and $A_4$. The layers, $A_3$ and $A_4$, do not enter into the primary equation because they are assumed to be perturbed by random or erratic secondary forces which are uncorrelated with the primary force. Since constituents 3 and 5 as well as constituents 4 and 6 are taken to be the same, they have the same absorption coefficients. i.e. $\epsilon_{3,\lambda a}=\epsilon_{5,\lambda a}$, $\epsilon_{3,\lambda b}=\epsilon_{5,\lambda b}$, $\epsilon_{4,\lambda a}=\epsilon_{6,\lambda a}$ and $\epsilon_{4,\lambda b}=\epsilon_{6,\lambda b}$. Generally speaking, however, $A_3$ and $A_4$ will have different concentrations than $A_5$ and $A_6$ and will therefore have a different saturation. Consequently a single constituent within a medium may have one or more saturations associated with it. The primary and secondary signals according to this model may be written as:

$$s_{\lambda a}(t) = [\varepsilon_{5,\lambda a} c_5 + \varepsilon_{6,\lambda a} c_6] x_{5,6}(t) \quad (20a)$$
$$n_{\lambda a}(t) = [\varepsilon_{5,\lambda a} c_3 + \varepsilon_{6,\lambda a} c_4] x_{3,4}(t)$$

$$+ \sum_{i=1}^{2} \epsilon_{i,\lambda a} c_i x_i(t) + \sum_{i=7}^{n} \epsilon_{i,\lambda a} c_i x_i(t) \quad (20b)$$

$$n_{\lambda a}(t) = [\varepsilon_{5,\lambda a} c_3 + \varepsilon_{6,\lambda a} c_4] x_{3,4}(t) + n_{\lambda a}(t) \quad (20c)$$

$$s_{\lambda b}(t) = [\varepsilon_{5,\lambda b} c_5 + \varepsilon_{6,\lambda b} c_6] x_{5,6}(t) \quad (21a)$$
$$n_{\lambda b}(t) = [\varepsilon_{5,\lambda b} c_3 + \varepsilon_{6,\lambda b} c_4] x_{3,4}(t)$$

$$+ \sum_{i=1}^{2} \epsilon_{i,\lambda b} c_i x_i(t) + \sum_{i=7}^{N} \epsilon_{i,\lambda b} c_i x_i(t). \quad (21b)$$

$$n_{\lambda b}(t) = [\varepsilon_{5,\lambda b} c_3 + \varepsilon_{6,\lambda b} c_4] x_{3,4}(t) + n_{\lambda b}(t) \quad (21c)$$

where signals $n_{\lambda a}(t)$ and $n_{\lambda b}(t)$ are similar to the secondary signals $n_{\lambda a}(t)$ and $n_{\lambda b}(t)$ except for the omission of the 3, 4 layer.

Any signal portions whether primary or secondary, outside of a known bandwidth of interest, including the constant undesired secondary signal portion resulting from the generally constant absorption of the constituents when not under perturbation, should be removed to determine an approximation to either the primary signal or the secondary signal within the bandwidth of interest. This is easily accomplished by traditional band pass filtering techniques. As in the previous example, it is often the case that the total perturbation or change affecting the layers associated with the secondary signal components is caused by random or erratic forces, causing the thickness of each layer, or the optical path length of each layer, $x_i(t)$, to change erratically, producing a random or erratic secondary signal component $n_{\lambda a}(t)$. Regardless of whether or not the secondary signal portion $n_{\lambda a}(t)$ is erratic, the secondary signal component $n_{\lambda a}(t)$ can be removed or derived via a correlation canceler, such as an adaptive noise canceler, having as one input a secondary reference n'(t) or a primary reference s'(t) determined by a processor of the present invention as long as the perturbation in layers other than the layer of constituents $A_5$ and $A_6$ is different than the perturbation in the layer of constituents $A_5$ and $A_6$. Either the erratic secondary signal components $n_{\lambda a}(t)$ and $n_{\lambda b}(t)$ or the primary components $s_{\lambda a}(t)$ and $s_{\lambda b}(t)$ may advantageously be removed from equations (18) and (19), or alternatively equations (20) and (21), by a correlation canceler. The correlation canceler, again, requires a sample of either the primary reference s'(t) or the secondary reference n'(t) and a sample of either of the composite signals $S_{\lambda a}(t)$ or $S_{\lambda b}(t)$ of equations (18) and (19).

Determination of Primary and Secondary Reference Signals for Saturation Measurements Two methods which may be used by a processor of the present invention to determine either the secondary reference n'(t) or the primary reference s'(t) are a ratiometric method and a constant saturation method. One embodiment of a physiological monitor incorporating a processor of the present invention utilizes the ratiometric method wherein the two wavelengths $\lambda a$ and $\lambda b$, at which the signals $S_{\lambda a}(t)$ and $S_{\lambda b}(t)$ are measured, are specifically chosen such that a relationship between the absorption coefficients $\epsilon_{5,\lambda a}, \epsilon_{5,\lambda b}, \epsilon_{6,\lambda a}$ and $\epsilon_{6,\lambda b}$ exists, i.e.:

$$\frac{\varepsilon_{5,\lambda b}}{\varepsilon_{6,\lambda b}} = \frac{\varepsilon_{5,\lambda a}}{\varepsilon_{6,\lambda a}} \quad (22)$$

The measured signals $S_{\lambda a}(t)$ and $S_{\lambda b}(t)$ can be factored and written as:

$$S_{\lambda_a}(t) = \varepsilon_{6,\lambda a}\left[\left(\frac{\varepsilon_{5,\lambda a}}{\varepsilon_{6,\lambda a}}\right) c_5 x_{5,6}(t) + c_6 x_{5,6}(t)\right] + n\lambda_a(t) \quad (23a)$$

$$S_{\lambda_a}(t) = \varepsilon_{6,\lambda a}\left[\begin{array}{l}\left(\frac{\varepsilon_{5,\lambda a}}{\varepsilon_{6,\lambda a}}\right) c_5 x_{5,6}(t) + c_6 x_{5,6}(t) + \\ \left(\frac{\varepsilon_{5,\lambda a}}{\varepsilon_{6,\lambda a}}\right) c_3 x_{3,4}(t) + c_4 x_{3,4}(t)\end{array}\right] + n\lambda_a(t) \quad (23b)$$

$$S_{\lambda_a}(t) = s_{\lambda_a}(t) + n_{\lambda_a}(t) \quad (23c)$$

$$S_{\lambda_b}(t) = \varepsilon_{6,\lambda b}\left[\left(\frac{\varepsilon_{5,\lambda b}}{\varepsilon_{6,\lambda b}}\right) c_5 x_{5,6}(t) + c_6 x_{5,6}(t)\right] + n\lambda_b(t) \quad (24a)$$

$$S_{\lambda_b}(t) = \varepsilon_{6,\lambda b}\left[\begin{array}{l}\left(\frac{\varepsilon_{5,\lambda b}}{\varepsilon_{6,\lambda b}}\right) c_5 x_{5,6}(t) + c_6 x_{5,6}(t) + \\ \left(\frac{\varepsilon_{5,\lambda b}}{\varepsilon_{6,\lambda b}}\right) c_3 x_{3,4}(t) + c_4 x_{3,4}(t)\end{array}\right] + n\lambda_b(t) \quad (24b)$$

$$S_{\lambda_b}(t) = s_{\lambda_b}(t) + n_{\lambda_b}(t) \quad (24c)$$

The wavelengths $\lambda a$ and $\lambda b$, chosen to satisfy equation (22), cause the terms within the square brackets to be equal, thereby causing the terms other than $n_{\lambda a}(t)$ and $n_{\lambda b}(t)$ to be linearly dependent. Then, proportionality constants $\omega_{av}$ and $\omega_e$ may be found for the determination of a non-zero primary and secondary reference $$\epsilon_{6,\lambda n} = \omega_{av} \epsilon_{6,\lambda b} \quad (25a)$$

$$n_{\lambda n}(t) = \omega_e n_{\lambda b}(t) \quad (25b)$$

$$\epsilon_{6,\lambda n} \approx \omega_e \epsilon_{6,\lambda b} \quad (25a)$$

$$n_{\lambda n}(t) \approx \omega_{av} n_{\lambda b}(t) \quad (26b)$$

It is often the case that both equations (25) and (26) can be simultaneously satisfied. Additionally, since the absorption coefficients of each constituent are constant with respect to wavelength, the proportionality constants $\omega_a v$ and $\omega_e$ can be easily determined. Furthermore, absorption coefficients of other constituents $A_1$ through $A_2$ and $A_7$ through $A_N$ are generally unequal to the absorption coefficients of $A_3, A_4, A_5$ and $A_6$. Thus, the secondary components $n_{\lambda a}$ and $n_{\lambda b}$ are generally not made linearly dependent by the relationships of equations (22) and (25).

Multiplying equation (24) by $\omega_a v$ and subtracting the resulting equation from equation (23), a non-zero secondary reference is determined by:

$$n(t) = S_{\lambda a}(t) - \omega_{av} S_{\lambda b}(t) = n_{\lambda a}(t) - \omega_{av} n_{\lambda b}(t). \quad (27a)$$

Multiplying equation (24) by $\omega_e$ and subtracting the resulting equation from equation (23), a non-zero primary reference is determined by:

$$s(t) = S_{\lambda a}(t) - \omega_e S_{\lambda b}(t) = s_{\lambda a}(t) - \omega_e s_{\lambda b}(t). \quad (27b)$$

An alternative method for determining reference signals from the measured signals $S_{\lambda a}(t)$ and $S_{\lambda b}(t)$ using a processor of the present invention is the constant saturation approach. In this approach, it is assumed that the saturation of $A_5$ in the volume containing $A_5$ and $A_6$ and the saturation of $A_3$ in the volume containing $A_3$ and $A_4$ remains relatively constant over some period of time, i.e.:

$$\text{Saturation}(A_5(t))=c_5(t)/[c_5(t)+c_6(t)] \quad (28a)$$

$$\text{Saturation}(A_3(t))=c_3(t)/[c_3(t)+c_4(t)] \quad (28b)$$

$$\text{Saturation}(A_5(t))=\{1+[c_6(t)/c_5(t)]\}^{-1} \quad (29a)$$

$$\text{Saturation}(A_3(t))=\{1+[c_4(t)/c_3(t)]\}^{-1} \quad (29b)$$

are substantially constant over many samples of the measured signals $S_{\lambda a}$ and $S_{\lambda b}$. This assumption is accurate over many samples since saturation generally changes relatively slowly in physiological systems.

The constant saturation assumption is equivalent to assuming that:

$$c_5(t)/c_6(t)=\text{constant}_1 \quad (30a)$$

$$c_3(t)/c_4(t)=\text{constant}_2 \quad (30b)$$

since the only other term in equations (29a) and (29b) is a constant, namely the numeral 1.

Using this assumption, the proportionality constants $\omega_a$ and $\omega_v$ which allow determination of the secondary reference signal $n'(t)$ and the primary reference signal $s'(t)$ in the constant saturation method are:

$$\omega_v = \frac{\varepsilon_{5,\lambda a} c_5 x_{5,6}(t) + \varepsilon_{6,\lambda a} c_6 x_{5,6}(t)}{\varepsilon_{5,\lambda b} c_5 x_{5,6}(t) + \varepsilon_{6,\lambda b} c_6 x_{5,6}(t)} \quad (31a)$$

$$= s_{\lambda a}(t)/s_{\lambda b}(t) \quad (32a)$$

$$= \frac{\varepsilon_{5,\lambda a} c_5 + \varepsilon_{6,\lambda a} c_6}{\varepsilon_{5,\lambda b} c_5 + \varepsilon_{6,\lambda b} c_6} \quad (33a)$$

$$= \frac{\varepsilon_{5,\lambda a}(c_5/c_6) + \varepsilon_{6,\lambda a}}{\varepsilon_{5,\lambda b}(c_5/c_6) + \varepsilon_{6,\lambda b}} \quad (34a)$$

$$\approx s''_{\lambda a}(t)/s''_{\lambda b}(t) = \text{constant}_3; \quad (35a)$$

where $$n_{\lambda a}(t) \neq \omega_a(t) n_{\lambda b}(t) \quad (36a)$$

and $$\omega_v = \frac{\varepsilon_{5,\lambda a} c_3 x_{3,4}(t) + \varepsilon_{6,\lambda a} c_4 x_{3,4}(t)}{\varepsilon_{5,\lambda b} c_3 x_{3,4}(t) + \varepsilon_{6,\lambda b} c_4 x_{3,4}(t)} \quad (31b)$$

$$= n_{\lambda a}(t)/n_{\lambda b}(t) \quad (32b)$$

$$= \frac{\varepsilon_{5,\lambda a} c_3 + \varepsilon_{6,\lambda a} c_4}{\varepsilon_{5,\lambda b} c_3 + \varepsilon_{6,\lambda b} c_4} \quad (33b)$$

$$= \frac{\varepsilon_{5,\lambda a}(c_3/c_4) + \varepsilon_{6,\lambda a}}{\varepsilon_{5,\lambda b}(c_3/c_4) + \varepsilon_{6,\lambda b}} \quad (34b)$$

$$\approx n''_{\lambda a}(t)/n''_{\lambda b}(t) = \text{constant}_4; \quad (35b)$$

where $$s_{\lambda a}(t) \neq \omega_v(t) s_{\lambda b}(t). \quad (36b)$$

It is often the case that both equations (32) and (36) can be simultaneously satisfied to determine the proportionality constants $\omega_a$ and $\omega_v$. Additionally, the absorption coefficients at each wavelength $\varepsilon_{5,\lambda a}$, $\varepsilon_{6,\lambda a}$, $\varepsilon_{5,\lambda b}$, and $\varepsilon_{6,\lambda b}$ are constant and the central assumption of the constant saturation method is that $c_5(t)/c_6(t)$ and $c_3(t)/c_4(t)$ are constant over many sample periods. Thus, new proportionality constants $\omega_a$ and $\omega_v$ may be determined every few samples from new approximations to either the primary or secondary signal as output from the correlation canceler. Thus, the approximations to either the primary signals $s_{\lambda a}(t)$ and $s_{\lambda b}(t)$ or the secondary signals $n_{\lambda a}(t)$ and $n_{\lambda b}(t)$, found by the correlation canceler for a substantially immediately preceding set of samples of the measured signals $S_{\lambda a}(t)$ and $S_{\lambda b}(t)$ are used in a processor of the present invention for calculating the proportionality constants, $\omega_a$ and $\omega_v$, for the next set of samples of the measured signals $S_{\lambda a}(t)$ and $S_{\lambda b}(t)$.

Multiplying equation (19) by $\omega_a$ and subtracting the resulting equation from equation (18) yields a non-zero secondary reference signal:

$$n'(t)=S_{\lambda a}(t)-\omega_a S_{\lambda b}(t)=n_{\lambda a}(t)-\omega_a n_{\lambda b}(t). \quad (37a)$$

Multiplying equation (19) by $\omega_v$ and subtracting the resulting equation from equation (18) yields a non-zero primary reference signal:

$$s'(t)=S_{\lambda a}(t)-\omega_v S_{\lambda b}(t)=s_{\lambda a}(t)-\omega_v s_{\lambda b}(t). \quad (37b)$$

When using the constant saturation method, it is not necessary for the patient to remain motionless for a short period of time such that an accurate initial saturation value can be determined by known methods other than correlation canceling. With no erratic, motion-induced signal portions, a physiological monitor can very quickly produce an initial value of the saturation of $A_5$ in the volume containing $A_5$ and $A_6$. An example of a saturation calculation is given in the article "SPECTROPHOTOMETRIC DETERMINATION OF OXYGEN SATURATION OF BLOOD INDEPENDENT OF THE PRESENT OF INDOCYANINE GREEN" by G. A. Mook, et al., wherein determination of oxygen saturation in arterial blood is discussed. Another article discussing the calculation of oxygen saturation is "PULSE OXIMETRY: PHYSICAL PRINCIPLES, TECHNICAL REALIZATION AND PRESENT LIMITATIONS" by Michael R. Neuman. Then, with values for the coefficients $\omega_a$ and $\omega_v$ determined, a correlation canceler may be utilized with a secondary reference $n'(t)$ or a primary reference $s'(t)$ determined by the constant saturation method.

Figure 7A:
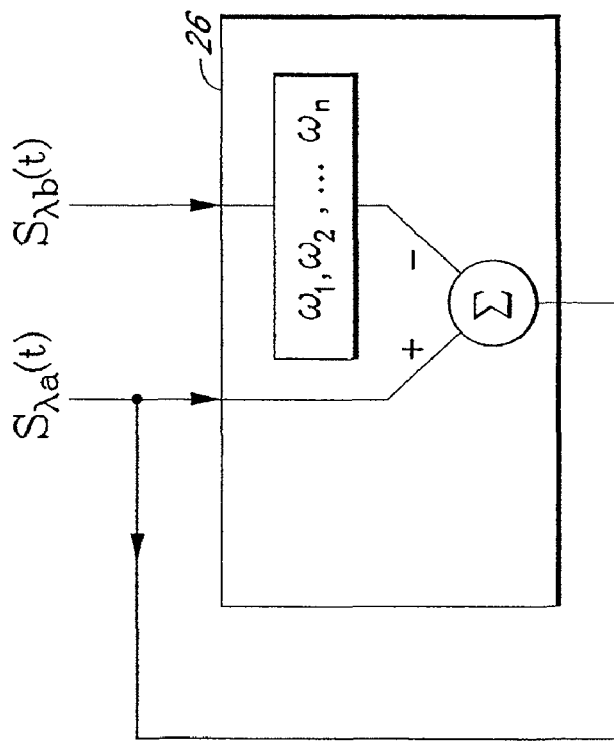
FIG. 7a illustrates a schematic diagram of a monitor, to compute primary and secondary signals, incorporating a processor of the present invention, a plurality of signal coefficients $\omega_1, \omega_2, \ldots \omega_n$, and a correlation canceler.
Figure 7A:
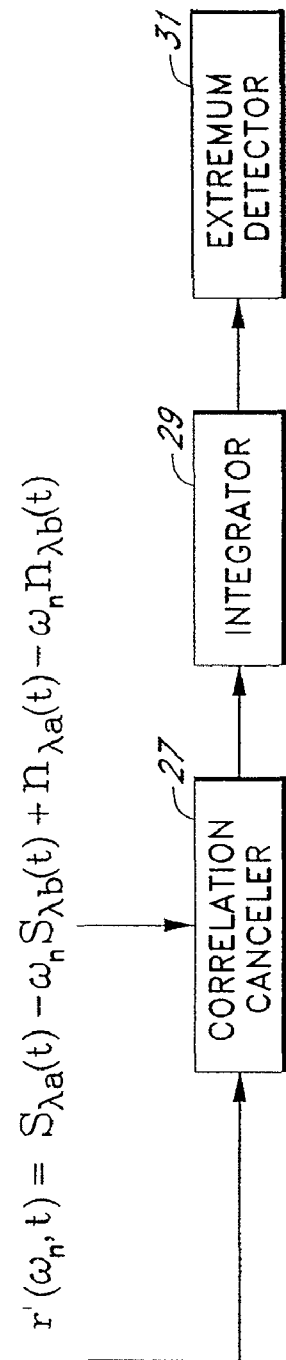

Determination of Signal Coefficients for Primary and Secondary Reference Signals Using the Constant Saturation Method The reference processor 26 of FIG. 4a and FIG. 4b of the present invention may be configured to multiply the second measured signal $S_{\lambda b}(t)=s_{\lambda b}(t)+n_{\lambda b}(t)$ by a plurality of signal coefficients $\omega_1, \omega_2, \ldots \omega_n$ and then subtract each result from the first measured signal $S_{\lambda a}(t)=s_{\lambda a}(t)+n_{\lambda a}(t)$ to obtain a plurality of reference signals $$r'(\omega,t)=s_{\lambda a}(t)-\omega s_{\lambda b}(t)+n_{\lambda a}(t)-\omega n_{\lambda b}(t) \quad (38)$$

for $\omega=\omega_1, \omega_2, \ldots \omega_n$ as shown in FIG. 7a.

In order to determine either the primary reference $s'(t)$ or the secondary reference $n'(t)$ from the above plurality of reference signals of equation (38), signal coefficients $\omega_a$ and $\omega_v$ must be determined from the plurality of signal coefficients $\omega_1, \omega_2, \ldots \omega_n$. The coefficients $\omega_a$ and $\omega_v$ are such that they cause either the primary signal portions $s_{\lambda a}(t)$ and $s_{\lambda b}(t)$ or the secondary signal portions $n_{\lambda a}(t)$ and $n_{\lambda b}(t)$ to cancel or nearly cancel when they are substituted into the reference function $r'(\omega, t)$, e.g.

$$s_{\lambda a}(t)=\omega_a s_{\lambda b}(t) \quad (39a)$$

$$n_{\lambda a}(t)=r\omega_v n_{\lambda b}(t) \quad (39b)$$

$$n'(t)=r'(\omega_a,t)=n_{\lambda a}(t)-\omega_a n_{\lambda b}(t) \quad (39c)$$

$$s'(t)=r'(\omega_v,t)=s_{\lambda a}(t)-\omega_v s_{\lambda b}(t). \quad (39d)$$

In practice, one does not usually have significant prior information about either the primary signal portions $s_{\lambda a}(t)$ and $s_{\lambda b}(t)$ or the secondary signal portions $n_{\lambda a}(t)$ and $n_{\lambda b}(t)$ of the measured signals $S_{\lambda a}(t)$ and $S_{\lambda b}(t)$. The lack of this information makes it difficult to determine which of the plurality of coefficients $\omega_1, \omega_2, \ldots \omega_n$ correspond to the signal coefficients $\omega_a = s_{\lambda a}(t)/s_{\lambda b}(t)$ and $\omega_v = n_{\lambda a}(t)/n_{\lambda b}(t)$. Herein the preferred approach to determine the signal coefficients $\omega_a$ and $\omega_v$ from the plurality of coefficients $\omega_1, \omega_2, \ldots \omega_n$ employs the use of a correlation canceler 27, such as an adaptive noise canceler, which takes a first input which corresponds to one of the measured signals $S_{\lambda a}(t)$ or $S_{\lambda b}(t)$ and takes a second input which corresponds to successively each one of the plurality of reference signals $r'(\omega_1, t), r'(\omega_2, t), \ldots, r'(\omega_n, t)$ as shown in FIG. 7a. For each of the reference signals $r'(\omega_1, t), r'(\omega_2, t), \ldots, r'(\omega_n, t)$ the corresponding output of the correlation canceler 27 is input to an integrator 29 for forming a cumulative output signal. The cumulative output signal is subsequently input to an extremum detector 31. The purpose of the extremum detector 31 is to chose signal coefficients $\omega_a$ and $\omega_v$ from the set $\omega_1, \omega_2, \ldots \omega_n$ by observing which provide a maximum in the cumulative output signal as in FIGS. 7b and 7c. In other words, coefficients which provide a maximum integrated output, such as energy or power, from the correlation canceler 27 correspond to the signal coefficients $\omega_a$ and $\omega_v$. One could also configure a system geometry which would require one to locate the coefficients from the set $\omega_1, \omega_2, \ldots \omega_n$ which provide a minimum or inflection in the cumulative output signal to identify the signal coefficients $\omega_a$ and $\omega_v$.

Use of a plurality of coefficients in the processor of the present invention in conjunction with a correlation canceler 27 to determine the signal coefficients $\omega_a$ and $\omega_v$ may be demonstrated by using the properties of correlation cancellation. If x, y and z are taken to be any collection of three time varying signals, then the properties of a generic correlation canceler C(x, y) may be defined as follows:

Property(1) $C(x,y)=0$ for $x, y$ correlated

Property(2) $C(x,y)=x$ for $x, y$ uncorrelated

Property(3) $C(x+y,z)=C(x,z)+C(y,z)$ (40)

With properties (1), (2) and (3) it is easy to demonstrate that the energy or power output of a correlation canceler with a first input which corresponds to one of the measured signals $S_{\lambda a}(t)$ or $S_{\lambda b}(t)$ and a second input which corresponds to successively each one of a plurality of reference signals $r'(\omega_1, t), r'(\omega_2, t), \ldots r'(\omega_n, t)$ can determine the signal coefficients $\omega_a$ and $\omega_v$ needed to produce the primary reference $s'(t)$ and secondary reference $n'(t)$. If we take as a first input to the correlation canceler the measured signal $S_{\lambda a}(t)$ and as a second input the plurality of reference signals $r'(\omega_1, t), r'(\omega_2, t), \ldots, r'(\omega_n, t)$ then the outputs of the correlation canceler $C(S_{\lambda a}(t), r'(\omega_j, t))$ for j=1, 2, ..., n may be written as $$C(s_{\lambda a(t)} + n_{\lambda a(t)}, s_{\lambda a(t)} - \omega_j s_{\lambda b(t)} + n_{\lambda a(t)} - r_j n_{\lambda b(t)}) \quad (41)$$

where j=1, 2, ..., n and we have used the expressions $$r'(\omega,t) = S_{\lambda a(t)} - \omega S_{\lambda b(t)} \quad (42)$$

$$S_{\lambda a(t)} = s_{\lambda a(t)} + n_{\lambda a(t)} \quad (43a)$$

$$S_{\lambda b(t)} = s_{\lambda b(t)} + n_{\lambda b(t)}. \quad (43b)$$

The use of property (3) allows one to expand equation (41) into two terms $$C(S_{\lambda a}(t), r'(\omega,t)) = C(s_{\lambda a(t)}, s_{\lambda a(t)} - \omega s_{\lambda b(t)} + n_{\lambda a(t)} - \omega n_{\lambda b} \\ {}_{(t)}) + C(n_{\lambda a(t)}, s_{\lambda a(t)} - \omega s_{\lambda b(t)} + n_{\lambda a(t)} - \omega n_{\lambda b(t)}) \quad (44)$$

so that upon use of properties (1) and (2) the correlation canceler output is given by $$C(S_{\lambda a(t)}, r'(\omega_j, t)) = s_{\lambda a(t)} \delta(\omega_{j-\omega a}) + n_{\lambda a(t)} \delta(\omega_j - \omega_v) \quad (45)$$

where $\delta(x)$ is the unit impulse function $\delta(x) = 0$ if $x \neq 0$ $\delta(x) = 1$ if $x = 0$. (46)

The time variable, t, of the correlation canceler output $C(S_{\lambda a}(t), r'(\omega_j, t))$ may be eliminated by computing its energy or power. The energy of the correlation canceler output is given by $$E_{\lambda a}(\omega_j) = \int c^2(s_{\lambda a}(t), r'(\omega_j, t)) dt \quad (47a)$$

$$= \delta(\omega - \omega_a) \int s_{\lambda a}^2(t) dt + \delta(\omega - \omega_v) \int n_{\lambda b}^2(t) dt.$$

It must be understood that one could, equally well, have chosen the measured signal $S_{\lambda b}(t)$ as the first input to the correlation canceler and the plurality of reference signals $r'(\omega_1, t), r'(\omega_2, t), \ldots, r'(\omega_n, t)$ as the second input. In this event, the correlation canceler energy output is $$E_{\lambda b}(\omega) = \int c^2(s_{\lambda b}(t), r'(\omega, t)) dt \quad (47b)$$

$$= \delta(\omega - r_a) \int s_{\lambda b}^2(t) dt + \delta(\omega_j - \omega_v) \int n_{\lambda b}^2(t) dt.$$

It must also be understood that in practical situations the use of discrete time measurement signals may be employed as well as continuous time measurement signals. In the event that discrete time measurement signals are used integration approximation methods such as the trapezoid rule, midpoint rule, Tick's rule, Simpson's approximation or other techniques may be used to compute the correlation canceler energy or power output. In the discrete time measurement signal case, the energy output of the correlation canceler may be written, using the trapezoid rule, as $$E_{\lambda a}(\omega) = \delta(\omega - \omega_a) \Delta t \left\{ \sum_{i=0}^{n} s_{\lambda a}^2(t_i) - 0.5(s_{\lambda a}^2(t_0) + s_{\lambda a}^2(t_n)) \right\} + \quad (48a)$$

$$\delta(\omega - \omega_v) \Delta t \left\{ \sum_{i=0}^{n} n_{\lambda a}^2(t_i) - 0.5(n_{\lambda a}^2(t_0) + n_{\lambda a}^2(t_n)) \right\}$$

$$E_{\lambda b}(\omega) = \delta(\omega - \omega_a) \Delta t \left\{ \sum_{i=0}^{n} s_{\lambda b}^2(t_i) - 0.5(s_{\lambda b}^2(t_0) + s_{\lambda b}^2(t_n)) \right\} + \quad (48b)$$

$$\delta(\omega - \omega_v) \Delta t \left\{ \sum_{i=0}^{n} n_{\lambda b}^2(t_i) - 0.5(n_{\lambda b}^2(t_0) + n_{\lambda b}^2(t_n)) \right\}$$

where $t_i$ is the $i^{th}$ discrete time, $t_0$ is the initial time, $t_n$ is the final time and $\Delta t$ is the time between discrete time measurement samples.

Figure 7B:
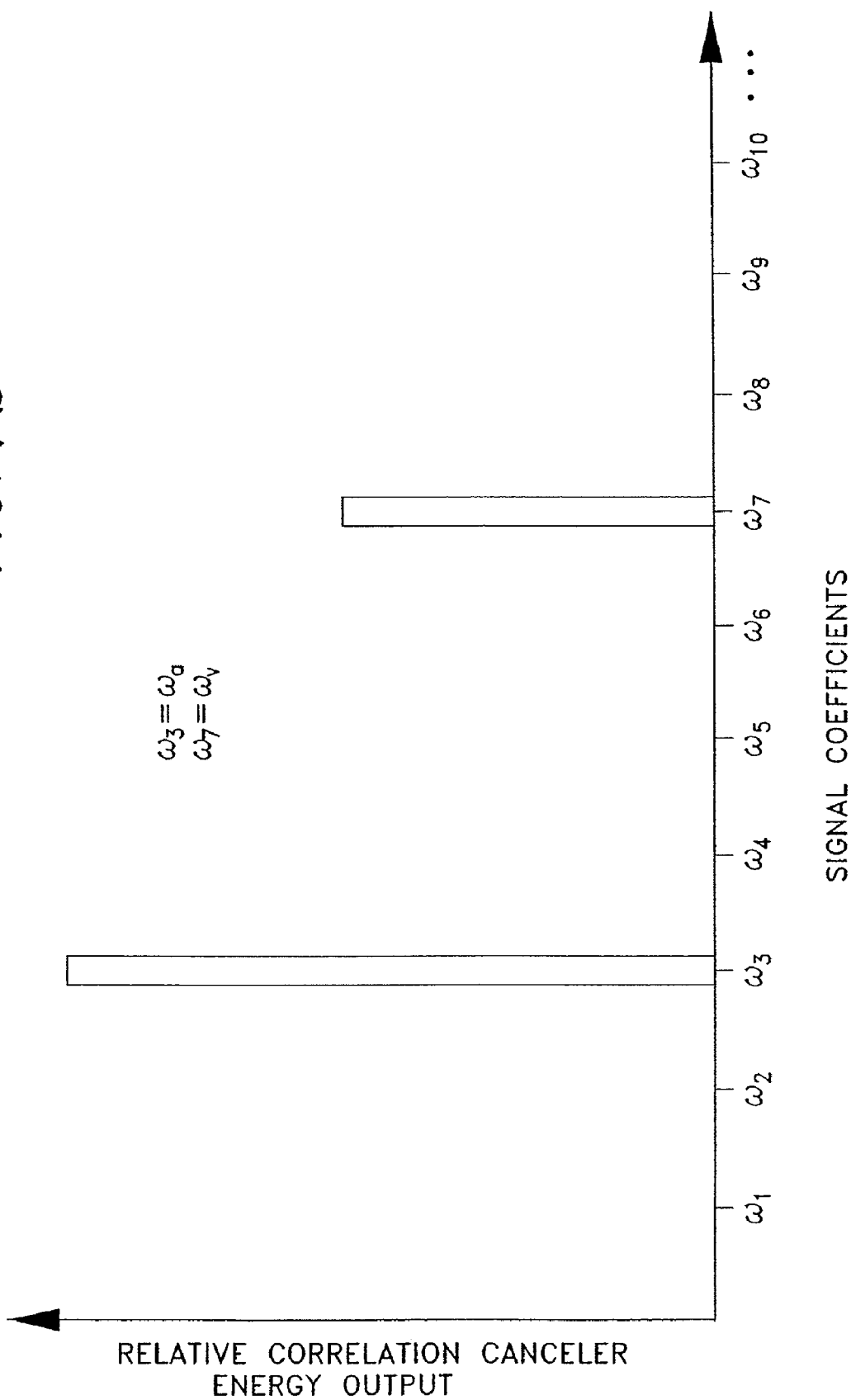
FIG. 7b illustrates the ideal correlation canceler energy or power output as a function of the signal coefficients $\omega_1, \omega_2, \ldots \omega_n$. In this particular example, $\omega_3 = \omega_a$ and $\omega_7 = \omega_v$.

The energy functions given above, and shown in FIG. 7b, indicate that the correlation canceler output is usually zero due to correlation between the measured signal $S_{\lambda a}(t)$ or $S_{\lambda b}(t)$ and many of the plurality of reference signals $r'(\omega_1, t), r'(\omega_2, t), \ldots, r'(\omega_n, t) r'(\omega, t)$. However, the energy functions are non zero at values of $\omega_j$ which correspond to cancellation of either the primary signal portions $s_{\lambda a}(t)$ and $s_{\lambda b}(t)$ or the secondary signal portions $n_{\lambda,a}(t)$ and $n_{\lambda,b}(t)$ in the reference signal $r'(\omega_j, t)$. These values correspond to the signal coefficients $\omega_a$ and $\omega_v$.

It must be understood that there may be instances in time when either the primary signal portions $s_{\lambda,a}(t)$ and $s_{\lambda,b}(t)$ or the secondary signal portions $n_{\lambda,a}(t)$ and $n_{\lambda,b}(t)$ are identically zero or nearly zero. In these cases, only one signal coefficient value will provide maximum energy or power output of the correlation canceler.

Since there may be more than one signal coefficient value which provides maximum correlation canceler energy or power output, an ambiguity may arise. It may not be immediately obvious which signal coefficient together with the reference function $r'(\omega, t)$ provides either the primary or secondary reference. In such cases, it is necessary to consider the constraints of the physical system at hand. For example, in pulse oximetry, it is known that arterial blood, whose signature is the primary plethysmographic wave, has greater oxygen saturation than venous blood, whose signature is the secondary erratic or random signal. Consequently, in pulse oximetry, the ratio of the primary signals due to arterial pulsation $\omega_a = s_{\lambda,a}(t)/s_{\lambda,b}(t)$ is the smaller of the two signal coefficient values while the ratio of the secondary signals due to mainly venous blood dynamics $\omega_v = n_{\lambda,a}(t)/n_{\lambda,b}(t)$ is the larger of the two signal coefficient values, assuming $\lambda a = 660$ nm and $\lambda b = 940$ nm.

It must be understood that in practical implementations of the plurality of reference signals and cross correlator technique, the ideal features listed as properties (1), (2) and (3) above will not be precisely satisfied but will be approximations thereof. Therefore, in practical implementations of the present invention, the correlation canceler energy curves depicted in FIG. 7b will not consist of infinitely narrow delta functions but will have finite width associated with them as depicted in FIG. 7c.

It should also be understood that it is possible to have more than two signal coefficient values which produce maximum energy or power output from a correlation canceler. This situation will arise when the measured signals each contain more than two components each of which are related by a ratio as follows:

$$s_{\lambda a}(t) = \sum_{i=1}^{n} f_{\lambda a,i}(t) s_{\lambda b}(t) = \sum_{i=1}^{n} f_{\lambda b,i}(t) \tag{49}$$

where $f_{\lambda a,i}(t) = \omega f_{\lambda b,i}(t)$ $i = 1, \ldots, n$ $\omega_i \neq \omega_j$.

The ability to employ reference signal techniques together with a correlation cancellation, such as an adaptive noise canceler, to decompose a signal into two or more signal components each of which is related by a ratio is a further aspect of the present invention.

Preferred Correlation Canceler Using a Joint Process Estimator Implementation Once either the secondary reference n'(t) or the primary reference s'(t) is determined by the processor of the present invention using either the above described ratiometric or constant saturation methods, the correlation canceler can be implemented in either hardware or software. The preferred implementation of a correlation canceler is that of an adaptive noise canceler using a joint process estimator.

The least mean squares (LMS) implementation of the internal processor 32 described above in conjunction with the adaptive noise canceler of FIG. 5a and FIG. 5b is relatively easy to implement, but lacks the speed of adaptation desirable for most physiological monitoring applications of the present invention. Thus, a faster approach for adaptive noise canceling, called a least-squares lattice joint process estimator model, is preferably used. A joint process estimator 60 is shown diagrammatically in FIG. 8 and is described in detail in Chapter 9 of Adaptive Filter Theory by Simon Haykin, published by Prentice-Hall, copyright 1986. This entire book, including Chapter 9, is hereby incorporated herein by reference. The function of the joint process estimator is to remove either the secondary signal portions $n_{\lambda,a}(t)$ or $n_{\lambda,b}(t)$ or the primary signal portions $s_{\lambda,a}(t)$ or $s_{\lambda,b}(t)$ from the measured signals $S_{\lambda,a}(t)$ or $S_{\lambda,b}(t)$, yielding either a signal $s''_{\lambda,a}(t)$ or $s''_{\lambda,b}(t)$ or a signal $n''_{\lambda,a}(t)$ or $n''_{\lambda,b}(t)$ which is a good approximation to either the primary signal $s_{\lambda,a}(t)$ or $s_{\lambda,b}(t)$ or the secondary signal $n_{\lambda,a}(t)$ or $n_{\lambda,b}(t)$. Thus, the joint process estimator estimates either the value of the primary signals $s_{\lambda,a}(t)$ or $s_{\lambda,b}(t)$ or the secondary signals $n_{\lambda,a}(t)$ or $n_{\lambda,b}(t)$. The inputs to the joint process estimator 60 are either the secondary reference n'(t) or the primary reference s'(t) and the composite measured signal $S_{\lambda,a}(t)$ or $S_{\lambda,b}(t)$. The output is a good approximation to the signal $S_{\lambda,a}(t)$ or $S_{\lambda,b}(t)$ with either the secondary signal or the primary signal removed, i.e. a good approximation to either $s_{\lambda,a}(t)$, $s_{\lambda,b}(t)$, $n_{\lambda,a}(t)$ or $n_{\lambda,b}(t)$.

Figure 8:
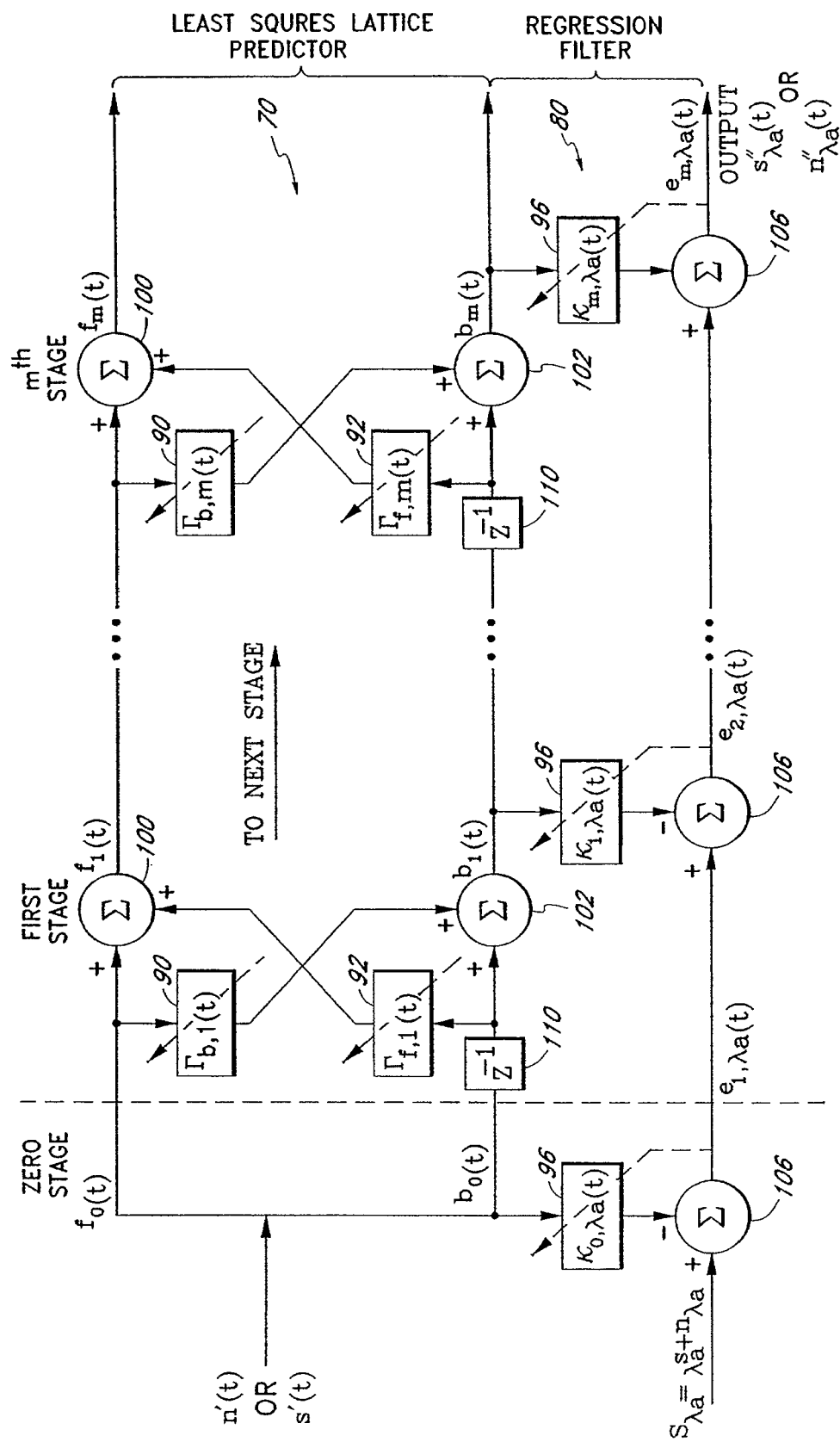
FIG. 8 is a schematic model of a joint process estimator comprising a least-squares lattice predictor and a regression filter.

The joint process estimator 60 of FIG. 8 utilizes, in conjunction, a least square lattice predictor 70 and a regression filter 80. Either the secondary reference n'(t) or the primary reference s'(t) is input to the least square lattice predictor 70 while the measured signal $S_{\lambda,a}(t)$ or $S_{\lambda,b}(t)$ is input to the regression filter 80. For simplicity in the following description, $S_{\lambda,a}(t)$ will be the measured signal from which either the primary portion $s_{\lambda,a}(t)$ or the secondary portion $n_{\lambda,a}(t)$ will be estimated by the joint process estimator 60. However, it will be noted that $S_{\lambda,b}(t)$ could equally well be input to the regression filter 80 and the primary portion $s_{\lambda,b}(t)$ or the secondary portion $n_{\lambda,b}(t)$ of this signal could equally well be estimated.

The joint process estimator 60 removes all frequencies that are present in both the reference n'(t) or s'(t), and the measured signal $S_{\lambda,a}(t)$. The secondary signal portion $n_{\lambda,a}(t)$ usually comprises frequencies unrelated to those of the primary signal portion $s_{\lambda,a}(t)$. It is highly improbable that the secondary signal portion $n_{\lambda,a}(t)$ would be of exactly the same spectral content as the primary signal portion $s_{\lambda,a}(t)$. However, in the unlikely event that the spectral content $s_{\lambda,a}(t)$ and $n_{\lambda,a}(t)$ are similar, this approach will not yield accurate results. Functionally, the joint process estimator 60 compares the reference input signal n'(t) or s'(t), which is correlated to either the secondary signal portion $n_{\lambda,a}(t)$ or the primary signal portion $s_{\lambda,a}(t)$, and input signal $S_{\lambda,a}(t)$ and removes all frequencies which are identical. Thus, the joint process estimator 60 acts as a dynamic multiple notch filter to remove those frequencies in the secondary signal component $n_{\lambda,a}(t)$ as they change erratically with the motion of the patient or those frequencies in the primary signal component $s_{\lambda,a}(t)$ as they change with the arterial pulsation of the patient. This yields a signal having substantially the same spectral content and amplitude as either the primary signal $s_{\lambda,a}(t)$ or the secondary signal $n_{\lambda,a}(t)$. Thus, the output $s''_{\lambda,a}(t)$ or $n''_{\lambda,a}(t)$ of the joint process estimator 60 is a very good approximation to either the primary signal $s_{\lambda,a}(t)$ or the secondary signal $n_{\lambda,a}(t)$. The joint process estimator 60 can be divided into stages, beginning with a zero-stage and terminating in an $m^{th}$-stage, as shown in FIG.

8. Each stage, except for the zero-stage, is identical to every other stage. The zero-stage is an input stage for the joint process estimator 60. The first stage through the $m^{th}$-stage work on the signal produced in the immediately previous stage, i.e., the $(m-1)^{th}$-stage, such that a good approximation to either the primary signal $s''_{\lambda a}(t)$ or the secondary signal $n''_{\lambda a}(t)$ is produced as output from the $m^{th}$-stage.

The least-squares lattice predictor 70 comprises registers 90 and 92, summing elements 100 and 102, and delay elements 110. The registers 90 and 92 contain multiplicative values of a forward reflection coefficient $\Gamma_{f,m}(t)$ and a backward reflection coefficient $\Gamma_{b,m}(t)$ which multiply the reference signal $n'(t)$ or $s'(t)$ and signals derived from the reference signal $n'(t)$ or $s'(t)$. Each stage of the least-squares lattice predictor outputs a forward prediction error $f_m(t)$ and a backward prediction error $b_m(t)$. The subscript m is indicative of the stage.

For each set of samples, i.e. one sample of the reference signal $n'(t)$ or $s'(t)$ derived substantially simultaneously with one sample of the measured signal $S_{\lambda a}(t)$, the sample of the reference signal $n'(t)$ or $s'(t)$ is input to the least-squares lattice predictor 70. The zero-stage forward prediction error $f_0(t)$ and the zero-stage backward prediction error $b_0(t)$ are set equal to the reference signal $n'(t)$ or $s'(t)$. The backward prediction error $b_0(t)$ is delayed by one sample period by the delay element 110 in the first stage of the least-squares lattice predictor 70. Thus, the immediately previous value of the reference $n'(t)$ or $s'(t)$ is used in calculations involving the first-stage delay element 110. The zero-stage forward prediction error is added to the negative of the delayed zero-stage backward prediction error $b_0(t-1)$ multiplied by the forward reflection coefficient value $\Gamma_{f,1}(t)$ register 90 value, to produce a first-stage forward prediction error $f_1(t)$. Additionally, the zero-stage forward prediction error $f_0(t)$ is multiplied by the backward reflection coefficient value $\Gamma_{b,1}(t)$ register 92 value and added to the delayed zero-stage backward prediction error $b_0(t-1)$ to produce a first-stage backward prediction error $b_1(t)$. In each subsequent stage, m, of the least square lattice predictor 70, the previous forward and backward prediction error values, $f_{m-1}(t)$ and $b_{m-1}(t-1)$, the backward prediction error being delayed by one sample period, are used to produce values of the forward and backward prediction errors for the present stage, $f_m(t)$ and $b_m(t)$.

The backward prediction error $b_m(t)$ is fed to the concurrent stage, m, of the regression filter 80. There it is input to a register 96, which contains a multiplicative regression coefficient value $\kappa_{m,\lambda a}(t)$. For example, in the zero-stage of the regression filter 80, the zero-stage backward prediction error $b_0(t)$ is multiplied by the zero-stage regression coefficient $\kappa_{0,\lambda a}(t)$ register 96 value and subtracted from the measured value of the signal $S_{\lambda a}(t)$ at a summing element 106 to produce a first stage estimation error signal $e_{1,\lambda a}(t)$. The first-stage estimation error signal $e_{1,\lambda a}(t)$ is a first approximation to either the primary signal or the secondary signal. This first-stage estimation error signal $e_{1,\lambda a}(t)$ is input to the first-stage of the regression filter 80. The first-stage backward prediction error $b_1(t)$, multiplied by the first-stage regression coefficient $\kappa_{1,\lambda a}(t)$ register 96 value is subtracted from the first-stage estimation error signal $e_{1,\lambda a}(t)$ to produce the second-stage estimation error $e_{2,\lambda a}(t)$. The second-stage estimation error signal $e_{2,\lambda a}(t)$ is a second, somewhat better approximation to either the primary signal $s_{\lambda a}(t)$ or the secondary signal $n_{\lambda a}(t)$.

The same processes are repeated in the least-squares lattice predictor 70 and the regression filter 80 for each stage until a good approximation $e_{m,\lambda a}(t)$, to either the primary signal $s_{\lambda a}(t)$ or the secondary signal $n_{\lambda a}(t)$ is determined. Each of the signals discussed above, including the forward prediction error $f_m(t)$, the backward prediction error $b_m(t)$, the estimation error signal $e_{m,\lambda a}(t)$, is necessary to calculate the forward reflection coefficient $\Gamma_{f,m}(t)$, the backward reflection coefficient $\Gamma_{b,m}(t)$, and the regression coefficient $\kappa_{m,\lambda a}(t)$ register 90, 92, and 96 values in each stage, m. In addition to the forward prediction error $f_m(t)$, the backward prediction error $b_m(t)$, and the estimation error $e_{m,\lambda a}(t)$ signals, a number of intermediate variables, not shown in FIG. 8 but based on the values labeled in FIG. 8, are required to calculate the forward reflection coefficient $\Gamma_{f,m}(t)$ the backward reflection coefficient $\Gamma_{b,m}(t)$, and the regression coefficient $\kappa_{m,\lambda a}(t)$ register 90, 92, and 96 values.

Intermediate variables include a weighted sum of the forward prediction error squares $\Im_m(t)$, a weighted sum of the backward prediction error squares $\beta_m(t)$, a scalar parameter $\Delta_m(t)$, a conversion factor $\gamma_m(t)$, and another scalar parameter $\rho_{m,\lambda a}(t)$. The weighted sum of the forward prediction errors $\Im_m(t)$ is defined as:

$$\Im_m(t) = \sum_{i=1}^{t} \lambda^{t-i} |f_m(i)|^2; \quad (50)$$

where $\lambda$ without a wavelength identifier, a or b, is a constant multiplicative value unrelated to wavelength and is typically less than or equal to one, i.e., $\lambda \leq 1$. The weighted sum of the backward prediction errors $\beta_m(t)$ is defined as:

$$\beta_m(t) = \sum_{i=1}^{t} \lambda^{t-i} |b_m(i)|^2 \quad (51)$$

where, again, $\lambda$ without a wavelength identifier, a or b, is a constant multiplicative value unrelated to wavelength and is typically less than or equal to one, i.e., $\lambda \leq 1$. These weighted sum intermediate error signals can be manipulated such that they are more easily solved for, as described in Chapter 9, §9.3, and defined hereinafter in equations (65) and (66).

Description of the Joint Process Estimator

The operation of the joint process estimator 60 is as follows. When the joint process estimator 60 is turned on, the initial values of intermediate variables and signals including the parameter $\Delta_{m-1}(t)$, the weighted sum of the forward prediction error signals $\Im_{m-1}(t)$, the weighted sum of the backward prediction error signals $\beta_{m-1}(t)$, the parameter $\rho_{m,\lambda a}(t)$, and the zero-stage estimation error $e_{0,\lambda a}(t)$ are initialized, some to zero and some to a small positive number $\delta$:

$$\Delta_{m-1}(0)=0; \quad (52)$$

$$\Im_{m-1}(0)=\delta; \quad (53)$$

$$\beta_{m-1}(0)=\delta; \quad (54)$$

$$\rho_{m,\lambda a}(0)=0; \quad (55)$$

$$e_{0,\lambda a}(t)=S_{\lambda a}(t) \text{ for } t \geq 0. \quad (56)$$

After initialization, a simultaneous sample of the measured signal $S_{\lambda a}(t)$ or $S_{\lambda b}(t)$ and either the secondary reference $n'(t)$ or the primary reference $s'(t)$ are input to the joint process estimator 60, as shown in FIG. 8. The forward and backward prediction error signals $f_0(t)$ and $b_0(t)$, and intermediate variables including the weighted sums of the forward and backward error signals $J_0(t)$ and $\beta_0(t)$, and the conversion factor $\gamma_0(t)$ are calculated for the zero-stage according to:

$$f_0(t)=b_0(t)=n'(t) \quad (57a)$$

$$J_0(t)=\beta_0(t)=\lambda J_0(t-1)+|n'(t)|^2 \quad (58a)$$

$$\gamma_0(t-1)=1 \quad (59a)$$

if a secondary reference n'(t) is used or according to:

$$f_0(t)=b_0(t)=s'(t) \quad (57b)$$

$$J_0(t)=\beta_0(t)=\lambda J_0(t-1)+|s'(t)|^2 \quad (58b)$$

$$\beta_0(t-1)=1 \quad (59b)$$

if a primary reference s'(t) is used where, again, $\lambda$ without a wavelength identifier, a or b, is a constant multiplicative value unrelated to wavelength.

Forward reflection coefficient $\Gamma_{f,m}(t)$, backward reflection coefficient $\Gamma_{b,m}(t)$, and regression coefficient $\kappa_{m,\lambda a}(t)$ register 90, 92 and 96 values in each stage thereafter are set according to the output of the previous stage. The forward reflection coefficient $\Gamma_{f,1}(t)$, backward reflection coefficient $\Gamma_{b,1}(t)$, and regression coefficient $\kappa_{1,\lambda a}(t)$ register 90, 92 and 96 values in the first stage are thus set according to algorithm using values in the zero-stage of the joint process estimator 60. In each stage, $m \geq 1$, intermediate values and register values including the parameter $\Delta_{m-1}(t)$; the forward reflection coefficient $\Gamma_{f,m}(t)$ register 90 value; the backward reflection coefficient $\Gamma_{b,m}(t)$ register 92 value; the forward and backward error signals $f_m(t)$ and $b_m(t)$; the weighted sum of squared forward prediction errors $J_{f,m}(t)$, as manipulated in §9.3 of the Haykin book; the weighted sum of squared backward prediction errors $\beta_b,m(t)$, as manipulated in §9.3 of the Haykin book; the conversion factor $\gamma_m(t)$; the parameter $\rho_{m,\lambda a}(t)$; the regression coefficient $\kappa_{m,\lambda a}(t)$ register 96 value; and the estimation error $e_{m+1\lambda a}(t)$ value are set according to:

$$\Delta_{m-1}(t)=\lambda\Delta_{m-1}(t-1)+\{b_{m-1}(t-1)f^*_{m-1}(t)/\gamma_{m-1}(t-1)\} \quad (60)$$

$$\Gamma_{f,m}(t)=-\{\Delta_{m-1}(t)/\beta_{m-1}(t-1)\} \quad (61)$$

$$\Gamma_{b,m}(t)=-\{\Delta^*_{m-1}(t)/J_{m-1}(t)\} \quad (62)$$

$$f_m(t)=f_{m-1}(t)+\Gamma^*_{f,m}(t)b_{m-1}(t-1) \quad (63)$$

$$b_m(t)=b_{m-1}(t-1)+\Gamma^*_{b,m}(t)f_{m-1}(t) \quad (64)$$

$$J_m(t)=J_{m-1}(t)-\{|\Delta_{m-1}(t)|^2/\beta_{m-1}(t-1)\} \quad (65)$$

$$\beta_m(t)=\beta_{m-1}(t-1)-\{|\Delta_{m-1}(t)|^2/J_{m-1}(t)\} \quad (66)$$

$$\gamma_m(t-1)=\gamma_{m-1}(t-1)-\{|b_{m-1}(t-1)|^2/\beta_{m-1}(t-1)\} \quad (67)$$

$$\rho_{m,\lambda a}(t)=\lambda\rho_{m,\lambda a}(t-1)+\{b_m(t)\epsilon^*_{m,\lambda a}(t)/\gamma_m(t)\} \quad (68)$$

$$\kappa_{m,\lambda a}(t)=\{\rho_{m,\lambda a}(t)/\beta_m(t)\} \quad (69)$$

$$\epsilon_{m+1,\lambda a}(t)=\epsilon_{m,\lambda a}(t)-\kappa^*_m(t)b_m(t) \quad (70)$$

where a(*) denotes a complex conjugate.

These equations cause the error signals $f_m(t)$, $b_m(t)$, $e_{m,\lambda a}(t)$ to be squared or to be multiplied by one another, in effect squaring the errors, and creating new intermediate error values, such as $\Delta_m-1(t)$. The error signals and the intermediate error values are recursively tied together, as shown in the above equations (60) through (70). They interact to minimize the error signals in the next stage.

After a good approximation to either the primary signal $s_{\lambda a}(t)$ or the secondary signal $n_{\lambda a}(t)$ has been determined by the joint process estimator 60, a next set of samples, including a sample of the measured signal $S_{\lambda a}(t)$ and a sample of either the secondary reference n'(t) or the primary reference s'(t), are input to the joint process estimator 60. The re-initialization process does not reoccur, such that the forward and backward reflection coefficient $\Gamma_f,m(t)$ and $\Gamma_b,m(t)$ register 90, 92 values and the regression coefficient $\kappa_{m,\lambda a}(t)$ register 96 value reflect the multiplicative values required to estimate either the primary signal portion $s_{\lambda a}(t)$ or the secondary signal portion $n_{\lambda a}(t)$ of the sample of $S_{\lambda a}(t)$ input previously. Thus, information from previous samples is used to estimate either the primary or secondary signal portion of a present set of samples in each stage.

Flowchart of Joint Process Estimator

In a signal processor, such as a physiological monitor, incorporating a reference processor of the present invention to determine a reference n'(t) or s'(t) for input to a correlation canceler, a joint process estimator 60 type adaptive noise canceler is generally implemented via a software program having an iterative loop. One iteration of the loop is analogous to a single stage of the joint process estimator as shown in FIG. 8. Thus, if a loop is iterated m times, it is equivalent to an m stage joint process estimator 60.

Figure 9:
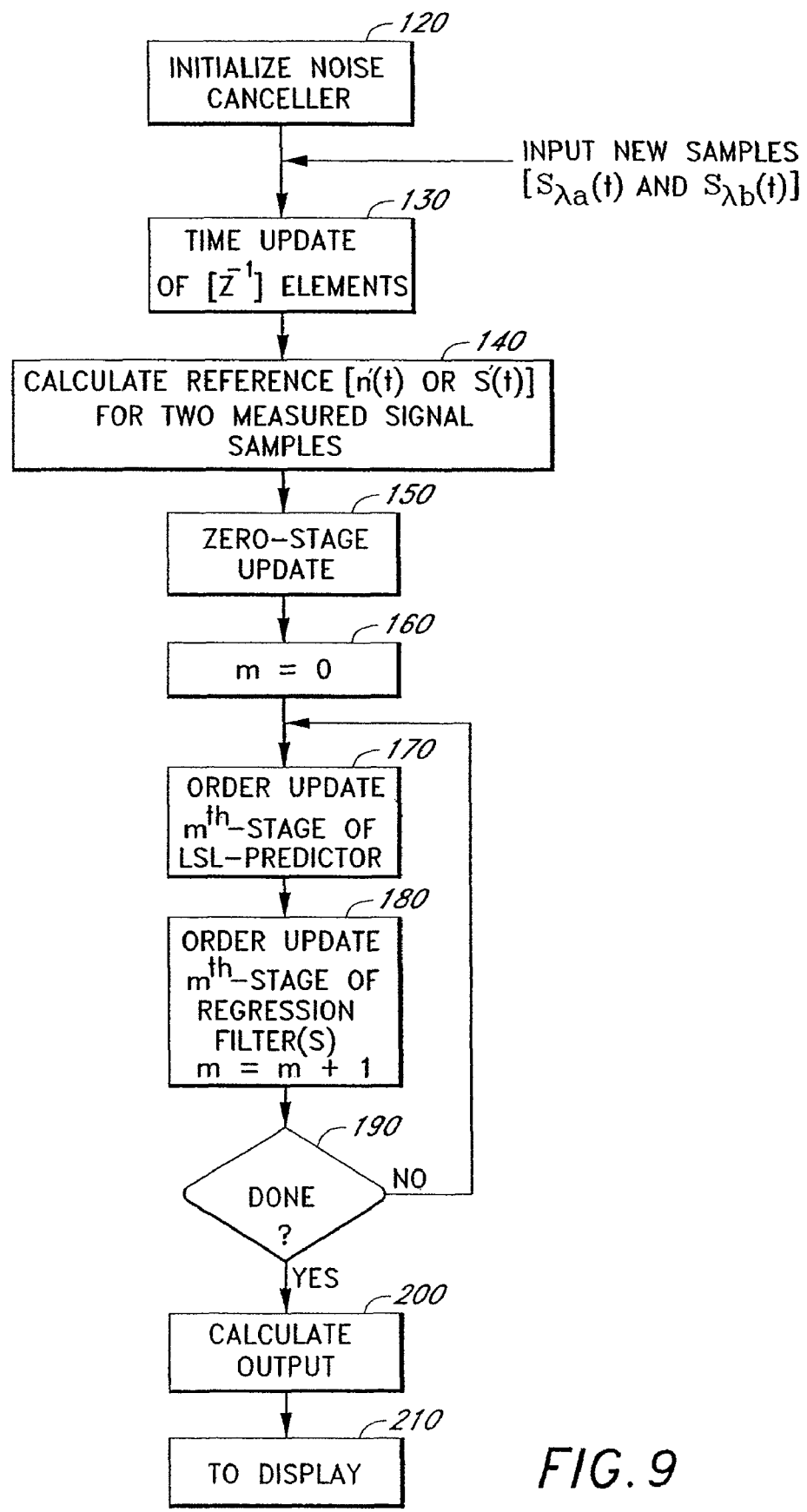
FIG. 9 is a flowchart representing a subroutine capable of implementing a joint process estimator as modeled in FIG. 8.

A flow chart of a subroutine to estimate the primary signal portion $s_{\lambda a}(t)$ or the secondary signal portion $n_{\lambda a}(t)$ of a measured signal, $S_{\lambda a}(t)$ is shown in FIG. 9. The flow chart describes how the action of a reference processor for determining either the secondary reference or the primary reference and the joint process estimator 60 would be implemented in software.

A one-time only initialization is performed when the physiological monitor is turned on, as indicated by an "INITIALIZE NOISE CANCELER" box 120. The initialization sets all registers 90, 92, and 96 and delay element variables 110 to the values described above in equations (52) through (56).

Next, a set of simultaneous samples of the measured signals $S_{\lambda a}(t)$ and $S_{\lambda b}(t)$ is input to the subroutine represented by the flowchart in FIG. 9. Then a time update of each of the delay element program variables occurs, as indicated in a "TIME UPDATE OF [$Z^{-1}$] ELEMENTS" box 130, wherein the value stored in each of the delay element variables 110 is set to the value at the input of the delay element variable 110. Thus, the zero-stage backward prediction error $b_0(t)$ is stored in the first-stage delay element variable, the first-stage backward prediction error $b_1(t)$ is stored in the second-stage delay element variable, and so on.

Then, using the set of measured signal samples $S_{\lambda a}(t)$ and $S_{\lambda b}(t)$, the reference signal is calculated according to the ratiometric or the constant saturation method described above. This is indicated by a "CALCULATE REFERENCE [n'(t) or s'(t)] FOR TWO MEASURED SIGNAL SAMPLES" box 140.

A zero-stage order update is performed next as indicated in a "ZERO-STAGE UPDATE" box 150. The zero-stage backward prediction error $b_0(t)$, and the zero-stage forward prediction error $f_0(t)$ are set equal to the value of the reference signal n'(t) or s'(t). Additionally, the weighted sum of the forward prediction errors $J_m(t)$ and the weighted sum of backward prediction errors $\beta_m(t)$ are set equal to the value defined in equations (53) and (54).

Next, a loop counter, m, is initialized as indicated in a "m=0" box 160. A maximum value of m, defining the total number of stages to be used by the subroutine corresponding to the flowchart in FIG. 9, is also defined. Typically, the loop is constructed such that it stops iterating once a criterion for convergence upon a best approximation to either the primary signal or the secondary signal has been met by the joint process estimator 60. Additionally, a maximum number of loop iterations may be chosen at which the loop stops iteration. In a preferred embodiment of a physiological monitor of the present invention, a maximum number of iterations, m=6 to m=10, is advantageously chosen.

Within the loop, the forward and backward reflection coefficient $\Gamma_{f,m}(t)$ and $\Gamma_{b,m}(t)$ register 90 and 92 values in the least-squares lattice filter are calculated first, as indicated by the "ORDER UPDATE MTH CELL OF LSL-LATTICE" box 170 in FIG. 9. This requires calculation of intermediate variable and signal values used in determining register 90, 92, and 96 values in the present stage, the next stage, and in the regression filter 80.

The calculation of regression filter register 96 value $\kappa_{m,\lambda a}(t)$ is performed next, indicated by the "ORDER UPDATE MTH STAGE OF REGRESSION FILTER(S)" box 180. The two order update boxes 170 and 180 are performed in sequence m times, until m has reached its predetermined maximum (in the preferred embodiment, m=6 to m=10) or a solution has been converged upon, as indicated by a YES path from a "DONE" decision box 190. In a computer subroutine, convergence is determined by checking if the weighted sums of the forward and backward prediction errors $J_m(t)$ and $\beta_m(t)$ are less than a small positive number. An output is calculated next, as indicated by a "CALCULATE OUTPUT" box 200. The output is a good approximation to either the primary signal or secondary signal, as determined by the reference processor 26 and joint process estimator 60 subroutine corresponding to the flow chart of FIG. 9. This is displayed (or used in a calculation in another subroutine), as indicated by a "TO DISPLAY" box 210.

A new set of samples of the two measured signals $S_{\lambda a}(t)$ and $S_{\lambda b}(t)$ is input to the processor and joint process estimator 60 adaptive noise canceler subroutine corresponding to the flowchart of FIG. 9 and the process reiterates for these samples. Note, however, that the initialization process does not re-occur. New sets of measured signal samples $S_{\lambda a}(t)$ and $S_{\lambda b}(t)$ are continuously input to the reference processor 26 and joint process estimator 60 adaptive noise canceler subroutine. The output forms a chain of samples which is representative of a continuous wave. This waveform is a good approximation to either the primary signal waveform $s_{\lambda a}(t)$ or the secondary waveform $n_{\lambda a}(t)$ at wavelength λa. The waveform may also be a good approximation to either the primary signal waveform $s_{\lambda b}(t)$ or the secondary waveform $n''_{\lambda b}(t)$ at wavelength λb.

Calculation of Saturation from Correlation Canceler Output

Physiological monitors may use the approximation of the primary signals $s''_{\lambda a}(t)$ or $s''_{\lambda b}(t)$ or the secondary signals $n''_{\lambda a}(t)$ or $n''_{\lambda b}(t)$ to calculate another quantity, such as the saturation of one constituent in a volume containing that constituent plus one or more other constituents. Generally, such calculations require information about either a primary or secondary signal at two wavelengths. For example, the constant saturation method requires a good approximation of the primary signal portions $s_{\lambda a}(t)$ and $s_{\lambda b}(t)$ of both measured signals $S_{\lambda a}(t)$ and $S_{\lambda b}(t)$ Then, the arterial saturation is determined from the approximations to both signals, i.e. $s''_{\lambda a}(t)$ and $s''_{\lambda b}(t)$. The constant saturation method also requires a good approximation of the secondary signal portions $n_{\lambda a}(t)$ or $n_{\lambda b}(t)$. Then an estimate of the venous saturation may be determined from the approximations to these signals i.e. $n''_{\lambda a}(t)$ and $n''_{\lambda b}(t)$.

In other physiological measurements, information about a signal at a third wavelength is necessary. For example, to find the saturation using the ratiometric method, signals $S_{\lambda a}(t)$ and $S_{\lambda b}(t)$ are used to find the reference signal n'(t) or s'(t). But as discussed previously, λa and λb were chosen to satisfy a proportionality relationship like that of equation (22). This proportionality relationship forces the two primary signal portions $s_{\lambda a}(t)$ and $s_{\lambda b}(t)$ of equations (23c) and (24c) to be linearly dependent. Generally, linearly dependent mathematical equations cannot be solved for the unknowns. Analogously, some desirable information cannot be derived from two linearly dependent signals. Thus, to determine the saturation using the ratiometric method, a third signal is simultaneously measured at wavelength λc. The wavelength λc is chosen such that the primary portion $s_{\lambda c}(t)$ of the measured signal $S_{\lambda c}(t)$ is not linearly dependent with the primary portions $s_{\lambda a}(t)$ and $s_{\lambda b}(t)$ of the measured signals $S_{\lambda a}(t)$ and $S_{\lambda b}(t)$. Since all measurements are taken substantially simultaneously, the secondary reference signal n'(t) is correlated to the secondary signal portions $n_{\lambda a}$, $n_{\lambda b}$, and $n_{\lambda c}$ of each of the measured signals $S_{\lambda a}(t)$, $S_{\lambda b}(t)$, and $S_{\lambda c}(t)$ and can be used to estimate approximations to the primary signal portions $s_{\lambda a}(t)$, $s_{\lambda b}(t)$, and $s_{\lambda c}(t)$ for all three measured signals $S_{\lambda a}(t)$, $S_{\lambda b}(t)$, and $S_{\lambda c}(t)$. Using the ratiometric method, estimation of the ratio of signal portions $s_{\lambda a}(t)$ and $s_{\lambda c}(t)$ of the two measured signals $S_{\lambda a}(t)$ and $S_{\lambda c}(t)$, chosen correctly, is usually satisfactory to determine most physiological data.

Figure 10:
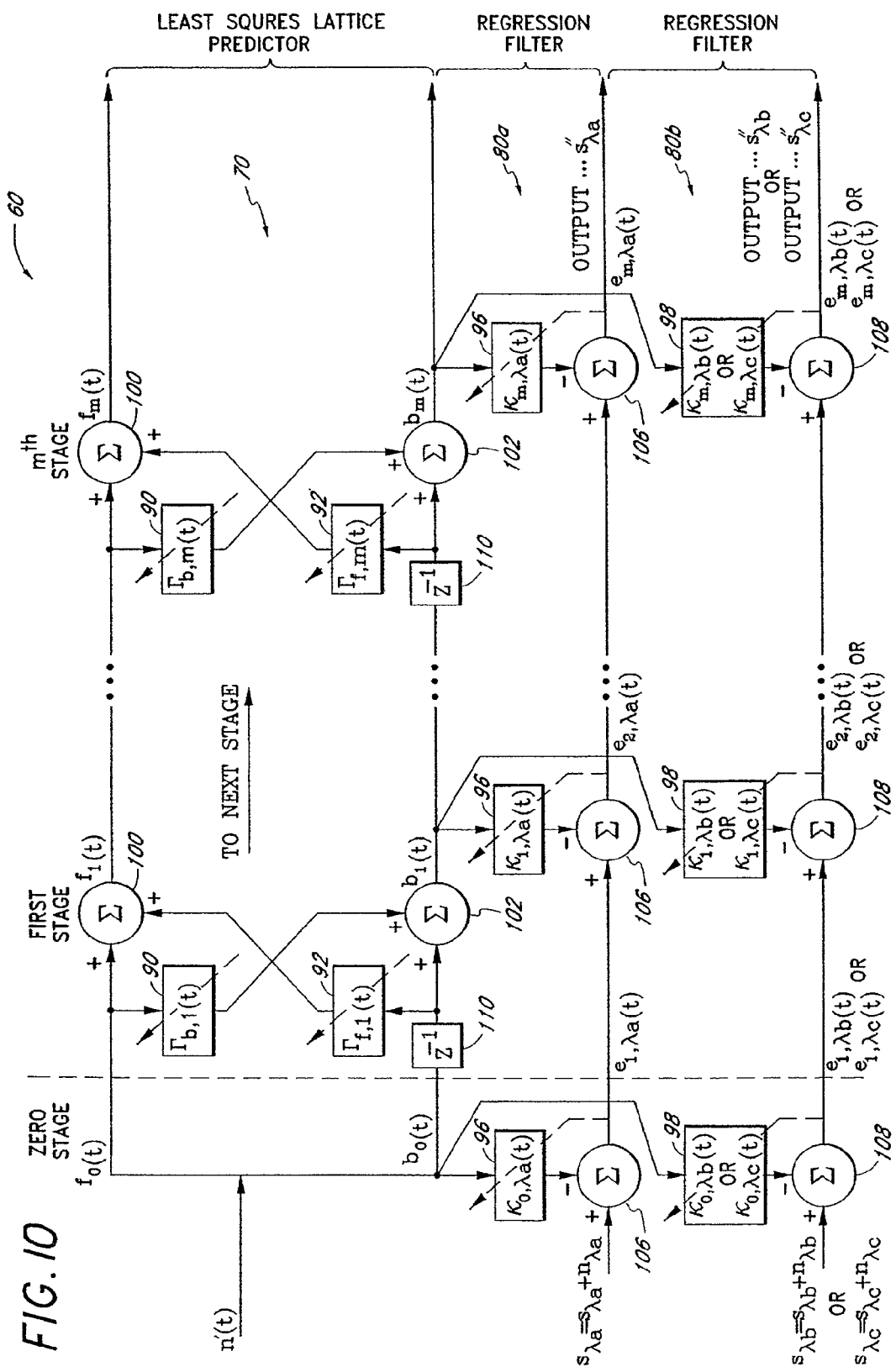
FIG. 10 is a schematic model of a joint process estimator with a least-squares lattice predictor and two regression filters.

A joint process estimator 60 having two regression filters 80a and 80b is shown in FIG. 10. A first regression filter 80a accepts a measured signal $S_{\lambda a}(t)$. A second regression filter 80b accepts a measured signal $S_{\lambda b}(t)$ or $S_{\lambda c}(t)$, depending whether the constant saturation method or the ratiometric method is used to determine the reference signal n'(t) or s'(t) for the constant saturation method or, n'(t) or s'(t) for the ratiometric method. The first and second regression filters 80a and 80b are independent. The backward prediction error $b_m(t)$ is input to each regression, filter 80a and 80b, the input for the second regression filter 80b bypassing the first regression filter 80a.

The second regression filter 80b comprises registers 98, and summing elements 108 arranged similarly to those in the first regression filter 80a. The second regression filter 80b operates via an additional intermediate variable in conjunction with those defined by equations (60) through (70), i.e.:

$$\rho_{m,\lambda b}(t)=\lambda\rho_{m,\lambda b}(t-1)+\{b_m(t)e^*_{m,\lambda b}(t)/\gamma_m(t)\}; \text{ or} \qquad (71)$$

$$\rho_{m,\lambda c}(t)=\lambda\rho_{m,\lambda c}(t-1)+\{b_m(t)e^*_{m,\lambda c}(t)/\gamma_m(t)\}; \text{ and} \qquad (72)$$

$$\rho_{0,\lambda b}(0)=0; \text{ or} \qquad (73)$$

$$\rho_{0,\lambda c}(0)=0. \qquad (74)$$

The second regression filter 80b has an error signal value defined similar to the first regression filter error signal values, $e_{m+1,\lambda a}(t)$, i.e.:

$$e_{m+1,\lambda b}(t)=e_{m,\lambda b}(t)-\kappa^*_{m,\lambda b}(t)b_m(t); \text{ or} \qquad (75)$$

$$e_{m+1,\lambda c}(t)=e_{m,\lambda c}(t)-\kappa^*_{m,\lambda b}(t)b_m(t); \text{ and} \qquad (76)$$

$$e_{0,\lambda b}(t)=S_{\lambda b}(t) \text{ for } t\geq 0; \text{ or} \qquad (77)$$

$$e_{0,\lambda c}(t)=S_{\lambda c}(t) \text{ for } t\geq 0. \qquad (78)$$

The second regression filter has a regression coefficient $\kappa_{m,\lambda b}(t)$ register 98 value defined similarly to the first regression filter error signal values, i.e.:

$$\kappa_{m,\lambda b}(t) = \{\rho_{m,\lambda b}(t)/\beta_m(t)\}; \text{ or} \tag{79}$$

$$\kappa_{m,\lambda c}(t) = \{\rho_{m,\lambda c}(t)/\beta_m(t)\}. \tag{80}$$

These values are used in conjunction with those intermediate variable values, signal values, register and register values defined in equations (52) through (70). These signals are calculated in an order defined by placing the additional signals immediately adjacent a similar signal for the wavelength λa.

For the ratiometric method, $S_{\lambda c}(t)$ is input to the second regression filter 80b. The output of the second regression filter 80b is then a good approximation to the primary signal $s''_{\lambda c}(t)$ or secondary signal $n''_{\lambda c}(t)$. For the constant saturation method, $S_{\lambda b}(t)$ is input to the second regression filter 80b. The output is then a good approximation to the primary signal $s''_{\lambda b}(t)$ or secondary signal $s''_{\lambda b}(t)$.

The addition of the second regression filter 80b does not substantially change the computer program subroutine represented by the flowchart of FIG. 9. Instead of an order update of the $m^{th}$ in stage of only one regression filter, an order update of the $m^{th}$ stage of both regression filters 80a and 80b is performed. This is characterized by the plural designation in the "ORDER UPDATE OF min STAGE OF REGRESSION FILTER(S)" box 180 in FIG. 9. Since the regression filters 80a and 80b operate independently, independent calculations can be performed in the reference processor and joint process estimator 60 adaptive noise canceler subroutine modeled by the flowchart of FIG. 9.

Calculation of Saturation

Once good approximations to the primary signal portions, $s''_{\lambda a}(t)$ and $s''_{\lambda c}(t)$ or the secondary signal portions $n''_{\lambda a}(t)$ and $n''_{\lambda c}(t)$ for the ratiometric method and $s''_{\lambda a}(t)$ and $s''_{\lambda b}(t)$ or $n''_{\lambda a}(t)$ and $n''_{\lambda c}(t)$ for the constant saturation method, have been determined by the joint process estimator 60, the saturation of $A_5$ in a volume containing $A_5$ and $A_6$, for example, may be calculated according to various known methods. Mathematically, the approximations to the primary signals can be written:

$$s''_{\lambda a}(t) \approx \epsilon_{5,\lambda a} c_5 x_{5,6}(t) + \epsilon_{6,\lambda a} c_6 x_{5,6}(t) + \epsilon_{5,\lambda a} c_3 x_{3,4}(t) + \epsilon_{6,\lambda a} c_3 x_{3,4}(t) \tag{81a}$$

$$s''_{\lambda c}(t) \approx \epsilon_{5,\lambda c} c_5 x_{5,6}(t) + \epsilon_{6,\lambda c} c_6 x_{5,6}(t) + \epsilon_{5,\lambda c} c_3 x_{3,4}(t) + \epsilon_{6,\lambda c} c_3 x_{3,4}(t) \tag{82a}$$

for the ratiometric method using wavelengths λa and λc, and assuming that the secondary reference $n'(t)$ is uncorrelated with $x_{3,4}(t)$ and $x_{5,6}(t)$. Terms involving $x_{3,4}(t)$ and $x_{5,6}(t)$ may then be separated using the constant saturation method. It is important to understand that if $n'(t)$ is uncorrelated with $x_{3,4}(t)$ and $x_{5,6}(t)$, use of the ratiometric method followed by use of the constant saturation method results in a more accurate computation of the saturation of $A_3$ in the layer $x_{3,4}$ then by use of the ratiometric or constant saturation methods alone. In the event that $n'(t)$ and $x_{3,4}(t)$ are correlated the ratiometric method yields $$s''_{\lambda a}(t) \approx \epsilon_{5,\lambda c} c_5 x_{5,6}(t) + \epsilon_{6,\lambda a} c_6 x_{5,6}(t); \text{ and} \tag{81b}$$

$$s''_{\lambda c}(t) \approx \epsilon_{5,\lambda c} c_5 x_{5,6}(t) + \epsilon_{6,\lambda c} c_6 x_{5,6}(t). \tag{82b}$$

For the constant saturation method, the approximations to the primary signals can be written, in terms of λa and λb, as:

$$s''_{\lambda a}(t) \approx \epsilon_{5,\lambda a} c_5 x_{5,6}(t) + \epsilon_{6,\lambda c} c_6 x_{5,6}(t); \text{ and} \tag{83}$$

$$s''_{\lambda b}(t) \approx \epsilon_{5,\lambda b} c_5 x_{5,6}(t) + \epsilon_{6,\lambda b} c_6 x_{5,6}(t). \tag{84}$$

Equations (81b), (82b), (83) and (84) are equivalent to two equations having three unknowns, namely $c_5(t)$, $c_6(t)$ and $x_5,6(t)$. In both the ratiometric and the constant saturation cases, the saturation can be determined by acquiring approximations to the primary or secondary signal portions at two different, yet proximate times $t_1$ and $t_2$ over which the saturation of $A_5$ in the volume containing $A_5$ and $A_6$ and the saturation of $A_3$ in the volume containing $A_3$ and $A_4$ does not change substantially. For example, for the primary signals estimated by the ratiometric method, at times $t_1$ and $t_2$:

$$s''_{\lambda a}(t_1) \approx \epsilon_{5,\lambda a} c_5 x_{5,6}(t_1) + \epsilon_{6,\lambda a} c_6 x_{5,6}(t_1) \tag{85}$$

$$s''_{\lambda c}(t_1) \approx \epsilon_{5,\lambda c} c_5 x_{5,6}(t_1) + \epsilon_{6,\lambda c} c_6 x_{5,6}(t_1) \tag{86}$$

$$s''_{\lambda a}(t_2) \approx \epsilon_{5,\lambda a} c_5 x_{5,6}(t_2) + \epsilon_{6,\lambda a} c_6 x_{5,6}(t_2) \tag{87}$$

$$s''_{\lambda c}(t_2) \approx \epsilon_{5,\lambda c} c_5 x_{5,6}(t_2) + \epsilon_{6,\lambda c} c_6 x_{5,6}(t_2) \tag{88}$$

Then, difference signals may be determined which relate the signals of equations (85) through (88), i.e.:

$$\Delta s_{\lambda a} = s''_{\lambda a}(t_1) - s''_{\lambda a}(t_2) \approx \epsilon_{5,\lambda a} c_5 \Delta x + \epsilon_{6,\lambda a} c_6 \Delta x; \text{ and} \tag{89}$$

$$\Delta s_{\lambda c} = s''_{\lambda c}(t_1) - s''_{\lambda c}(t_2) \approx \epsilon_{5,\lambda c} c_5 \Delta x + \epsilon_{\lambda c} c_6 \Delta x. \tag{90}$$

where $\Delta x = x_{5,6}(t_1) - x_{5,6}(t_2)$. The average saturation at time $t = (t_1+t_2)/2$ is:

$$\text{Saturation}(t) = c_5(t)/[c_5(t) + c_6(t)] \tag{91}$$

$$= \frac{\epsilon_{6,\lambda a} - \epsilon_{6,\lambda c}(\Delta s_{\lambda a}/\Delta s_{\lambda c})}{\epsilon_{6,\lambda a} - \epsilon_{5,\lambda a} - (\epsilon_{6,\lambda a} - \epsilon_{5,\lambda a})(\Delta s_{\lambda a}/\Delta s_{\lambda c})} \tag{92}$$

It will be understood that the $\Delta x$ term drops out from the saturation calculation because of the division. Thus, knowledge of the thickness of the primary constituents is not required to calculate saturation.

Pulse Oximetry Measurements

A specific example of a physiological monitor utilizing a processor of the present invention to determine a secondary reference $n'(t)$ for input to a correlation canceler that removes erratic motion-induced secondary signal portions is a pulse oximeter. Pulse oximetry may also be performed utilizing a processor of the present invention to determine a primary signal reference $s'(t)$ which may be used for display purposes or for input to a correlation canceler to derive information about patient movement and venous blood oxygen saturation.

A pulse oximeter typically causes energy to propagate through a medium where blood flows close to the surface for example, an ear lobe, or a digit such as a finger, or a forehead. An attenuated signal is measured after propagation through or reflected from the medium. The pulse oximeter estimates the saturation of oxygenated blood.

Freshly oxygenated blood is pumped at high pressure from the heart into the arteries for use by the body. The volume of blood in the arteries varies with the heartbeat, giving rise to a variation in absorption of energy at the rate of the heartbeat, or the pulse.

Oxygen depleted, or deoxygenated, blood is returned to the heart by the veins along with unused oxygenated blood. The volume of blood in the veins varies with the rate of breathing, which is typically much slower than the heartbeat. Thus, when there is no motion induced variation in the thickness of the veins, venous blood causes a low frequency variation in absorption of energy. When there is motion induced variation in the thickness of the veins, the low frequency variation in absorption is coupled with the erratic variation in absorption due to motion artifact.

In absorption measurements using the transmission of energy through a medium, two light emitting diodes (LED's) are positioned on one side of a portion of the body where blood flows close to the surface, such as a finger, and a photodetector is positioned on the opposite side of the finger. Typically, in pulse oximetry measurements, one LED emits a visible wavelength, preferably red, and the other LED emits an infrared wavelength. However, one skilled in the art will realize that other wavelength combinations could be used.

The finger comprises skin, tissue, muscle, both arterial blood and venous blood, fat, etc., each of which absorbs light energy differently due to different absorption coefficients, different concentrations, and different thicknesses. When the patient is not moving, absorption is substantially constant except for the flow of blood. The constant attenuation can be determined and subtracted from the signal via traditional filtering techniques. When the patient moves, the absorption becomes erratic. Erratic motion induced noise typically cannot be predetermined and/or subtracted from the measured signal via traditional filtering techniques. Thus, determining the oxygen saturation of arterial blood and venous blood becomes more difficult.

Figure 11:
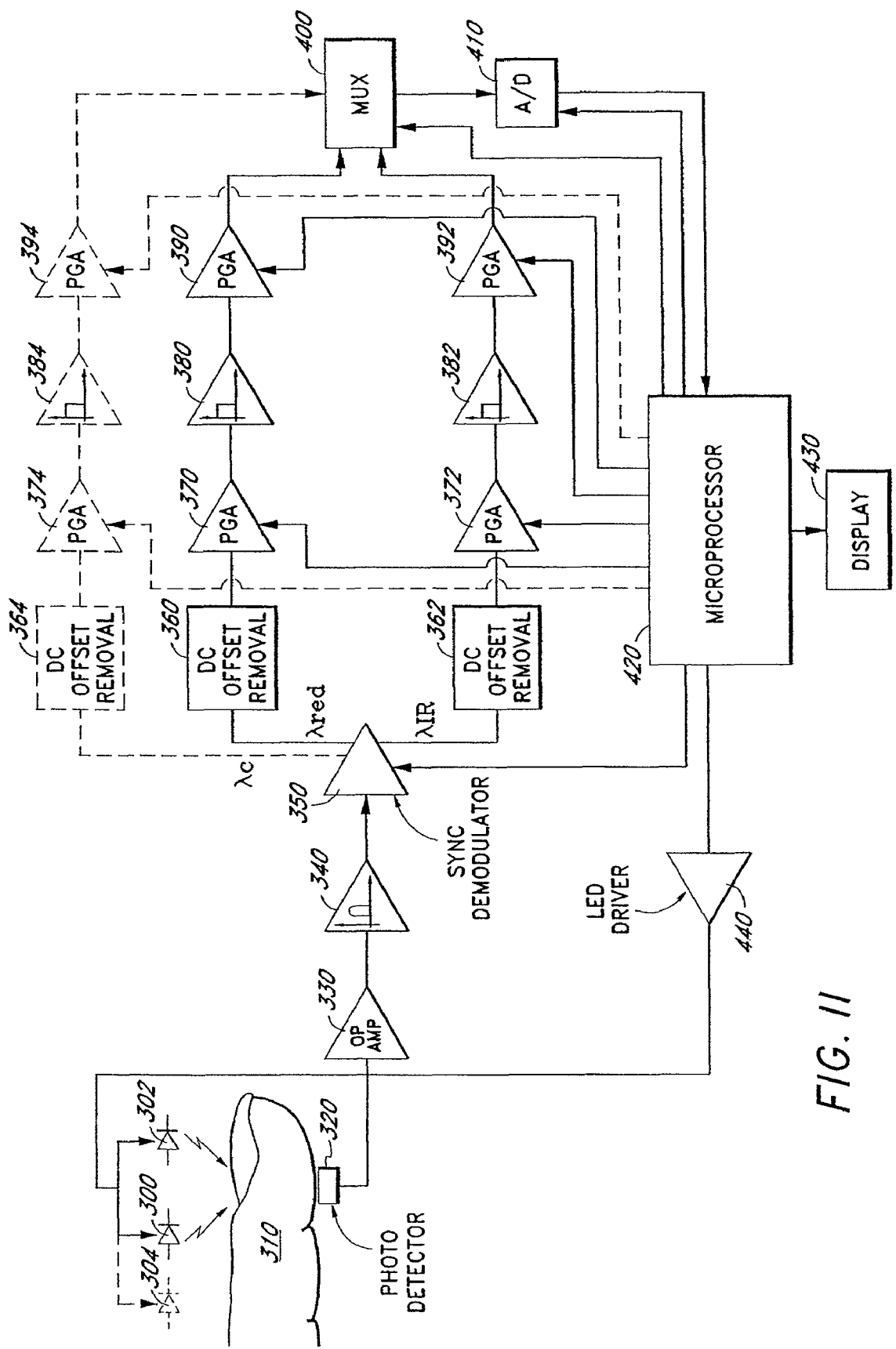
FIG. 11 is an example of a physiological monitor incorporating a processor of the present invention and a correlation canceler within a microprocessor. This physiological monitor is specifically designed to measure a plethysmographic waveform or a motion artifact waveform and perform oximetry measurements.

A schematic of a physiological monitor for pulse oximetry is shown in FIG. 11. Two LED's 300 and 302, one LED 300 emitting red wavelengths and another LED 302 emitting infrared wavelengths, are placed adjacent a finger 310. A photodetector 320, which produces an electrical signal corresponding to the attenuated visible and infrared light energy signals is located opposite the LED's 300 and 302. The photodetector 320 is connected to a single channel of common processing circuitry including an amplifier 330 which is in turn connected to a band pass filter 340. The band pass filter 340 passes it output signal into a synchronized demodulator 350 which has a plurality of output channels. One output channel is for signals corresponding to visible wavelengths and another output channel is for signals corresponding to infrared wavelengths.

The output channels of the synchronized demodulator for signals corresponding to both the visible and infrared wavelengths are each connected to separate paths, each path comprising further processing circuitry. Each path includes a DC offset removal element 360 and 362, such as a differential amplifier, a programmable gain amplifier 370 and 372 and a low pass filter 380 and 382. The output of each low pass filter 380 and 382 is amplified in a second programmable gain amplifier 390 and 392 and then input to a multiplexer 400.

The multiplexer 400 is connected to an analog-to-digital converter 410 which is in turn connected to a microprocessor 420. Control lines between the microprocessor 420 and the multiplexer 400, the microprocessor 420 and the analog-to-digital converter 410, and the microprocessor 420 and each programmable gain amplifier 370, 372, 390, and 392 are formed. The microprocessor 420 has additional control lines, one of which leads to a display 430 and the other of which leads to an LED driver 440 situated in a feedback loop with the two LED's 300 and 302.

The LED's 300 and 302 each emits energy which is absorbed by the finger 310 and received by the photodetector 320. The photodetector 320 produces an electrical signal which corresponds to the intensity of the light energy striking the photodetector 320 surface. The amplifier 330 amplifies this electrical signal for ease of processing. The band pass filter 340 then removes unwanted high and low frequencies. The synchronized demodulator 350 separates the electrical signal into electrical signals corresponding to the red and infrared light energy components. A predetermined reference voltage, $V_{ref}$, is subtracted by the DC offset removal element 360 and 362 from each of the separate signals to remove substantially constant absorption which corresponds to absorption when there is no motion induced signal component. Then the first programmable gain amplifiers 370 and 372 amplify each signal for ease of manipulation. The low pass filters 380 and 382 integrate each signal to remove unwanted high frequency components and the second programmable gain amplifiers 390 and 392 amplify each signal for further ease of processing.

The multiplexer 400 acts as an analog switch between the electrical signals corresponding to the red and the infrared light energy, allowing first a signal corresponding to the red light to enter the analog-to-digital converter 410 and then a signal corresponding to the infrared light to enter the analog-to-digital converter 410. This eliminates the need for multiple analog-to-digital converters 410. The analog-to-digital converter 410 inputs the data into the microprocessor 420 for calculation of either a primary or secondary reference signal via the processing technique of the present invention and removal or derivation of motion induced signal portions via a correlation canceler, such as an adaptive noise canceler. The microprocessor 420 centrally controls the multiplexer 400, the analog-to-digital converter 410, and the first and second programmable gain amplifiers 370 and 390 for both the red and the infrared channels. Additionally, the microprocessor 420 controls the intensity of the LED's 302 and 304 through the LED driver 440 in a servo loop to keep the average intensity received at the photodetector 320 within an appropriate range. Within the microprocessor 420 a reference signal n'(t) or s'(t) is calculated via either the constant saturation method or the ratiometric method, as described above, the constant saturation method being generally preferred. This signal is used in an adaptive noise canceler of the joint process estimator type 60, as described above.

The multiplexer 400 time multiplexes, or sequentially switches between, the electrical signals corresponding to the red and the infrared light energy. This allows a single channel to be used to detect and begin processing the electrical signals. For example, the red LED 300 is energized first and the attenuated signal is measured at the photodetector 320. An electrical signal corresponding to the intensity of the attenuated red light energy is passed to the common processing circuitry. The infrared LED 302 is energized next and the attenuated signal is measured at the photodetector 320. An electrical signal corresponding to the intensity of the attenuated infrared light energy is passed to the common processing circuitry. Then, the red LED 300 is energized again and the corresponding electrical signal is passed to the common processing circuitry. The sequential energization of LED's 300 and 302 occurs continuously while the pulse oximeter is operating.

The processing circuitry is divided into distinct paths after the synchronized demodulator 350 to ease time constraints generated by time multiplexing. In the preferred embodiment of the pulse oximeter shown in FIG. 11, a sample rate, or LED energization rate, of 625 Hz is advantageously employed. Thus, electrical signals reach the synchronized demodulator 350 at a rate of 625 Hz. Time multiplexing is not used in place of the separate paths due to settling time constraints of the low pass filters 380, 382, and 384.

In FIG. 11, a third LED 304 is shown adjacent the finger, located near the LED's 300 and 302. The third LED 304 is used to measure a third signal $S_{\lambda c}(t)$ to be used to determine saturation using the ratiometric method. The third LED 304 is time multiplexed with the red and infrared LED's 300 and 302. Thus, a third signal is input to the common processing circuitry in sequence with the signals from the red and infrared LED's 300 and 302. After passing through and being processed by the operational amplifier 330, the band pass filter 340, and the synchronized demodulator 350, the third electrical signal corresponding to light energy at wavelength $\lambda c$ is input to a separate path including a DC offset removal element 364, a first programmable gain amplifier 374, a low pass filter 384, and a second programmable gain amplifier 394. The third signal is then input to the multiplexer 400.

The dashed line connection for the third LED 304 indicates that this third LED 304 is incorporated into the pulse oximeter when the ratiometric method is used; it is unnecessary for the constant saturation method. When the third LED 304 is used, the multiplexer 400 acts as an analog switch between all three LED 300, 302, and 304 signals. If the third LED 304 is utilized, feedback loops between the microprocessor 420 and the first and second programmable gain amplifier 374 and 394 in the $\lambda c$ wavelength path are also formed.

For pulse oximetry measurements using the ratiometric method, the signals (logarithm converted) transmitted through the finger 310 at each wavelength $\lambda a$, $\lambda b$, and $\lambda c$ are:

$$S_{\lambda a}(t) = S_{\lambda red1}(t) \qquad (93)$$
$$= \varepsilon_{HbO2,\lambda a} c_{HbO2}^A x^A(t) + \varepsilon_{Hb,\lambda a} c_{Hb}^A x^A(t) +$$
$$\varepsilon_{HbO2,\lambda a} c_{HbO2}^V x^V(t) + \varepsilon_{Hb,\lambda a} c_{Hb}^V x^V(t) + n_{\lambda a}(t);$$

$$S_{\lambda b}(t) = S_{\lambda red2}(t) \qquad (94)$$
$$= \varepsilon_{HbO2,\lambda b} c_{HbO2}^A x^A(t) + \varepsilon_{Hb,\lambda b} c_{Hb}^A x^A(t) +$$
$$\varepsilon_{HbO2,\lambda b} c_{HbO2}^V x^V(t) + \varepsilon_{Hb,\lambda b} c_{Hb}^V x^V(t) + n_{\lambda b}(t);$$

$$S_{\lambda c}(t) = S_{\lambda IR}(t) \qquad (95)$$
$$= \varepsilon_{HbO2,\lambda c} c_{HbO2}^A x^A(t) + \varepsilon_{Hb,\lambda c} c_{Hb}^A x^A(t) +$$
$$\varepsilon_{HbO2,\lambda c} c_{HbO2}^V x^V(t) + \varepsilon_{Hb,\lambda c} c_{Hb}^V x^V(t) + n_{\lambda c}(t).$$

In equations (93) through (95), $x^A(t)$ is the lump-sum thickness of the arterial blood in the finger; $x^V(t)$ is the lump-sum thickness of venous blood in the finger; $\varepsilon_{HbO2,\lambda a}$, $\varepsilon_{HbO2,\lambda b}$, $\varepsilon_{HbO2,\lambda c}$, $\varepsilon_{Hb,\lambda a}$, $\varepsilon_{Hb,\lambda b}$, and $\varepsilon_{Hb,\lambda c}$ are the absorption coefficients of the oxygenated and non-oxygenated hemoglobin, at each wavelength measured; and $c_{HbO2}(t)$ and $c_{Hb}(t)$ with the superscript designations A and V are the concentrations of the oxygenated and non-oxygenated arterial blood and venous blood, respectively.

For the ratiometric method, the wavelengths chosen are typically two in the visible red range, i.e. $\lambda a$ and $\lambda b$, and one in the infrared range, i.e., $\lambda c$. As described above, the measurement wavelengths $\lambda a$ and $\lambda b$ are advantageously chosen to satisfy a proportionality relationship which removes the primary signal portions $s_{\lambda a}(t)$ and $s_{\lambda b}(t)$, yielding a secondary reference n'(t). In the preferred embodiment, the ratiometric method is used to determine the secondary reference signal n'(t) by picking two wavelengths that cause the primary portions $s_{\lambda a}(t)$ and $s_{\lambda b}(t)$ of the measured signals $S_{\lambda a}(t)$ and $S_{\lambda b}(t)$ to become linearly dependent similarly to equation (22); i.e. wavelengths $\lambda a$ and $\lambda b$ which satisfy:

$$\varepsilon_{HbO2,\lambda a}/\varepsilon_{Hb,\lambda a} = \varepsilon_{HbO2,\lambda b}/\varepsilon_{Hb,\lambda b} \qquad (96)$$

Typical wavelength values chosen are $\lambda a$=650 nm and $\lambda b$=685 nm. Additionally a typical wavelength value for $\lambda c$ is $\lambda c$=940 nm. By picking wavelengths $\lambda a$ and $\lambda b$ to satisfy equation (96) the venous portion of the measured signal is also caused to become linearly dependent even though it is not usually considered to be part of the primary signals as is the case in the constant saturation method. Thus, the venous portion of the signal is removed with the primary portion of the constant saturation method. The proportionality relationship between equations (93) and (94) which allows determination of a non-zero secondary reference signal n'(t), similarly to equation (25) is:

$$\omega_{av} = \varepsilon_{Hb,\lambda a}/\varepsilon_{Hb,\lambda b}; \text{ where} \qquad (97)$$

$$n_{\lambda a(t)} = \omega_{av} n_{\lambda a(t)}. \qquad (98)$$

In pulse oximetry, both equations (97) and (98) can typically be satisfied simultaneously.

Figure 12:
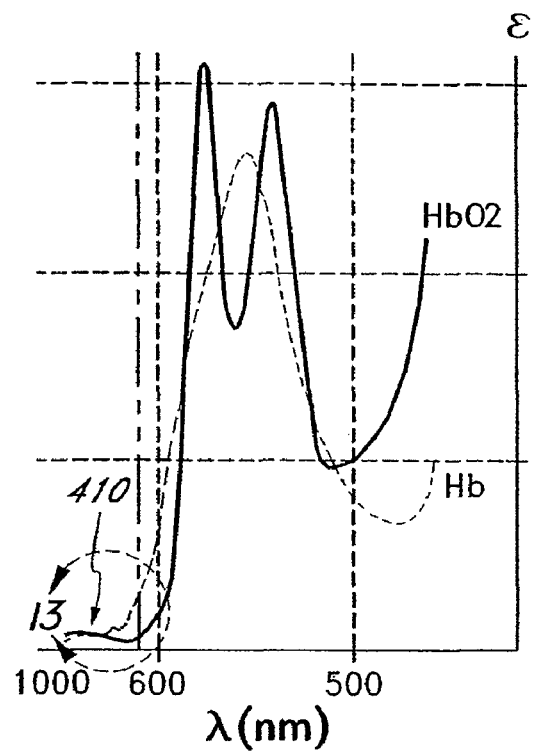
FIG. 12 is a graph of oxygenated and deoxygenated hemoglobin absorption coefficients vs. wavelength.
Figure 14:
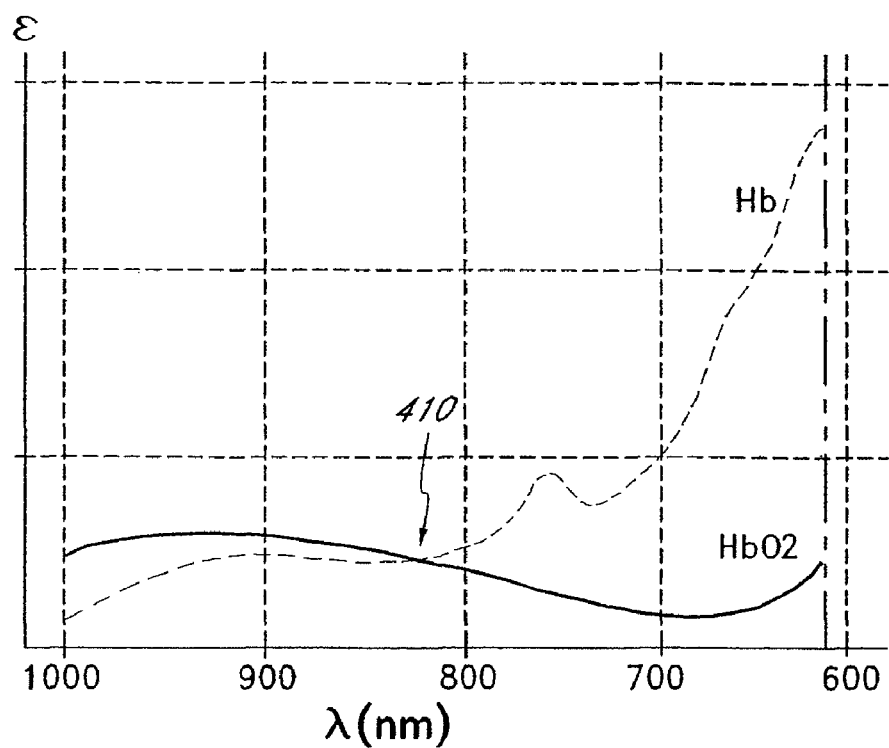
FIG. 14 is an expanded view of a portion of FIG. 12 marked by a circle labeled 13.
Figure 13:
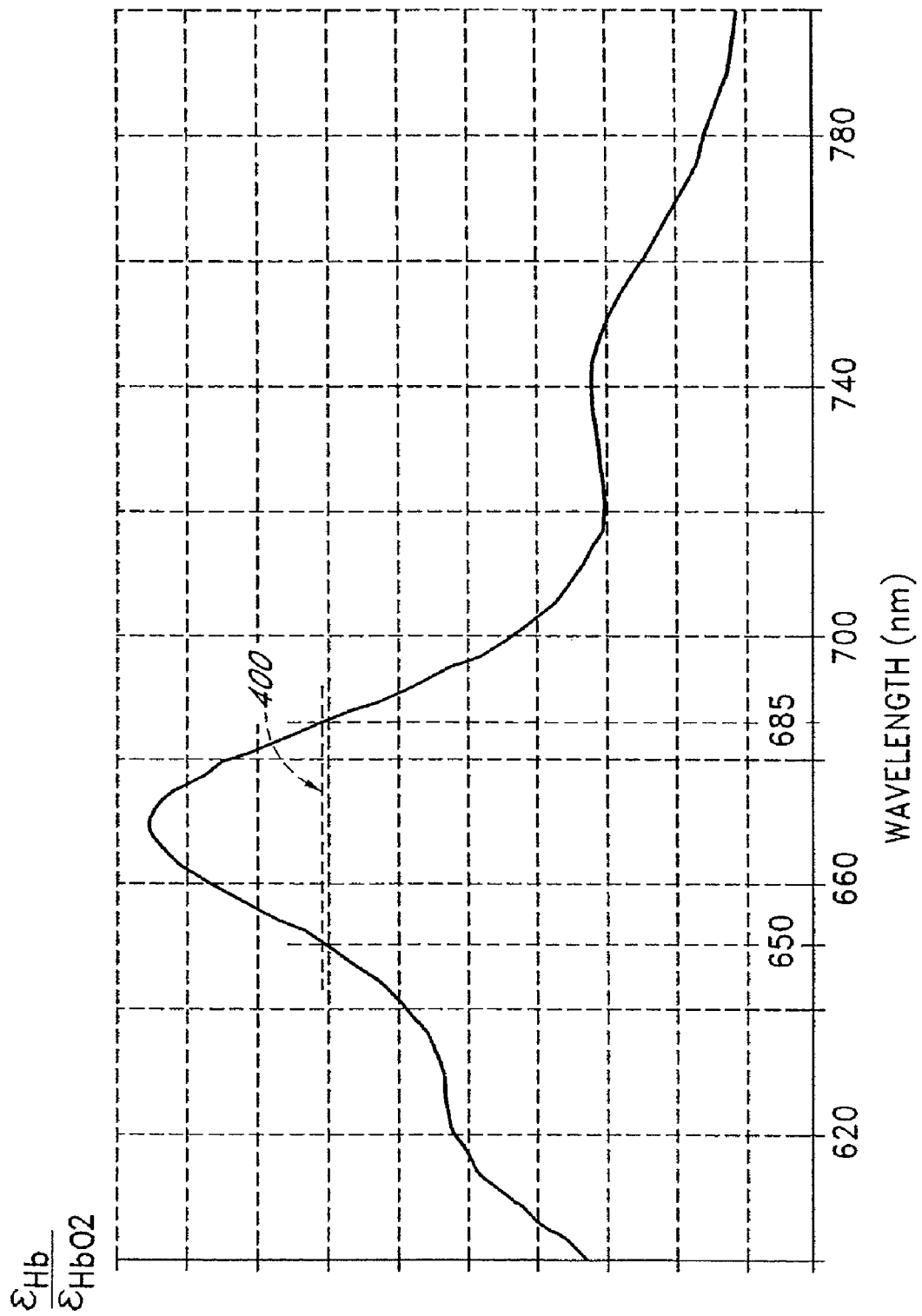
FIG. 13 is a graph of the ratio of the absorption coefficients of deoxygenated hemoglobin divided by oxygenated hemoglobin vs. wavelength.

FIG. 12 is a graph of the absorption coefficients of oxygenated and deoxygenated hemoglobin ($\varepsilon_{HbO2}$ and $\varepsilon_{Hb}$) vs. wavelength ($\lambda$). FIG. 13 is a graph of the ratio of the absorption coefficients vs. wavelength, i.e., $\varepsilon_{Hb}/\varepsilon_{HbO2}$ vs. $\lambda$ over the range of wavelength within circle 13 in FIG. 12. Anywhere a horizontal line touches the curve of FIG. 13 twice, as does line 400, the condition of equation (96) is satisfied. FIG. 14 shows an exploded view of the area of FIG. 12 within the circle 13. Values of $\varepsilon_{HbO2}$ and $\varepsilon_{Hb}$ at the wavelengths where a horizontal line touches the curve of FIG. 13 twice can then be determined from the data in FIG. 14 to solve for the proportionality relationship of equation (97).

A special case of the ratiometric method is when the absorption coefficients $\varepsilon_{HbO2}$ and $\varepsilon_{Hb}$ are equal at a wavelength. Arrow 410 in FIG. 12 indicates one such location, called an isobestic point. FIG. 14 shows an exploded view of the isobestic point. To use isobestic points with the ratiometric method, two wavelengths at isobestic points are determined to satisfy equation (96)

Multiplying equation (94) by $\omega_a v$ and then subtracting equation (94) from equation (93), a non-zero secondary reference signal n'(t) is determined by:

$$n'(t) = S_{\lambda a}(t) - \omega_{av} S_{\lambda b}(t) = n_{\lambda a}(t) - \omega_{av} n_{\lambda b}(t) \qquad (99)$$

This secondary reference signal n'(t) has spectral content corresponding to the erratic, motion-induced noise. When it is input to a correlation canceler, such as an adaptive noise canceler, with either the signals $S_{\lambda a}(t)$ and $S_{\lambda c}(t)$ or $S_{\lambda b}(t)$ and $S_{\lambda c}(t)$ input to two regression filters 80a and 80b as in FIG. 10, the adaptive noise canceler will function much like an adaptive multiple notch filter and remove frequency components present in both the secondary reference signal n'(t) and the measured signals from the measured signals $S_{\lambda a}(t)$ and $S_{\lambda c}(t)$ or $S_{\lambda b}(t)$ and $S_{\lambda c}(t)$. If the secondary reference signal n'(t) is correlated to the venous portion, then the adaptive noise canceler is able to remove erratic noise caused in the venous portion of the measured signals $S_{\lambda a}(t)$, $S_{\lambda b}(t)$, and $S_{\lambda c}(t)$ even though the venous portion of the measured signals $S_{\lambda a}(t)$ and $S_{\lambda b}(t)$ was not incorporated in the secondary reference signal n'(t). In the event that the secondary reference signal n'(t) is not correlated to the venous component, then, the adaptive noise canceler generally will not remove the venous portion from the measured signals. However, a band pass filter applied to the approximations to the primary signals $s''_{\lambda a}(t)$ and $s''_{\lambda c}(t)$ or $s''_{\lambda b}(t)$ and $s''_{\lambda c}(t)$ can remove the low frequency venous signal due to breathing.

For pulse oximetry measurements using the constant saturation method, the signals (logarithm converted) transmitted through the finger 310 at each wavelength λa and λb are:

$$S_{\lambda a}(t) = S_{\lambda red1}(t) = \epsilon_{HbO2,\lambda a} c^A_{HbO2} x^A(t) + \epsilon_{Hb,\lambda a} c^A_{Hb} x^A(t) + \epsilon_{HbO2,\lambda a} c^V_{HbO2} x^V(t) + \epsilon_{Hb,\lambda a} c^V_{Hb} x^V(t) + n_{\lambda a}(t);$$ (100a)

$$S_{\lambda a}(t) = \epsilon_{HbO2,\lambda a} c^A_{HbO2} x^A(t) + \epsilon_{Hb,\lambda a} c^A_{Hb} x^A(t) + n_{\lambda a}(t);$$ (100b)

$$S_{\lambda a}(t) = s_{\lambda a}(t) + n_{\lambda a}(t);$$ (100c)

$$S_{\lambda b}(t) = S_{\lambda red2}(t) = \epsilon_{HbO2,\lambda b} c^A_{HbO2} x^A(t) + \epsilon_{Hb,\lambda b} c^A_{Hb} x^A(t) + \epsilon_{HbO2,\lambda b} c^V_{HbO2} x^V(t) + \epsilon_{Hb,\lambda b} c^V_{Hb} x^V(t) + n_{\lambda b}(t);$$ (101a)

$$S_{\lambda b}(t) = \epsilon_{HbO2,\lambda b} c^A_{HbO2} x^A(t) + \epsilon_{Hb,\lambda b} c^A_{Hb} x^A(t) + n_{\lambda b}(t);$$ (101b)

$$S_{\lambda b}(t) = s_{\lambda b}(t) + n_{\lambda b}(t).$$ (101c)

For the constant saturation method, the wavelengths chosen are typically one in the visible red range, i.e., λa, and one in the infrared range, i.e., λb. Typical wavelength values chosen are λa=660 nm and λb=940 nm. Using the constant saturation method, it is assumed that $c^A_{HbO2}(t)/c^A_{Hb}(t)$=constant$_1$ and $c^V_{HbO2}(t)/c^V_{Hb}(t)$=constant$_2$. The oxygen saturation of arterial and venous blood changes slowly, if at all, with respect to the sample rate, making this a valid assumption. The proportionality factors for equations (100) and (101) can then be written as:

$$\omega_a(t) = \frac{\epsilon_{HbO2,\lambda a} c^A_{HbO2} x(t) + \epsilon_{Hb,\lambda a} c_{Hb} x(t)}{\epsilon_{HbO2,\lambda b} c^A_{HbO2} x(t) + \epsilon_{Hb,\lambda b} c_{Hb} x(t)} *$$ (102)

$$s_{\lambda a}(t) = \omega_a(t) s_{\lambda b}(t)$$ (103a)

$$n_{\lambda a}(t) \neq \omega_a(t) n_{\lambda b}(t)$$ (104a)

$$n_{\lambda a}(t) = \omega_v(t) n_{\lambda b}(t)$$ (103b)

$$s_{\lambda a}(t) \neq \omega_v(t) s_{\lambda b}(t)$$ (104b)

In pulse oximetry, it is typically the case that both equations (103) and (104) can be satisfied simultaneously.

Multiplying equation (101) by $\omega_a(t)$ and then subtracting equation (101) from equation (100), a non-zero secondary reference signal n'(t) is determined by:

$$n'(t) = S_{\lambda a}(t) - \omega_a(t) S_{\lambda b}(t)$$ (105a)

$$= \epsilon_{HbO2,\lambda a} c^V_{HbO2} x^V(t) + \epsilon_{Hb,\lambda a} c^V_{Hb} x^V(t) + n_{\lambda a}(t) -$$

$$\omega_a(t) [\epsilon_{HbO2,\lambda b} c^V_{HbO2} x^V(t) + \epsilon_{Hb,\lambda b} c^V_{Hb} x^V(t) + n_{\lambda b}(t)]$$ (106a)

Multiplying equation (101) by $\omega_v(t)$ and then subtracting equation (101) from equation (100), a non-zero primary reference signal s'(t) is determined by:

$$s'(t) = S_{\lambda a}(t) - \omega_v(t) S_{\lambda b}(t)$$ (105b)

$$= s_{\lambda a}(t) - \omega_v(t) s_{\lambda b}(t)$$ (106b)

The constant saturation assumption does not cause the venous contribution to the absorption to be canceled along with the primary signal portions $s_{\lambda a}(t)$ and $s_{\lambda b}(t)$, as did the relationship of equation (96) used in the ratiometric method. Thus, frequencies associated with both the low frequency modulated absorption due to venous absorption when the patient is still and the erratically modulated absorption due to venous absorption when the patient is moving are represented in the secondary reference signal n'(t). Thus, the correlation canceler can remove or derive both erratically modulated absorption due to venous blood in the finger under motion and the constant low frequency cyclic absorption of venous blood.

Using either method, a primary reference s'(t) or a secondary reference n'(t) is determined by the processor of the present invention for use in a correlation canceler, such as an adaptive noise canceler, which is defined by software in the microprocessor. The preferred adaptive noise canceler is the joint process estimator 60 described above.

Figure 15:
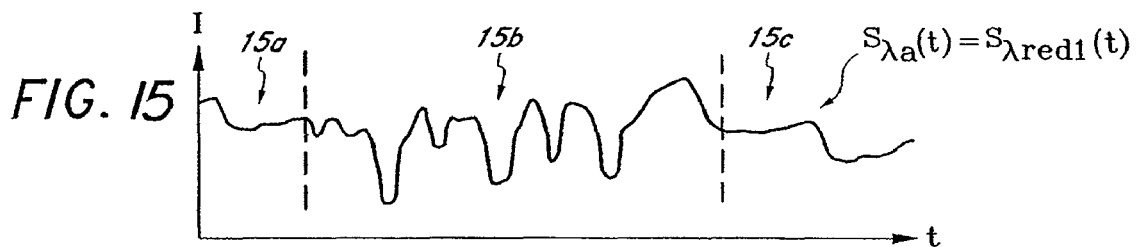
FIG. 15 illustrates a signal measured at a first red wavelength $\lambda a = \lambda red1 = 650$ nm for use in a processor of the present invention employing the ratiometric method for determining either the primary reference n'(t) or the secondary reference s'(t) and for use in a correlation canceler, such as an adaptive noise canceler. The measured signal comprises a primary portion $s_{\lambda,a}(t)$ and a secondary portion $n_{\lambda,a}(t)$.
Figure 16:
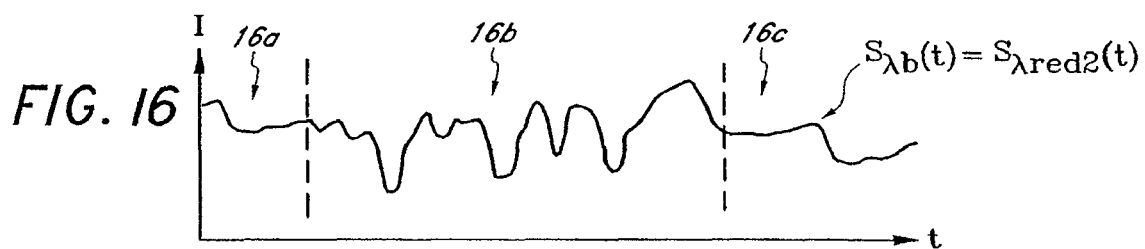
FIG. 16 illustrates a signal measured at a second red wavelength $\lambda b = \lambda red2 = 685$ nm for use in a processor of the present invention employing the ratiometric method for determining the secondary reference n'(t) or the primary reference s'(t). The measured signal comprises a primary portion $s_{\lambda,b}(t)$ and a secondary portion $n_{\lambda,b}(t)$.
Figure 17:
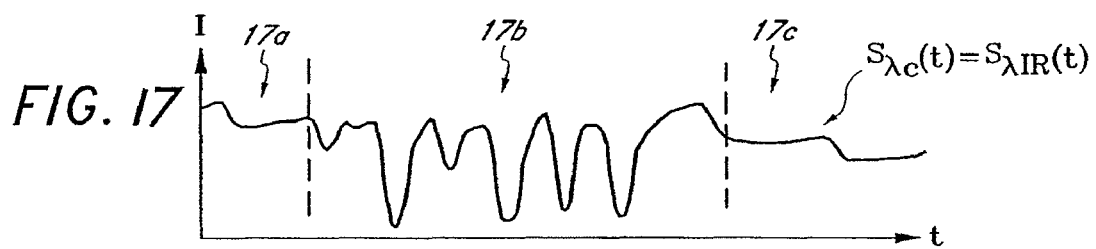
FIG. 17 illustrates a signal measured at an infrared wavelength $\lambda c = \lambda IR = 940$ nm for use in a correlation canceler. The measured signal comprises a primary portion $s_{\lambda,c}(t)$ and a secondary portion $n_{\lambda,c}(t)$.

Illustrating the operation of the ratiometric method of the present invention, FIGS. 15, 16 and 17 show signals measured for use in determining the saturation of oxygenated arterial blood using a reference processor of the present invention which employs the ratiometric method, i.e., the signals $S_{\lambda a}(t)=S_{\lambda red1}(t)$, $S_{\lambda b}(t) S_{\lambda red2}(t)$, and $S_{\lambda c}(t)=S_{\lambda IR}(t)$. A first segment 15a, 16a, and 17a of each of the signals is relatively undisturbed by motion artifact, i.e., the patient did not move substantially during the time period in which these segments were measured. These segments 15a, 16a, and 17a are thus generally representative of the plethysmographic waveform at each of the measured wavelengths. These waveforms are taken to be the primary signals $s_{\lambda a}(t)$, $s_{\lambda b}(t)$, and $s_{\lambda c}(t)$. A second segment 15b, 16b, and 17b of each of the signals is affected by motion artifact, i.e., the patient did move during the time period in which these segments were measured. Each of these segments 15b, 16b, and 17b shows large motion induced excursions in the measured signal. These waveforms contain both primary plethysmographic signals and secondary motion induced excursions. A third segment 15c, 16c, and 17c of each of the signals is again relatively unaffected by motion artifact and is thus generally representative of the plethysmographic waveform at each of the measured wavelengths.

Figure 18:
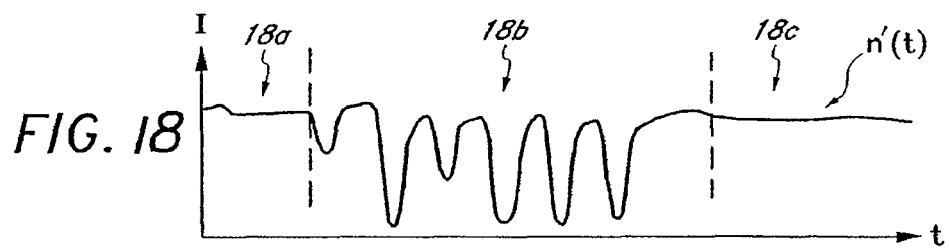
FIG. 18 illustrates the secondary reference n'(t) determined by a processor of the present invention using the ratiometric method.

FIG. 18 shows the secondary reference signal n'(t)=$n_{\lambda a}-\omega_a v\, n_{\lambda a}(t)$, as determined by a reference processor of the present invention utilizing the ratiometric method. As discussed previously, the secondary reference signal n'(t) is correlated to the secondary signal portions $n_{\lambda a}$, $n_{\lambda b}$, and $n_{\lambda c}$. Thus, a first segment 18a of the secondary reference signal n'(t) is generally flat, corresponding to the fact that there is very little motion induced noise in the first segments 15a, 16a, and 17a of each signal. A second segment 18b of the secondary reference signal n'(t) exhibits large excursions, corresponding to the large motion induced excursions in each of the measured signals. A third segment 18c of the secondary reference signal n'(t) is generally flat, again corresponding to the lack of motion artifact in the third segments 15c, 16c, and 17c of each measured signal.

Figure 19:
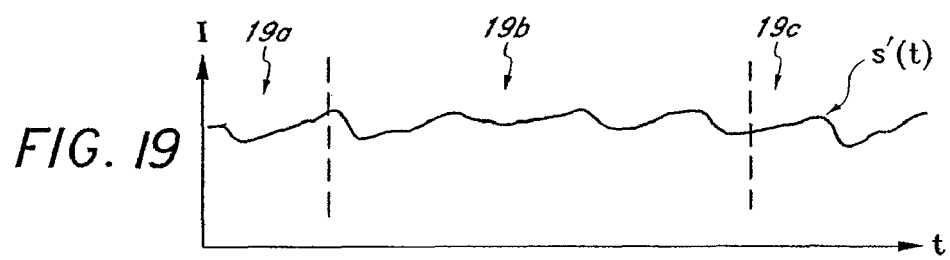
FIG. 19 illustrates the primary reference s'(t) determined by a processor of the present invention using the ratiometric method.

FIG. 19 shows the primary reference signal s'(t)=$s_{\lambda a}-\omega_e s_{\lambda b}(t)$, as determined by a reference processor of the present invention utilizing the ratiometric method. As discussed previously, the primary reference signal s'(t) is correlated to the primary signal portions $s_{\lambda a}(t)$, $s_{\lambda b}(t)$, and $s_{\lambda c}(t)$. Thus, a first segment 19a of the primary reference signal s'(t) is indicative of the plethysmographic waveform, corresponding to the fact that there is very little motion induced noise in the first segments 15a, 16a, and 17a of each signal. A second segment 19b of the primary reference signal s'(t) also exhibits a signal related to a plethymographic waveform, corresponding to each of the measured signals in the absence of the large motion induced excursions. A third segment 19c of the primary reference signal s'(t) is generally indicative of the plethysmographic waveform, again corresponding to the lack of motion artifact in the third segments 15c, 16c, and 17c of each measured signal.

Figure 20:
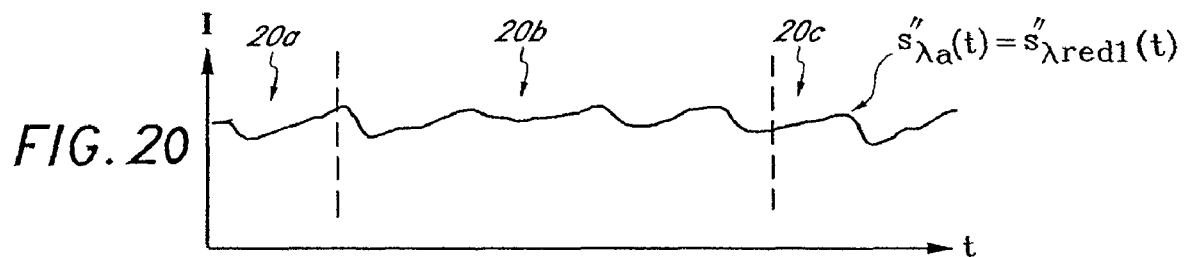
FIG. 20 illustrates a good approximation $s''_{\lambda,a}(t)$ to the primary portion $s_{\lambda,a}(t)$ of the signal $s_{\lambda,a}(t)$ measured at $\lambda a = \lambda red1 = 650$ nm estimated by correlation cancellation with a secondary reference n'(t) determined by the ratiometric method.
Figure 21:
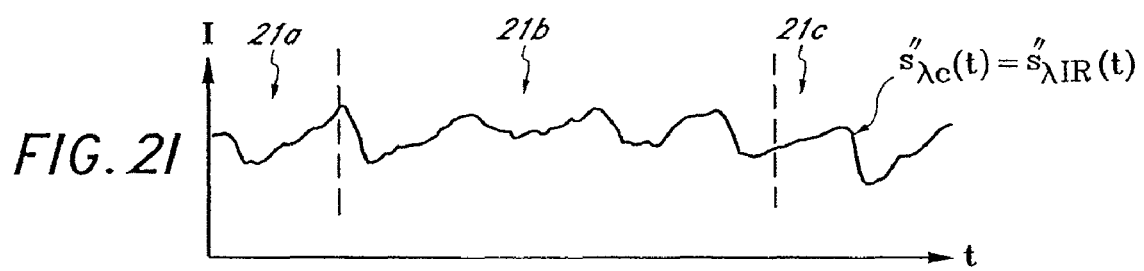
FIG. 21 illustrates a good approximation $s''_{\lambda,c}(t)$ to the primary portion $s_{\lambda,c}(t)$ of the signal $s_{\lambda,c}(t)$ measured at $\lambda c = \lambda IR = 940$ nm estimated by correlation cancellation with a secondary reference n'(t) determined by the ratiometric method.

FIGS. 20 and 21 show the approximations $s''_{\lambda a}(t)$ and $s''_{\lambda c}(t)$ to the primary signals $s_{\lambda a}(t)$ and $s_{\lambda c}(t)$ as estimated by the correlation canceler 27 using a secondary reference signal n'(t) determined by the ratiometric method. FIGS. 20 and 21 illustrate the effect of correlation cancelation using the secondary reference signal n'(t) as determined by the reference processor of the present invention using the ratiometric method. Segments 20b and 21b are not dominated by motion induced noise as were segments 15b, 16b, and 17b of the measured signals. Additionally, segments 20a, 21a, 20c, and 21c have not been substantially changed from the measured signal segments 15a, 17a, 15c, and 17c where there was no motion induced noise.

Figure 22:
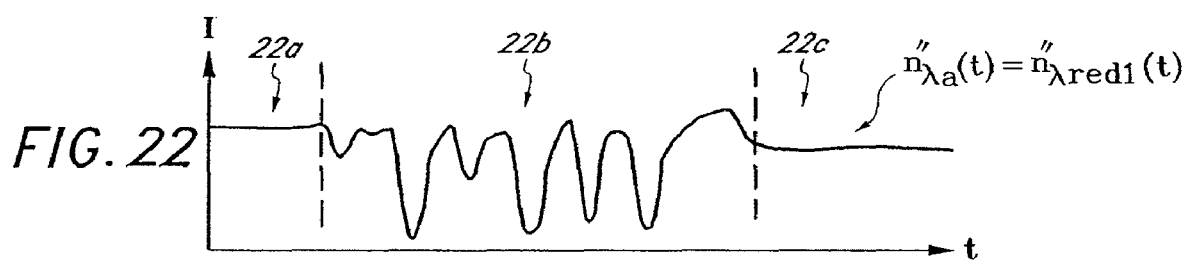
FIG. 22 illustrates a good approximation $n''_{\lambda,a}(t)$ to the secondary portion $n_{\lambda,a}(t)$ of the signal $S_{\lambda,a}(t)$ measured at $\lambda a = \lambda red1 = 650$ nm estimated by correlation cancellation with a primary reference s'(t) determined by the ratiometric method.
Figure 23:
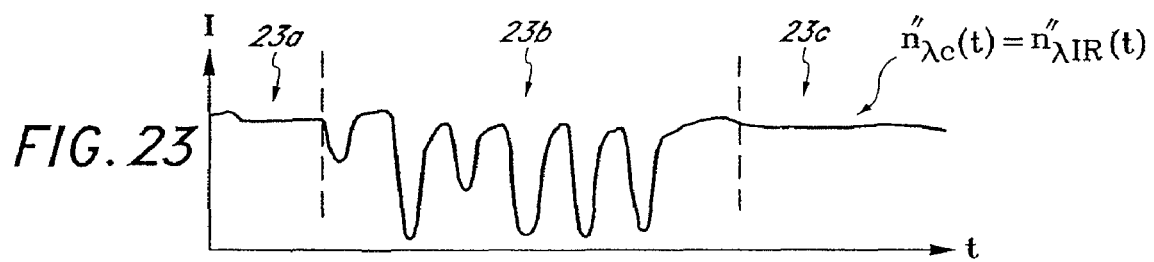
FIG. 23 illustrates a good approximation $n''_{\lambda,c}(t)$ to the secondary portion $n_{\lambda,c}(t)$ of the signal $S_{\lambda,c}(t)$ measured at $\lambda c = \lambda IR = 940$ nm estimated by correlation cancelation with a primary reference s'(t) determined by the ratiometric method.

FIGS. 22 and 23 show the approximations $n''_{\lambda a}(t)$ and $n''_{\lambda c}(t)$ to the primary signals $n_{\lambda a}(t)$ and $n_{\lambda c}(t)$ as estimated by the correlation canceler 27 using a primary reference signal s'(t) determined by the ratiometric method. Note that the scale of FIGS. 15 through 23 is not the same for each figure to better illustrate changes in each signal. FIGS. 22 and 23 illustrate the effect of correlation cancelation using the primary reference signal s'(t) as determined by the reference processor of the present invention using the ratiometric method. Only segments 22b and 23b are dominated by motion induced noise as were segments 15b, 16b, and 17b of the measured signals. Additionally, segments 22a, 23a, 22c, and 23c are nearly zero corresponding to the measured signal segments 15a, 17a, 15c, and 17c where there was no motion induced noise.

Figure 24:
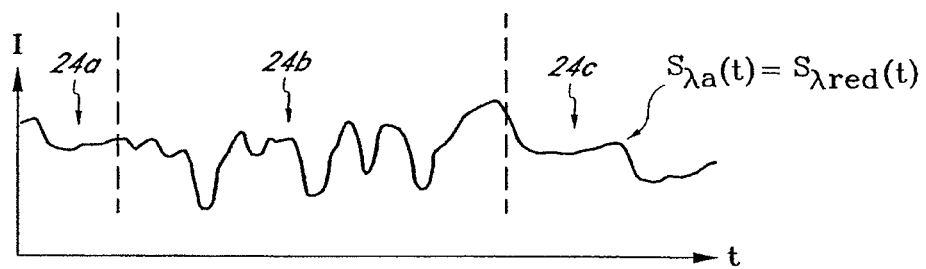
FIG. 24 illustrates a signal measured at a red wavelength $\lambda a = \lambda red = 660$ nm for use in a processor of the present invention employing the constant saturation method for determining the secondary reference n'(t) or the primary reference s'(t) and for use in a correlation canceler. The measured signal comprises a primary portion $s_{\lambda,a}(t)$ and a secondary portion $n_{\lambda,a}(t)$.
Figure 25:
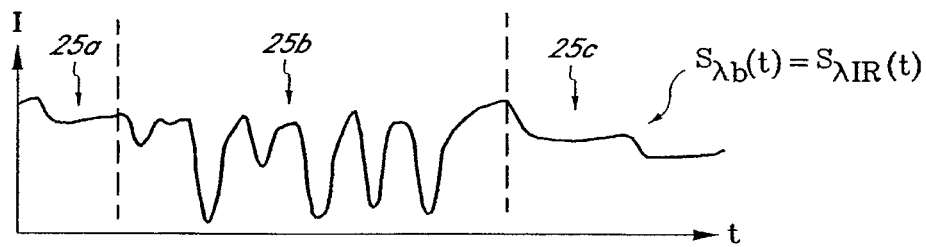
FIG. 25 illustrates a signal measured at an infrared wavelength $\lambda b = \lambda IR = 940$ nm for use in a processor of the present invention employing the constant saturation method for determining the secondary reference n'(t) or the primary reference s'(t) and for use in a correlation canceler. The measured signal comprises a primary portion $s_{\lambda,b}(t)$ and a secondary portion $n_{\lambda,b}(t)$.

Illustrating the operation of the constant saturation method of the present invention, FIGS. 24 and 25 show signals measured for input to a reference processor of the present invention which employs the constant saturation method, i.e., the signals $S_{\lambda a}(t)=S_{\lambda red}(t)$ and $S\lambda b(t)=S_{\lambda IR}(t)$. A first segment 24a and 25a of each of the signals is relatively undisturbed by motion artifact, i.e., the patient did not move substantially during the time period in which these segments were measured. These segments 24a and 25a are thus generally representative of the primary plethysmographic waveform at each of the measured wavelengths. A second segment 24b and 25b of each of the signals is affected by motion artifact, i.e., the patient did move during the time period in which these segments were measured. Each of these segments 24b and 25b shows large motion induced excursions in the measured signal. A third segment 24c and 25c of each of the signals is again relatively unaffected by motion artifact and is thus generally representative of the primary plethysmographic waveform at each of the measured wavelengths.

Figure 26:
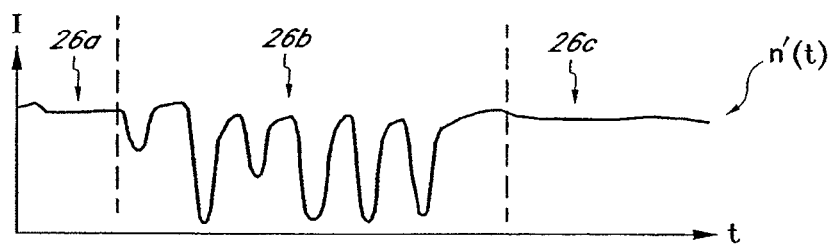
FIG. 26 illustrates the secondary reference n'(t) determined by a processor of the present invention using the constant saturation method.

FIG. 26 shows the secondary reference signal $n'(t)=n_{\lambda a}(t)-\omega_a n_{\lambda a}(t)$, as determined by a reference processor of the present invention utilizing the constant saturation method. Again, the secondary reference signal n'(t) is correlated to the secondary signal portions $n_{\lambda a}$ and $n_{\lambda b}$. Thus, a first segment 26a of the secondary reference signal n'(t) is generally flat, corresponding to the fact that there is very little motion induced noise in the first segments 24a and 25a of each signal. A second segment 26b of the secondary reference signal n'(t) exhibits large excursions, corresponding to the large motion induced excursions in each of the measured signals. A third segment 26c of the noise reference signal n'(t) is generally flat, again corresponding to the lack of motion artifact in the third segments 24c and 25c of each measured signal.

Figure 27:
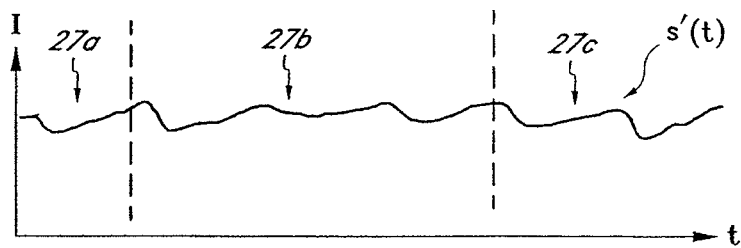
FIG. 27 illustrates the primary reference s'(t) determined by a processor of the present invention using the constant saturation method.

FIG. 27 shows the primary reference signal $s'(t)=s_{\lambda a}-\omega_v s_{\lambda b}(t)$, as determined by a reference processor of the present invention utilizing the constant saturation method. As discussed previously, the primary reference signal s'(t) is correlated to the primary signal portions $s_{\lambda a}(t)$ and $s_{\lambda b}(t)$. Thus, a first segment 27a of the primary reference signal s'(t) is indicative of the plethysmographic waveform, corresponding to the fact that there is very little motion induced noise in the first segments 24a and 25a of each signal. A second segment 27b of the primary reference signal s'(t) also exhibits a signal related to a plethymographic waveform, corresponding to each of the measured signals in the absence of the large motion induced excursions. A third segment 27c of the primary reference signal s'(t) is generally indicative of the plethysmographic waveform, again corresponding to the lack of motion artifact in the third segments 24c and 25c of each measured signal.

Figure 28:
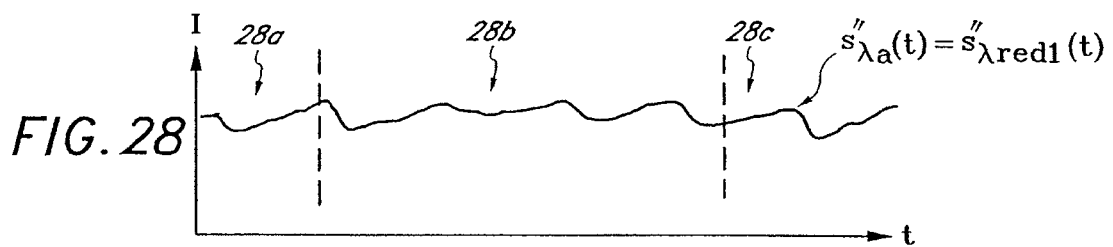
FIG. 28 illustrates a good approximation $s''_{\lambda,a}(t)$ to the primary portion $s_{\lambda,a}(t)$ of the signal $S_{\lambda,a}(t)$ measured at $\lambda a = \lambda red = 660$ nm estimated by correlation cancelation with a secondary reference n'(t) determined by the constant saturation method.
Figure 29:
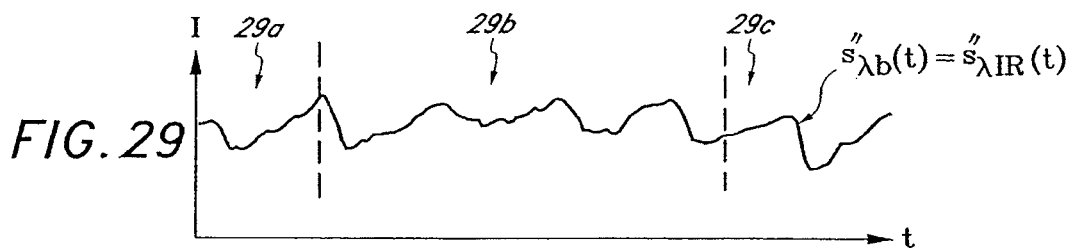
FIG. 29 illustrates a good approximation $s''_{\lambda,b}(t)$ to the primary portion $s_{\lambda,b}(t)$ of the signal $S_{\lambda,b}(t)$ measured at $\lambda b = \lambda IR = 940$ nm estimated by correlation cancelation with a secondary reference n'(t) determined by the constant saturation method.

FIGS. 28 and 29 show the approximations $s''_{\lambda a}(t)$ and $s''_{\lambda b}(t)$ to the primary signals $s_{\lambda a}(t)$ and $s_{\lambda b}(t)$ as estimated by the correlation canceler 27 using a secondary reference signal n'(t) determined by the constant saturation method. FIGS. 28 and 29 illustrate the effect of correlation cancelation using the secondary reference signal n'(t) as determined by a reference processor of the present invention utilizing the constant saturation method. Segments 28b and 28b are not dominated by motion induced noise as were segments 24b and 25b of the measured signals. Additionally, segments 28a, 29a, 28c, and 29c have not been substantially changed from the measured signal segments 24a, 25a, 24c, and 25c where there was no motion induced noise.

Figure 30:
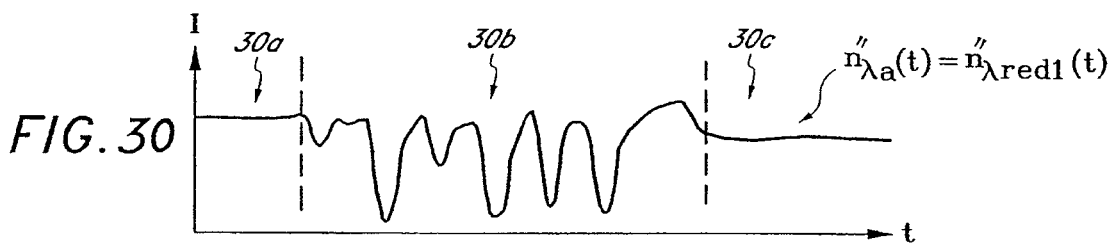
FIG. 30 illustrates a good approximation $n''_{\lambda,a}(t)$ to the secondary portion $n_{\lambda,a}(t)$ of the signal $S_{\lambda,a}(t)$ measured at $\lambda a = \lambda red = 660$ nm estimated by correlation cancelation with a primary reference s'(t) determined by the constant saturation method.
Figure 31:
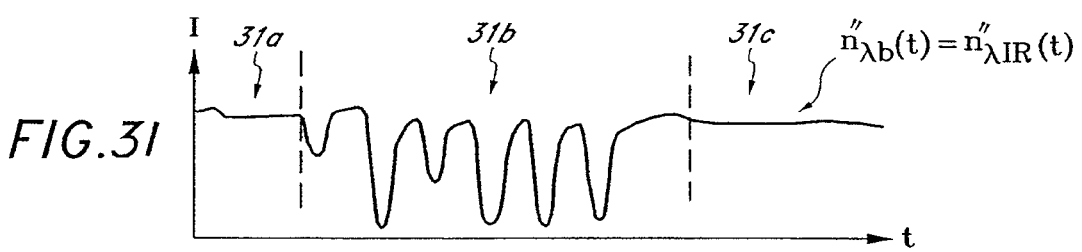
FIG. 31 illustrates a good approximation $n''_{\lambda,b}(t)$ to the secondary portion $n_{\lambda,b}(t)$ of the signal $S_{\lambda,b}(t)$ measured at $\lambda b = \lambda IR = 940$ nm estimated by correlation cancelation with a primary reference s'(t) determined by the constant saturation method.

FIGS. 30 and 31 show the approximations $n''_{\lambda a}(t)$ and $n''_{\lambda b}(t)$ to the secondary signals $n_{\lambda a}(t)$ and $n_{\lambda b}(t)$ as estimated by the correlation canceler 27 using a primary reference signal s'(t) determined by the constant saturation method. Note that the scale of FIGS. 24 through 31 is not the same for each figure to better illustrate changes in each signal. FIGS. 30 and 31 illustrate the effect of correlation cancelation using the primary reference signal s'(t) as determined by a reference processor of the present invention utilizing the constant saturation method. Only segments 30b and 31b are dominated by motion induced noise as were segments 24b, and 25b of the measured signals. Additionally, segments 30a, 31a, 30c, and 31c are nearly zero corresponding to the measured signal segments 24a, 25a, 24c, and 25c where there was no motion induced noise.

Method for Estimating Primary and Secondary Signal Portion of Measured Signals in a Pulse Oximeter A copy of a computer subroutine, written in the C programming language, calculates a primary reference s'(t) and a secondary reference n'(t) using the ratiometric method and, using a joint process estimator 60, estimates either the primary or secondary signal portions of two measured signals, each having a primary signal which is correlated with the primary reference s'(t) and having a secondary signal which is correlated with the secondary reference n'(t), is appended in Appendix A. For example, $S_{\lambda a}(t)=S_{\lambda red}(t)=S_{\lambda 660nm}(t)$ and $S_{\lambda b}(t)=S_{\lambda IR}(t)=S_{\lambda 940nm}(t)$ can be input to the computer subroutine. This subroutine is one way to implement the steps illustrated in the flowchart of FIG. 9 for a monitor particularly adapted for pulse oximetry.

The program estimates either the primary signal portions or the secondary signal portions of two light energy signals, one preferably corresponding to light in the visible red range and the other preferably corresponding to light in the infrared range such that a determination of the amount of oxygen, or the saturation of oxygen in the arterial and venous blood components, may be made. The calculation of the saturation is performed in a separate subroutine.

Using the ratiometric method three signals $S_{\lambda a}(t)$, $S_{\lambda b}(t)$ and $S_{\lambda c}(t)$ are input to the subroutine. $S_{\lambda a}(t)$ and $S_{\lambda b}(t)$ are used to calculate either the primary or secondary reference signal s'(t) or n'(t). As described above, the wavelengths of light at which $S_{\lambda a}(t)$ and $S_{\lambda b}(t)$ are measured are chosen to satisfy the relationship of equation (96). Once either the secondary reference signal n'(t) or the primary reference signal s'(t) is determined, either the primary signal portions $s_{\lambda a}(t)$ and $s_{\lambda c}(t)$ or the secondary signal portions $n_{\lambda a}(t)$ and $n_{\lambda c}(t)$ of the measured signals $S_{\lambda a}(t)$ and $S_{\lambda c}(t)$ are estimated for use in calculation of the oxygen saturation.

The correspondence of the program variables to the variables defined in the discussion of the joint process estimator is as follows:

$\Delta_m(t) = nc[m] \cdot \text{Delta}$ $\Gamma_{f,m}(t) = nc[m] \cdot \text{fref}$ $\Gamma_{b,m}(t) = nc[m] \cdot \text{bref}$ $f_m(t) = nc[m] \cdot \text{ferr}$ $b_m(t) = nc[m] \cdot \text{berr}$ $J_m(t) = nc[m] \cdot \text{Fswsqr}$ $\beta_m(t) = nc[m] \cdot \text{Bswsqr}$ $\gamma_m(t) = nc[m] \cdot \text{Gamma}$ $\rho_{m,\lambda a}(t) = nc[m] \cdot \text{Roh\_a}$ $\rho_{m,\lambda c}(t) = nc[m] \cdot \text{Roh\_c}$ $e_{m,\lambda a}(t) = nc[m] \cdot \text{err\_a}$ $e_{m,\lambda c}(t) = nc[m] \cdot \text{err\_c}$ $\kappa_{m,\lambda a}(t) = nc[m] \cdot \text{K\_a}$ $\kappa_{m,\lambda c}(t) = nc[m] \cdot \text{K\_c}$ A first portion of the program performs the initialization of the registers 90, 92, 96, and 98 and intermediate variable values as in the "INITIALIZE CORRELATION CANCELER" box 120 and equations (52) through (56) and equations (73), (74), (77), and (78). A second portion of the program performs the time updates of the delay element variables 110 where the value at the input of each delay element variable 110 is stored in the delay element variable 110 as in the "TIME UPDATE OF [$Z^{-1}$] ELEMENTS" box 130.

A third portion of the program calculates the reference signal, as in the "CALCULATE SECONDARY REFERENCE (n'(t)) OR PRIMARY REFERENCE (s'(t)) FOR TWO MEASURED SIGNAL SAMPLES" box 140 using the proportionality constant $\omega_a v$ determined by the ratiometric method as in equation (25).

A fourth portion of the program performs the zero-stage update as in the "ZERO-STAGE UPDATE" box 150 where the zero-stage forward prediction error $f_0(t)$ and the zero-stage backward prediction error $b_0(t)$ are set equal to the value of the reference signal n'(t) or s'(t) just calculated. Additionally, zero-stage values of intermediate variables $J_0(t)$ and $\beta_0(t)$ (nc[m]·Fswsqr and nc[m]·Bswsqr in the program) are calculated for use in setting register 90, 92, 96, and 98 values in the least-squares lattice predictor 70 and the regression filters 80a and 80b.

A fifth portion of the program is an iterative loop wherein the loop counter, m, is reset to zero with a maximum of m=NC_CELLS, as in the "m=0" box 160 in FIG. 9. NC_CELLS is a predetermined maximum value of iterations for the loop. A typical value of NC_CELLS is between 6 and 10, for example. The conditions of the loop are set such that the loop iterates a minimum of five times and continues to iterate until a test for conversion is met or m=NC_CELLS. The test for conversion is whether or not the sum of the weighted sum of forward prediction errors plus the weighted sum of backward prediction errors is less than a small number, typically 0.00001 (i.e, $J_m(t) + \beta_m(t) \leq 0.00001$).

A sixth portion of the program calculates the forward and backward reflection coefficient $\Gamma_{m,f}(t)$ and $\Gamma_{m,b}(t)$ register 90 and 92 values (nc[m]·fref and nc[m]·bref in the program) as in the "ORDER UPDATE $m^{th}$-STAGE OF LSL-PREDICTOR" box 170 and equations (61) and (62). Then forward and backward prediction errors $f_m(t)$ and $b_m(t)$ (nc[m]·ferr and nc[m]·berr in the program) are calculated as in equations (63) and (64). Additionally, intermediate variables $J_m(t)$, $\beta_m(t)$ and $\gamma_m(t)$ (nc[m]·Fswsqr, nc[m]·Bswsqr, nc[m]·Gamma in the program) are calculated, as in equations (65), (66), and (67). The first cycle of the loop uses the values for nc[0]·Fswsqr and nc[0]·Bswsqr calculated in the ZERO-STAGE UPDATE portion of the program.

A seventh portion of the program, still within the loop, calculates the regression coefficient $\kappa_{m,\lambda a}(t)$ and $\kappa_{m,\lambda c}(t)$ register 96 and 98 values (nc[m]·K_a and nc[m]·K_c in the program) in both regression filters, as in the "ORDER UPDATE $m^{th}$ STAGE OF REGRESSION FILTER(S)" box 180 and equations (68) through (80). Intermediate error signals and variables $e_{m,\lambda a}(t)$, $e_{m,\lambda c}(t)$, $\rho.m_{,\lambda a}(t)$, and $\rho_{m,\lambda c}(t)$ (nc[m]·err_a and nc[m]·err_c, nc[m]·roh_a, and nc[m]·roh_c in the subroutine) are also calculated as in equations (75), (76), (71), and (72), respectively.

The test for convergence of the joint process estimator is performed each time the loop iterates, analogously to the "DONE" box 190. If the sum of the weighted sums of the forward and backward prediction errors $J_m(t) + \beta_m(t)$ is less than or equal to 0.00001, the loop terminates. Otherwise, the sixth and seventh portions of the program repeat.

When either the convergence test is passed or m=NC_CELLS, an eighth portion of the program calculates the output of the joint process estimator 60 as in the "CALCULATE OUTPUT" box 200. This output is a good approximation to both of the primary signals $s''_{\lambda a}(t)$ and $s''_{\lambda c}(t)$ or the secondary signals $n''_{\lambda a}(t)$ and $n''_{\lambda c}(t)$ for the set of samples $S_{\lambda a}(t)$ and $S_{\lambda c}(t)$, input to the program. After many sets of samples are processed by the joint process estimator, a compilation of the outputs provides output waves which are good approximations to the plethysmographic wave or motion artifact at each wavelength, λa and λc.

Another copy of a computer program subroutine, written in the C programming language, which calculates either a primary reference s'(t) or a secondary reference n'(t) using the constant saturation method and, using a joint process estimator 60, estimates a good approximation to either the primary signal portions or secondary signal portions of two measured signals, each having a primary portion which is correlated to the primary reference signal s'(t) and a secondary portion which is correlated to the secondary reference signal n'(t) and each having been used to calculate the reference signals s'(t) and n'(t), is appended in Appendix B. This subroutine is another way to implement the steps illustrated in the flowchart of FIG. 9 for a monitor particularly adapted for pulse oximetry. The two signals are measured at two different wavelengths λa and λb, where λa is typically in the visible region and λb is typically in the infrared region. For example, in one embodiment of the present invention, tailored specifically to perform pulse oximetry using the constant saturation method, λa=660 nm and λb=940 nm.

The correspondence of the program variables to the variables defined in the discussion of the joint process estimator is as follows:

$\Delta_m(t)$=nc[m]·Delta $\Gamma_{f,m}(t)$=nc[m]·fref $\Gamma_{b,m}(t)$=nc[m]·bref $f_m(t)$=nc[m]·ferr $b_m(t)$=nc[m]·berr $\Im_m(t)$=nc[m]·Fswsqr $\beta_m(t)$=nc[m]·Bswsqr $\gamma_m(t)$=nc[m]·Gamma $\rho_{m,\lambda a}(t)$=nc[m]·Roh_a $\rho_{m,\lambda b}(t)$=nc[m]·Roh_b $e_{m,\lambda a}(t)$=nc[m]·err_a $e_{m,\lambda b}(t)$=nc[m]·err_b $\kappa_{m,\lambda a}(t)$=nc[m]·K_a $\kappa_{m,\lambda b}(t)$=nc[m]·K_b First and second portions of the subroutine are the same as the first and second portions of the above described subroutine tailored for the ratiometric method of determining either the primary reference s'(t) or the noise reference n'(t). The calculation of saturation is performed in a separate module. Various methods for calculation of the oxygen saturation are known to those skilled in the art. One such calculation is described in the articles by G. A. Mook, et al, and Michael R. Neuman cited above. Once the concentration of oxygenated hemoglobin and deoxygenated hemoglobin are determined, the value of the saturation is determined similarly to equations (85) through (92) wherein measurements at times $t_1$ and $t_2$ are made at different, yet proximate times over which the saturation is relatively constant. For pulse oximetry, the average saturation at time $t=(t_1+t_2)/2$ is then determined by:

$$Saturation_{Art}(t) = \frac{C^A_{Hb02}(t)}{C^A_{Hb02}(t) + C^A_{Hb}(t)} \quad (107)$$

$$= \frac{\epsilon_{Hb,\lambda a} - \epsilon_{Hb,\lambda b}(\Delta S_{\lambda a}/\Delta S_{\lambda b})}{\epsilon_{HB,\lambda a} - \epsilon_{Hb02,\lambda a} - (\epsilon_{HB,\lambda b} - \epsilon_{Hb02,\lambda b})(\Delta S_{\lambda a}/\Delta S_{\lambda b})} \quad (107b)$$

$$Saturation_{Ven}(t) = \frac{C^V_{Hb02}(t)}{C^V_{Hb02}(t) + C^V_{Hb}(t)} \quad (108a)$$

$$= \frac{\epsilon_{Hb,\lambda a} - \epsilon_{Hb,\lambda b}(\Delta n_{\lambda a}/\Delta n_{\lambda b})}{\epsilon_{HB,\lambda a} - \epsilon_{Hb02,\lambda a} - (\epsilon_{HB,\lambda b} - \epsilon_{Hb02,\lambda b})(\Delta n_{\lambda a}/\Delta n_{\lambda b})} \quad (108b)$$

A third portions of the subroutine calculates either the primary reference or secondary reference, as in the "CALCULATE PRIMARY OR SECONDARY REFERENCE (s' (t) or n'(t)) FOR TWO MEASURED SIGNAL SAMPLES" box 140 for the signals $S_{\lambda,a}(t)$ and $S_{\lambda,b}(t)$ using the proportionality constants $\omega_a(t)$ and $\omega_v(t)$ determined by the constant saturation method as in equation (3). The saturation is calculated in a separate subroutine and a value of $\omega_a(t)$ or $\omega_v(t)$ is imported to the present subroutine for estimating either the primary portions $s_{\lambda,a}(t)$ and $s_{\lambda,b}(t)$ or the secondary portions $n_{\lambda,a}(t)$ and $n_{\lambda,b}(t)$ of the composite measured signals $S_{\lambda,a}(t)$ and $S_{\lambda,b}(t)$.

Fourth, fifth, and sixth portions of the subroutine are similar to the fourth, fifth, and sixth portions of the above described program tailored for the ratiometric method. However, the signals being used to estimate the primary signal portions $s_{\lambda,a}(t)$ and $s_{\lambda,b}(t)$ or the secondary signal portions $n_{\lambda,a}(t)$ and $n_{\lambda,b}(t)$ in the present subroutine tailored for the constant saturation method, are $S_{\lambda,a}(t)$ and $S_{\lambda,b}(t)$, the same signals that were used to calculate the reference signal s'(t) or n'(t).

A seventh portion of the program, still within the loop begun in the fifth portion of the program, calculates the regression coefficient register 96 and 98 values $\kappa_{m,\lambda a}(t)$ and $\kappa_{m,\lambda b}(t)$ (nc[m]·K_a and nc[m]·K_b in the program) in both regression filters, as in the "ORDER UPDATE $m^{th}$ STAGE OF REGRESSION FILTER(S)" box 180 and equations (68) through (80). Intermediate error signals and variables $e_{m,\lambda a}(t)$, $e_{m,\lambda b}(t)$, $\rho_{m,\lambda a}(t)$, and $\rho_{m,\lambda b}(t)$ (nc[m]·err_a and nc[m]·err_b, nc[m]·roh_a, and nc[m]·roh_b in the subroutine) are also calculated as in equations (70), (75), (68), and (71), respectively.

The loop iterates until the test for convergence is passed, the test being the same as described above for the subroutine tailored for the ratiometric method. The output of the present subroutine is a good approximation to the primary signals s"$_{\lambda a}$(t) and s"$_{\lambda b}$(t) or the secondary signals n"$_{\lambda a}$(t) and n"$_{\lambda b}$(t) for the set of samples $S_{\lambda a}(t)$ and $S_{\lambda b}(t)$ input to the program. After approximations to the primary signal portions or the secondary signals portions of many sets of measured signal samples are estimated by the joint process estimator, a compilation of the outputs provides waves which are good approximations to the plethysmographic wave or motion artifact at each wavelength, λa and λb. The estimating process of the iterative loop is the same in either subroutine, only the sample values $S_{\lambda a}(t)$ and $S_{\lambda c}(t)$ or $S_{\lambda a}(t)$ and $S_{\lambda b}(t)$ input to the subroutine for use in estimation of the primary signal portions $s_{\lambda a}(t)$ and $s_{\lambda c}(t)$ or $s_{\lambda a}(t)$ and $s_{\lambda b}(t)$ or of the secondary signal portions $n_{\lambda a}(t)$ and $n_{\lambda c}(t)$ or $n_{\lambda a}(t)$ and $n_{\lambda b}(t)$ and how the primary and secondary reference signals s'(t) and n'(t) are calculated are different for the ratiometric method and the constant saturation methods.

Independent of the method used, ratiometric or constant saturation, the approximations to either the primary signal values or the secondary signal values are input to a separate subroutine in which the saturation of oxygen in the arterial and venous blood is calculated. If the constant saturation method is used, the saturation calculation subroutine also determines values for the proportionality constants ωa(t) and $\omega_v(t)$ as defined in equation (3) and discussed above. The concentration of oxygenated arterial and venous blood can be found from the approximations to the primary or secondary signal values since they are made up of terms comprising x(t), the thickness of arterial and venous blood in the finger; absorption coefficients of oxygenated and de-oxygenated hemoglobin, at each measured wavelength; and $c_{Hb02}(t)$ and $c_{Hb}(t)$, the concentrations of oxygenated and de-oxygenated hemoglobin, respectively. The saturation is a ratio of the concentration of one constituent, $A_5$, with respect to the total concentration of constituents in the volume containing $A_5$ and $A_6$ or the ratio of the concentration of one constituent $A_3$, with respect to the total concentration of constituents in the volume containing $A_3$ and $A_4$. Thus, the thickness, x(t), is divided out of the saturation calculation and need not be predetermined. Additionally, the absorption coefficients are constant at each wavelength. The saturation of oxygenated arterial and venous blood is then determined as in equations (107) and (108).

While one embodiment of a physiological monitor incorporating a processor of the present invention for determining a reference signal for use in a correlation canceler, such as an adaptive noise canceler, to remove or derive primary and secondary components from a physiological measurement has been described in the form of a pulse oximeter, it will be obvious to one skilled in the art that other types of physiological monitors may also employ the above described techniques.

Furthermore, the signal processing techniques described in the present invention may be used to compute the arterial and venous blood oxygen saturations of a physiological system on a continuous or nearly continuous time basis. These calculations may be performed, regardless of whether or not the physiological system undergoes voluntary motion. The arterial pulsation induced primary plethysmographic signals $s_{\lambda a}(t)$ and $s_{\lambda b}(t)$ may be used to compute arterial blood oxygen saturation. The primary signals $s_{\lambda a}(t)$ and $s_{\lambda b}(t)$ can always be introduced into the measured signals $S_{\lambda a}(t)$ and $S_{\lambda b}(t)$ if at least two requirements are met. The two requirements include the selection of two or more flesh penetrating and blood absorbing wavelengths which are optically modulated by the arterial pulsation and an instrument design which passes all or portions of all electromagnetic signals which are related to the pulsation. Similarly, the secondary signals $n_{\lambda a}(t)$ and $n_{\lambda b}(t)$ related to venous blood flow may be used to compute its corresponding oxygen saturation. The secondary signal components $n_{\lambda a}(t)$ and $n_{\lambda b}(t)$ can be guaranteed to be contained in the measured signals $S_{\lambda a}(t)$ and $S_{\lambda b}(t)$ if the two or more flesh penetrating and blood absorbing wavelengths are processed to pass all or portions of all electromagnetic signals relating to venous blood flow. This may include but is not limited to all or portions of all signals which are related to the involuntary action of breathing. Similarly, it must be understood that there are many different types of physical systems which may be configured to yield two or more measurement signals each possessing a primary and secondary signal portion. In a great many of such physical systems it will be possible to derive one or more reference signals. The reference signals may be used in conjunction with a correlation canceler, such as an adaptive noise canceler, to derive either the primary and/or secondary signal components of the two or more measurement signals on a continuous or intermittent time basis.

Another embodiment of a physiological monitor incorporating a processor of the present invention for determining a reference signal for use in a correlation canceler, such as an adaptive noise canceler, to remove or derive primary and secondary components from a physiological measurement may be described in the form of a instrument which measures blood pressure. There are several ways of obtaining blood pressure measurements, such as tonometry, and pulse wave velocity. Both of these methods are substantially related to plethysmography.

Tonometry is a measurement method in which a direct reading of the arterial pressure pulse is made non-invasively. These measurements are invariably made through the use of a piezoelectric force transducer, the surface of which is gently pressed against a near-surface artery supported by underlying bone. If the transducer is sufficiently pressed against the artery that its surface is in complete contact with the tissue; then, knowing its surface area, its output can be directly read as pressure. This "flattening" of the arterial wall leads to the name of this method, applanation tonometry. The pulse wave velocity technique relies on the concept that the speed with which the pressure pulse, generated at the heart, travels "down" the arterial system is dependent on pressure. In each of these cases plethysmographic waveforms are used to determine the blood pressure of a patient.

Furthermore, it will be understood that transformations of measured signals other than logarithmic conversion and determination of a proportionality factor which allows removal or derivation of the primary or secondary signal portions for determination of a reference signal are possible. Additionally, although the proportionality factor ω has been described herein as a ratio of a portion of a first signal to a portion of a second signal, a similar proportionality constant determined as a ratio of a portion of a second signal to a portion of a first signal could equally well be utilized in the processor of the present invention. In the latter case, a secondary reference signal would generally resemble $n'(t)=n_{\lambda b}(t)-\omega n_{\lambda a}(t)$.

Furthermore, it will be understood that correlation cancellation techniques other than joint process estimation may be used together with the reference signals of the present invention. These may include but are not limited to least mean square algorithms, wavelet transforms, spectral estimation techniques, neural networks, Weiner filters, Kalman filters, QR-decomposition based algorithms among others. The implementation that we feel is the best, as of this filing, is the normalized least square lattice algorithm an implementation of which is listed in Appendix C.

It will also be obvious to one skilled in the art that for most physiological measurements, two wavelengths may be determined which will enable a signal to be measured which is indicative of a quantity of a component about which information is desired. Information about a constituent of any energy absorbing physiological material may be determined by a physiological monitor incorporating a signal processor of the present invention and an correlation canceler by determining wavelengths which are absorbed primarily by the constituent of interest. For most physiological measurements, this is a simple determination.

Moreover, one skilled in the art will realize that any portion of a patient or a material derived from a patient may be used to take measurements for a physiological monitor incorporating a processor of the present invention and a correlation canceler. Such areas include a digit such as a finger, but are not limited to a finger.

One skilled in the art will realize that many different types of physiological monitors may employ a signal processor of the present invention in conjunction with a correlation canceler, such as an adaptive noise canceler. Other types of physiological monitors include, but are in not limited to, electron cardiographs, blood pressure monitors, blood gas saturation (other than oxygen saturation) monitors, capnographs, heart rate monitors, respiration monitors, or depth of anesthesia monitors. Additionally, monitors which measure the pressure and quantity of a substance within the body such as a breathalizer, a drug monitor, a cholesterol monitor, a glucose monitor, a carbon dioxide monitor, a glucose monitor, or a carbon monoxide monitor may also employ the above described techniques for removal of primary or secondary signal portions.

Figure 32:
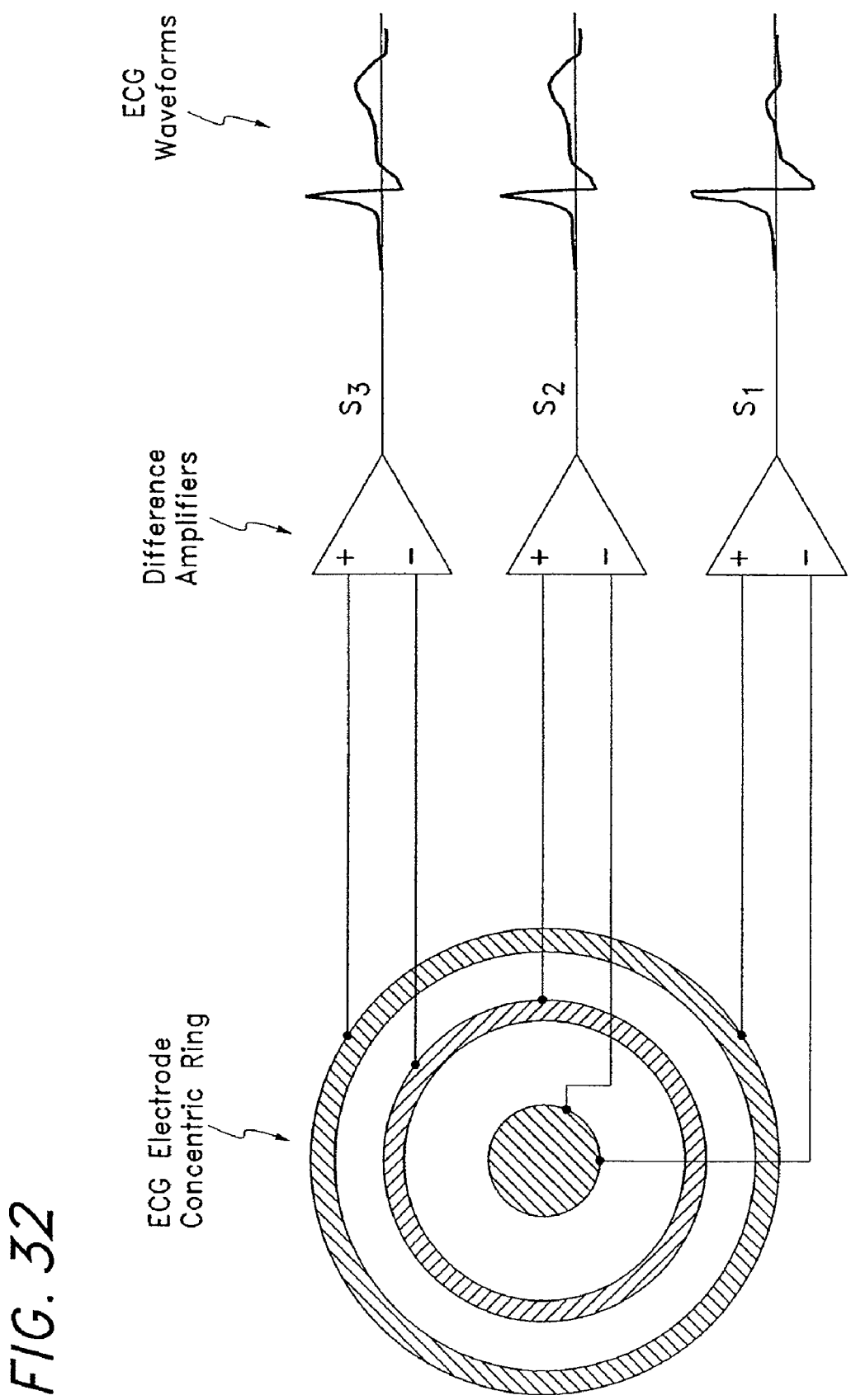
FIG. 32 depicts a set of 3 concentric electrodes, i.e. a tripolar electrode sensor, to derive electrocardiography (ECG) signals, denoted as $S_1$, $S_2$ and $S_3$, for use with the present invention. Each of the ECG signals contains a primary portion and a secondary portion.

Furthermore, one skilled in the art will realize that the above described techniques of primary or secondary signal removal or derivation from a composite signal including both primary and secondary components can also be performed on electrocardiography (ECG) signals which are derived from positions on the body which are close and highly correlated to each other. It must be understood that a tripolar Laplacian electrode sensor such as that depicted in FIG. 32 which is a modification of a bipolar Laplacian electrode sensor discussed in the article "Body Surface Laplacian ECG Mapping" by Bin He and Richard J. Cohen contained in the journal IEEE Transactions on Biomedical Engineering, Vol. 39, No. 11, November 1992 could be used as an ECG sensor. This article is hereby incorporated as reference. It must also be understood that there are a myriad of possible ECG sensor geometry's that may be used to satisfy the requirements of the present invention.

Furthermore, one skilled in the art will realize that the above described techniques of primary or secondary signal removal or derivation from a composite signal including both primary and secondary components can also be performed on signals made up of reflected energy, rather than transmitted energy. One skilled in the art will also realize that a primary or secondary portion of a measured signal of any type of energy, including but not limited to sound energy, X-ray energy, gamma ray energy, or light energy can be estimated by the techniques described above. Thus, one skilled in the art will realize that the processor of the present invention and a correlation canceler can be applied in such monitors as those using ultrasound where a signal is transmitted through a portion of the body and reflected back from within the body back through this portion of the body. Additionally, monitors such as echo cardiographs may also utilize the techniques of the present invention since they too rely on transmission and reflection.

While the present invention has been described in terms of a physiological monitor, one skilled in the art will realize that the signal processing techniques of the present invention can be applied in many areas, including but not limited to the processing of a physiological signal. The present invention may be applied in any situation where a signal processor comprising a detector receives a first signal which includes a first primary signal portion and a first secondary signal portion and a second signal which includes a second primary signal portion and a second secondary signal portion. The first and second signals propagate through a common medium and the first and second primary signal portions are correlated with one another. Additionally, at least a portion of the first and second secondary signal portions are correlated with one another due to a perturbation of the medium while the first and second signals are propagating through the medium. The processor receives the first and second signals and may combine the first and second signals to generate a secondary reference in which is uncorrelated with the primary signal portions of the measured signals or a primary reference which is uncorrelated with the secondary signal portions of the measured signals. Thus, the signal processor of the present invention is readily applicable to numerous signal processing areas.

What is claimed is:

1. A method determining a value of blood oxygen saturation of pulsing blood, the method comprising:
receiving three or more intensity signals from at least one light-sensitive detector which detects light attenuated by body tissue carrying pulsing blood, wherein the three or more intensity signals correspond to detection of at least three wavelengths of the light and the three or more intensity signals include motion induced noise; and
determining a value of oxygen saturation using the three or more intensity signals, wherein the determination reduces an effect of motion induced noise on said value.

2. The method of claim 1, wherein the step of determining further comprises processing at least two of the three or more intensity signals with an adaptive algorithm.

3. The method of claim 2, wherein the adaptive algorithm comprises a least squares algorithm.

4. The method of claim 3, wherein the least squares algorithm comprises a least squares lattice.

5. The method of claim 1, wherein one of the three or more intensity signals corresponds to one of the at least three wavelengths and wherein said determining comprises reducing an effect of the motion induced noise on the value of oxygen saturation using primarily said one of the at least three wavelengths.

6. The method of claim 5, wherein two of the three or more intensity signals correspond to two of the at least three wavelengths and wherein said determining comprises determining the value of oxygen saturation using primarily said two of the at least three wavelengths.

7. The method of claim 1, wherein absorption coefficients associated with two of the at least three wavelengths are related to one another in a manner predetermined to benefit processing during said determining said value of said oxygen saturation.

8. The method of claim 7, wherein absorption coefficients associated with two of the at least three wavelengths are proportional to one another.

9. The method of claim 7, wherein absorption coefficients associated with two of the at least three wavelengths are linearly proportional to one another.

10. The method of claim 1, wherein absorption coefficients associated with the at least three wavelengths are proportional to one another.

11. The method of claim 1, wherein each of the three or more intensity signals includes a signal portion and a noise portion, and wherein said determining includes a non-zero reference signal that corresponds to the noise portion of one of the three or more intensity signals.

12. The method of claim 1, wherein each of the three or more intensity signals includes a signal portion and a noise portion, and wherein said determining includes a non-zero reference signal that corresponds to the signal portion of one of the three or more intensity signals.

13. The method of claim 1, wherein the pulsing blood comprises arterial blood.

14. The method of claim 1, wherein the pulsing blood comprises venous blood.

15. A method of reducing an effect of motion induced noise on a plurality of intensity signals during the determination of a parameter of pulsing blood, the method comprising:
receiving a plurality of intensity signals from at least one light-sensitive detector which detects light of a plurality of wavelengths attenuated by body tissue carrying pulsing blood; and
processing one of the plurality of intensity signals using data from an additional intensity signal other than the plurality of intensity signals, the additional intensity signal corresponding to an additional wavelength of light, wherein the processing determines a value of blood oxygen saturation of the pulsing blood during motion induced noise, wherein the data from the extra wavelength is used to reduce an effect of the motion induced noise.

16. The method of claim 15, wherein the step of processing further comprises processing the plurality of intensity signals with an adaptive algorithm.

17. The method of claim 16, wherein the adaptive algorithm comprises a least squares algorithm.

18. The method of claim 17, wherein the least squares algorithm comprises a least squares lattice.

19. The method of claim 15, wherein absorption coefficients associated with the plurality of intensity signals are related to one another in a manner predetermined to benefit said processing.

20. The method of claim 19, wherein absorption coefficients associated with the plurality of intensity signals are proportional to one another.

21. The method of claim 19, wherein absorption coefficients associated with the plurality of intensity signals are linearly proportional to one another.

22. The method of claim 15, wherein absorption coefficients associated with the plurality of intensity signals and the additional intensity signal are proportional to one another in a manner predetermined to benefit said processing.

23. The method of claim 15, wherein the plurality of intensity signals and the additional intensity signal each includes a signal portion and a noise portion, and wherein said processing includes processing a non-zero reference signal that corresponds to the noise portion of one of the intensity signals.

24. The method of claim 15, wherein the plurality of intensity signals and the additional intensity signal each includes a signal portion and a noise portion, and wherein said processing includes processing a non-zero reference signal that corresponds to the signal portion of one of the intensity signals.

25. The method of claim 15, wherein the pulsing blood comprises arterial blood.

26. The method of claim 15, wherein the pulsing blood comprises venous blood.

27. A physiological monitor for determining a physiological parameter of a patient, the physiological monitor comprising:
an input which receives three or more intensity signals from at least one light-sensitive detector which detects light attenuated by body tissue carrying pulsing blood, wherein the three or more intensity signals correspond to detection of at least three wavelengths of the light and the three or more intensity signals include motion induced noise; and
a processor which determines a value of oxygen saturation using the three or more intensity signals while reducing an effect of motion induced noise on said value.

28. The physiological monitor of claim 27, wherein the processor processes at least two of the three or more intensity signals with an adaptive algorithm.

29. The physiological monitor of claim 28, wherein the adaptive algorithm comprises a least squares algorithm.

30. The physiological monitor of claim 29, wherein the least squares algorithm comprises a least squares lattice.

31. The physiological monitor of claim 27, wherein one of the three or more intensity signals corresponds to one of the at least three wavelengths and wherein the processor uses the one intensity signal primarily to reduce an effect of the motion induced noise on the value of oxygen saturation.

32. The physiological monitor of claim 31, wherein two of the three or more intensity signals corresponds to two of the at least three wavelengths and wherein the processor uses the two intensity signals primarily to determine the value of oxygen saturation.

33. The physiological monitor of claim 27, wherein absorption coefficients associated with two of the at least three wavelengths are related to one another in a manner predetermined to benefit processing by said processor in determining said value of said oxygen saturation.

34. The physiological monitor of claim 33, wherein absorption coefficients associated with two of the at least three wavelengths are proportional to one another.

35. The physiological monitor of claim 33, wherein absorption coefficients associated with two of the at least three wavelengths are linearly proportional to one another.

36. The physiological monitor of claim 27, wherein absorption coefficients associated with the at least three wavelengths are proportional to one another in a manner predetermined to benefit processing by said processor in determining said value of said oxygen saturation.

37. The physiological monitor of claim 27, wherein each of the three or more intensity signals includes a signal portion and a noise portion, and wherein said processor determines a non-zero reference signal that corresponds to the noise portion of one of the three or more intensity signals.

38. The physiological monitor of claim 27, wherein each of the three or more intensity signals includes a signal portion and a noise portion, and wherein said processor determines a non-zero reference signal that corresponds to the signal portion of one of the three or more intensity signals.

39. The physiological monitor of claim 27, wherein the pulsing blood comprises arterial blood.

40. The physiological monitor of claim 27, wherein the pulsing blood comprises venous blood.

* * * * *

UNITED STATES PATENT AND TRADEMARK OFFICE
CERTIFICATE OF CORRECTION

PATENT NO. : 7,937,130 B2
APPLICATION NO. : 12/340577
DATED : May 3, 2011
INVENTOR(S) : Mohamed K Diab, Esmaiel Kiani-Azarbayjany and Walter M. Weber It is certified that error appears in the above-identified patent and that said Letters Patent is hereby corrected as shown below:

- (Item 56) Page 9, Col. 2, Line 24, Under Other Publications, change "Mar" to --May--.

- Sheet 10 of 20 (Adjacent to Reference Numeral 70) (FIG. 8), Line 1 change "SQURES" to --SQUARES--.

- Sheet 12 of 20 (Adjacent to Reference Numeral 70) (FIG. 10), Line 1, change "SQURES" to --SQUARES--.

- Sheet 12 of 20 (Adjacent to Reference Numeral 106) (FIG. 10), Line 1, change "$s_{\lambda a} = s_{\lambda a} + n_{\lambda a}$" to --$s_{\lambda a} = s_{\lambda a} + n_{\lambda a}$--.

- Sheet 12 of 20 (Adjacent to Reference Numeral 108) (FIG. 10), Line 1-3, change
"$s_{\lambda b} = s_{\lambda b} + n_{\lambda b}$ OR $s_{\lambda c} = s_{\lambda c} + n_{\lambda c}$" to --$s_{\lambda b} = s_{\lambda b} + n_{\lambda b}$ OR $s_{\lambda c} = s_{\lambda c} + n_{\lambda c}$--.

- Column 20, Line 39, change "$m_{\lambda b}(t)$" to --$n_{\lambda b}(t)$--.

- Column 22, Line 35, change "$\varepsilon_{6,\lambda n}$" to --$\varepsilon_{6,\lambda a}$--.

- Column 22, Line 38, change "$n_{\lambda n}(t)$" to --$n_{\lambda a}(t)$--.

Signed and Sealed this
Twenty-second Day of November, 2011

David J. Kappos
*Director of the United States Patent and Trademark Office*

- Column 22, Line 40, change "$\varepsilon_{6,\lambda n}$" to --$\varepsilon_{6,\lambda a}$--.

- Column 20, Line 40, change "(25a)" to --(26a)--.

- Column 22, Line 42, change "$n_{\lambda n}(t)$" to --$n_{\lambda a}(t)$--.

- Column 22, Line 47, change "$\omega_a V$" to --$\omega_{av}$--.

- Column 22, Line 53, change "$\omega_a V$" to --$\omega_{av}$--.

- Column 35, Line 25, change "m$^{th}$ in" to --m$^{th}$--.

- Column 35, Line 28, change "min" to --m$^{th}$--.

- Column 35, Line 54-55, change "x$_5$,6(t)" to --x$_{5,6}$(t)--.

- Column 36, Line 9, change "x$_5$,6(t)." to --X$_{5,6}$(t).--.

- Column 41, Line 31-32, change "$\dfrac{\varepsilon_{HbO2,\lambda a} c^A_{HbO2} x(t) + \varepsilon_{Hb,\lambda a} c_{Hb} x(t)}{\varepsilon_{HbO2,\lambda b} c^A_{HbO2} x(t) + \varepsilon_{Hb,\lambda b} c_{Hb} x(t)} *$"

to -- $\dfrac{\varepsilon_{HbO2,\lambda a} c^A_{HbO2} x(t) + \varepsilon_{Hb,\lambda a} c_{Hb} x(t)}{\varepsilon_{HbO2,\lambda b} c^A_{HbO2} x(t) + \varepsilon_{Hb,\lambda b} c_{Hb} x(t)} *$ --.

- Column 54, Line 14, in Claim 32, change "corresponds" to --correspond--.